(12) United States Patent
Yoakim et al.

(10) Patent No.: US 8,039,638 B2
(45) Date of Patent: Oct. 18, 2011

(54) INHIBITORS OF HIV REPLICATION

(75) Inventors: Christiane Yoakim, Laval (CA);
Patrick Deroy, Blainville (CA); Martin Duplessis, Laval (CA); Alexandre Gagnon, Montreal (CA); Sylvie Goulet, Pierrefonds (CA); Oliver Hucke, Laval (CA); Christopher Lemke, Laval (CA); Simon Suprenant, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 247 days.

(21) Appl. No.: 12/517,310

(22) PCT Filed: Dec. 3, 2007

(86) PCT No.: PCT/CA2007/002155
§ 371 (c)(1),
(2), (4) Date: Jun. 22, 2009

(87) PCT Pub. No.: WO2008/067644
PCT Pub. Date: Jun. 12, 2008

(65) Prior Publication Data
US 2010/0069353 A1    Mar. 18, 2010

Related U.S. Application Data

(60) Provisional application No. 60/868,363, filed on Dec. 4, 2006.

(51) Int. Cl.
A61K 31/4184 (2006.01)
C07D 403/04 (2006.01)
(52) U.S. Cl. .................. 548/304.4; 514/394; 548/310.7
(58) Field of Classification Search .......... None
See application file for complete search history.

(56) References Cited

U.S. PATENT DOCUMENTS
2006/0142365 A1  6/2006  Lackey et al.

FOREIGN PATENT DOCUMENTS
| CA | 2319494 A1 | 8/1999 |
| CA | 2341409 A1 | 3/2000 |
| WO | 9940072 A1 | 8/1999 |
| WO | 0050419 A1 | 8/2000 |

OTHER PUBLICATIONS

International Search Report for corresponding PCT/CA2007/002155, mailed on Mar. 11, 2008.

*Primary Examiner* — Laura L. Stockton
(74) *Attorney, Agent, or Firm* — Michael P. Morris; Alan R. Stempel

(57) ABSTRACT

The present invention relates to compounds of formula (I) wherein $R^1$, $R^2$, $R^3$ and $R^4$ are as defined herein, compositions and uses thereof for treating human immunodeficiency virus (HIV) infection. In particular, the present invention provides novel inhibitors of HIV replication, pharmaceutical compositions containing such compounds and methods for using these compounds in the treatment of HIV infection.

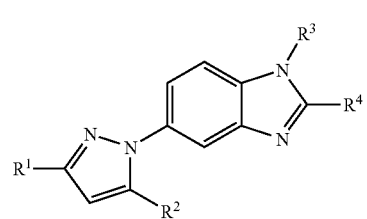

(I)

21 Claims, No Drawings

INHIBITORS OF HIV REPLICATION

This application is the national phase entry under 35 U.S.C. §371 of International Application No. PCT/CA2007/002155, filed Dec. 3, 2007, which claims priority from U.S. Provisional Application No. 60/868,363, filed Dec. 4, 2006, each of which is hereby incorporated by reference in its entirety.

FIELD OF THE INVENTION

The present invention relates to compounds, compositions and methods for the treatment of human immunodeficiency virus (HIV) infection. In particular, the present invention provides novel inhibitors of HIV replication, pharmaceutical compositions containing such compounds and methods for using these compounds in the treatment of HIV infection.

BACKGROUND OF THE INVENTION

Acquired immune deficiency syndrome (AIDS) is caused by the human immunodeficiency virus (HIV), particularly the HIV-1 strain. Most currently approved therapies for HIV infection target the viral reverse transcriptase and protease enzymes, with one additional approved drug targeting gp41 to inhibit viral entry. Within the reverse transcriptase inhibitor and protease inhibitor classes, resistance of HIV to existing drugs is a problem. Therefore, it is important to discover and develop new antiretroviral compounds.

SUMMARY OF THE INVENTION

The present invention provides a novel series of compounds having inhibitory activity against HIV replication. Further objects of this invention arise for the one skilled in the art from the following description and the examples.

One aspect of the invention provides compounds of formula (I):

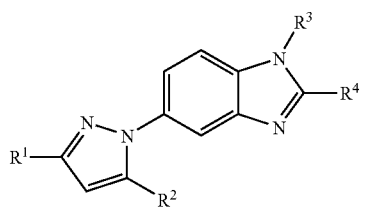

(I)

wherein
- $R^1$ is $(C_{1-4})$alkyl or $(C_{3-4})$cycloalkyl;
- $R^2$ is a 5- or 6-membered heterocycle containing 1 to 4 heteroatoms each independently selected from N, O and S, wherein the heterocycle is optionally substituted with 1 to 3 substituents each independently selected from halo, $(C_{1-6})$alkyl and $(C_{1-6})$haloalkyl;
- $R^3$ is $(C_{1-6})$alkyl, $(C_{3-7})$cycloalkyl-$(C_{1-6})$alkyl-, aryl-$(C_{1-6})$alkyl- or Het-$(C_{1-6})$alkyl-;
  - wherein each of the $(C_{1-6})$alkyl, $(C_{3-7})$cycloalkyl-$(C_{1-6})$alkyl-, aryl-$(C_{1-6})$alkyl- and Het-$(C_{1-6})$alkyl- is optionally substituted with 1 to 3 substituents each independently selected from $(C_{1-6})$alkyl, $(C_{1-6})$haloalkyl, halo, oxo, —$N_3$, —CN, —OH, —O$(C_{1-6})$alkyl, —$NH_2$, —NH$(C_{1-6})$alkyl, —N$((C_{1-6})$alkyl$)_2$, —NHC(=O)$(C_{1-6})$alkyl, —NHSO$_2$$(C_{1-6})$alkyl, —C(=O)—$NH_2$, —C(=O)—NH$(C_{1-6})$alkyl, —C(=O)—N$((C_{1-6})$alkyl$)_2$, —C(=O)$(C_{1-6})$alkyl, —SO$_2NH_2$, —SO$_2$NH$(C_{1-6})$alkyl, —SO$_2$N$((C_{1-6})$alkyl$)_2$, —SO$_2$$(C_{1-6})$alkyl, Het, Het-$(C_{1-6})$alkyl- and —C(=N$(C_{1-6})$alkyl)—N$((C_{1-6})$alkyl$)_2$; and
- $R^4$ is $(C_{1-6})$alkyl, $(C_{3-7})$cycloalkyl, $(C_{3-7})$cycloalkyl-$(C_{1-6})$alkyl-, aryl, aryl-$(C_{1-6})$alkyl-, Het, or Het-$(C_{1-6})$alkyl-;
  - wherein each of the $(C_{1-6})$alkyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is optionally substituted with 1 to 4 substituents each independently selected from $(C_{1-6})$alkyl, Het, halo, —$NO_2$, —OH, —O$(C_{1-6})$alkyl, —C(=O)$(C_{1-6})$alkyl, —COOH, —N$(R^{41})R^{42}$, —C(=O)—N$(R^{41})R^{42}$ and —SO$_2$—N$(R^{41})R^{42}$;
    - wherein each of the $(C_{1-6})$alkyl and —O$(C_{1-6})$alkyl are optionally substituted with —N$(R^{41})R^{42}$, —C(=O)—N$(R^{41})R^{42}$ or —O-Het;
  - wherein $R^{41}$ is H or $(C_{1-6})$alkyl and
  - $R^{42}$ is H, $(C_{1-6})$alkyl, $(C_{3-7})$cycloalkyl, $(C_{3-7})$cycloalkyl-$(C_{1-6})$alkyl-, aryl-$(C_{1-6})$alkyl-, Het or Het-$(C_{1-6})$alkyl-;
    - wherein the $(C_{1-6})$alkyl is optionally substituted with —CN, —OH, —O$(C_{1-6})$alkyl, —$NH_2$, —NH$(C_{1-6})$alkyl, —N$((C_{1-6})$alkyl$)_2$, —C(=O)—$NH_2$, —C(=O)—NH$(C_{1-6})$alkyl and —C(=O)—N$((C_{1-6})$alkyl$)_2$;
    - and wherein the aryl portion of the aryl-$(C_{1-6})$alkyl- and the Het are each optionally substituted with 1 to 3 substituents each independently selected from $(C_{1-6})$alkyl, —OH, —$NH_2$ and —C(=O)—O$(C_{1-6})$alkyl; or
  - $R^{41}$ and $R^{42}$ are linked, together with the N to which they are attached, to form a 4- to 7-membered heterocycle optionally further containing 1 to 3 heteroatoms each independently selected from O, N and S, or a 9- to 14-membered heteropolycycle optionally further containing 1 to 3 heteroatoms each independently selected from O, N and S; wherein each of the heterocycle and heteropolycycle is optionally substituted with 1 to 3 substituents each independently selected from $(C_{1-6})$alkyl, Het, halo, —OH, —$NH_2$, —NH$(C_{1-6})$alkyl, —N$((C_{1-6})$alkyl$)_2$, —CN, —COOH, —C(=O)—O$(C_{1-6})$alkyl, —C(=O)—$NH_2$, —C(=O)—NH$(C_{1-6})$alkyl and —C(=O)—N$((C_{1-6})$alkyl$)_2$;
    - wherein the $(C_{1-6})$alkyl is optionally substituted with —OH;
- wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;
or a salt or ester thereof.

Another aspect of this invention provides a compound of formula (I) or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of an HIV infection in a mammal having or at risk of having the infection.

A further aspect of the invention involves a method of treating an HIV infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating an HIV infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of an HIV infection in a mammal having or at risk of having the infection.

Another aspect of this invention provides the use of a compound of formula (I) as described herein, or a pharmaceutically acceptable salt or ester thereof, for the manufacture of a medicament for the treatment of an HIV infection in a mammal having or at risk of having the infection.

An additional aspect of this invention refers to an article of manufacture comprising a composition effective to treat an HIV infection; and packaging material comprising a label which indicates that the composition can be used to treat infection by HIV; wherein the composition comprises a compound of formula (I) according to this invention or a pharmaceutically acceptable salt or ester thereof.

Still another aspect of this invention relates to a method of inhibiting the replication of HIV comprising exposing the virus to an effective amount of the compound of formula (I), or a salt or ester thereof, under conditions where replication of HIV is inhibited.

Further included in the scope of the invention is the use of a compound of formula (I), or a salt or ester thereof, to inhibit the replication of HIV.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$ cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise, such that the substitution would give rise to a chemically stable compound, such as are recognized by those skilled in the art.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise, such that the substitution would give rise to a chemically stable compound, such as are recognized by those skilled in the art.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$, unless specified otherwise. When a Het group is substituted, it is understood that substituents may be attached to any carbon atom or heteroatom thereof which would otherwise bear a hydrogen atom, unless specified otherwise, such that the substitution would give rise to a chemically stable compound, such as are recognized by those skilled in the art.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl- group is substituted, it is understood that substituents may be attached to either the Het or the alkyl portion thereof or both, unless specified otherwise, such that the substitution would give rise to a chemically stable compound, such as are recognized by those skilled in the art.

The term "heteroatom" as used herein is intended to mean O, S or N.

The term "heterocycle" as used herein and unless specified otherwise, either alone or in combination with another radical, is intended to mean a 3- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine, and saturated, unsaturated and aromatic derivatives thereof, and the following heterocycle:

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzodioxole, benzothiazole, quinoline, isoquinoline, and naphthyridine.

The term "halo" as used herein is intended to mean a halogen substituent selected from fluoro, chloro, bromo and iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. When two or more hydrogen atoms are replaced by halo substituents, the halo substituents may be the same or different. Examples of $(C_{1-6})$haloalkyl include but are not limited to chloromethyl, chloroethyl, dichloroethyl, bromomethyl, bromoethyl, dibromoethyl, chlorobromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, are intended to mean an oxygen atom further bonded to an alkyl radical having 1 to n carbon atoms as defined above. Examples of —O—$(C_{1-6})$alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—$(C_{1-n})$alkyl radical is substituted, it is understood to be substituted on the $(C_{1-n})$alkyl portion thereof, such that the substitution would give rise to a chemically stable compound, such as are recognized by those skilled in the art.

The terms "—S—$(C_{1-n})$alkyl" or "$(C_{1-n})$alkylthio" as used herein interchangeably, wherein n is an integer, either alone or in combination with another radical, are intended to mean an sulfur atom further bonded to an alkyl radical having 1 to n carbon atoms as defined above. Examples of —S—$(C_{1-6})$alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—$(C_{1-n})$alkyl radical, or an oxidized derivative thereof, such as an —SO—$(C_{1-n})$alkyl radical or an —$SO_2$—$(C_{1-n})$alkyl radical, is substituted, each is understood to be substituted on the $(C_{1-n})$alkyl portion thereof, such that the substitution would give rise to a chemically stable compound, such as are recognized by those skilled in the art.

The term "oxo" as used herein is intended to mean an oxygen atom attached to a carbon atom as a substituent by a double bond (=O).

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acyl-sulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof.

As used herein, the designation whereby a bond to a substituent R is drawn as emanating from the center of a ring, such as, for example,

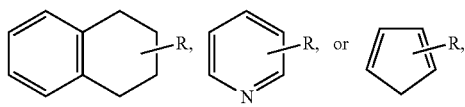

is intended to mean that the substituent R may be attached to any free position on the ring that would otherwise be substituted with a hydrogen atom, unless specified otherwise.

The following designation — is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Berge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids or organic acids. Suitable inorganic acids include but are not limited to hydrochloric acid, hydrobromic acid, sulfuric acid, sulfamic acid, nitric acid, phosphoric acid and the like. Suitable organic acids include but are not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases or organic bases. Suitable inorganic bases include but are not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985), herein incorporated by reference. Such pharmaceutically acceptable esters are usually hydrolyzed in vivo when administered to a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by HIV or non-human equivalents of HIV. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV-1 from mother to baby, by administration to the mother before giving birth and to the child within the first days of life.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

Preferred Embodiments

In the following preferred embodiments, groups and substituents of the compounds according to this invention are described in detail.

$R^1$:
  $R^1$-A: In one embodiment, $R^1$ is $(C_{1-4})$alkyl.
  $R^1$-B: In another embodiment, $R^1$ is methyl, ethyl, propyl, 1-methylethyl, butyl, 1-methylpropyl, 2-methylpropyl or 1,1-dimethylethyl.
  $R^1$-C: In another embodiment, $R^1$ is methyl or ethyl.
  $R^1$-D: In another embodiment, $R^1$ is ethyl.
  $R^1$-E: In an alternative embodiment, $R^1$ is $(C_{3-4})$cycloalkyl.
  $R^1$-F: In another alternative embodiment, $R^1$ is cyclopropyl.

Any and each individual definition of $R^1$ as set out herein may be combined with any and each individual definition of $R^2$, $R^3$ and $R^4$ as set out herein.

$R^2$:
  $R^2$-A: In one embodiment, $R^2$ is a 5-membered heterocycle containing 1 or 2 heteroatoms each independently selected from N, O and S, wherein the heterocycle is optionally substituted with 1 to 3 substituents each independently selected from halo, $(C_{1-6})$alkyl and $(C_{1-6})$haloalkyl.
  $R^2$-B: In another embodiment, $R^2$ is furyl or thienyl, each of the furyl and thienyl being optionally substituted with 1 or 2 substituents each independently selected from halo, $(C_{1-6})$alkyl and $(C_{1-6})$haloalkyl.
  $R^2$-C: In another embodiment, $R^2$ is furyl, optionally substituted with 1 or 2 substituents each independently selected from halo, $(C_{1-6})$alkyl and $(C_{1-6})$haloalkyl.
  $R^2$-D: In another embodiment, $R^2$ is furyl, optionally substituted with chloro, bromo, methyl or trifluoromethyl.
  $R^2$-E: In another embodiment, $R^2$ is thienyl, optionally substituted with 1 or 2 substituents each independently selected from halo, $(C_{1-6})$alkyl and $(C_{1-6})$haloalkyl.
  $R^2$-F: In another embodiment, $R^2$ is thienyl, optionally substituted with chloro, bromo, methyl or trifluoromethyl.
  $R^2$-G: In another embodiment, $R^2$ is selected from:

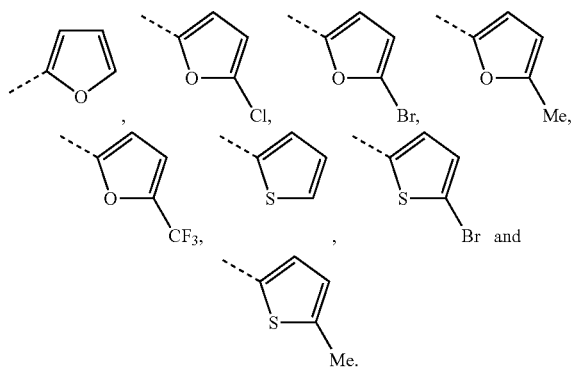

Any and each individual definition of $R^2$ as set out herein may be combined with any and each individual definition of $R^1$, $R^3$ and $R^4$ as set out herein.

$R^3$:
  $R^3$-A: In one embodiment, $R^3$ is $(C_{1-4})$alkyl optionally substituted with 1 or 2 substituents each independently selected from —O$(C_{1-4})$alkyl, —CN, —NH$_2$, —NH$(C_{1-4})$alkyl, —N$((C_{1-4})$alkyl$)_2$—NHC(=O)$(C_{1-4})$alkyl and —NHSO$_2(C_{1-6})$alkyl.
  $R^3$-B: In another embodiment, $R^3$ is $(C_{3-5})$cycloalkyl-$(C_{1-3})$alkyl-.
  $R^3$-C: In another embodiment, $R^3$ is aryl-$(C_{1-3})$alkyl- optionally substituted with 1 to 3 substituents each independently selected from $(C_{1-6})$alkyl, $(C_{1-6})$haloalkyl, halo, —N$_3$, —CN, —OH, —O$(C_{1-6})$alkyl, —NH$_2$, —NH$(C_{1-6})$alkyl, —N$((C_{1-6})$alkyl$)_2$, —NHC(=O)$(C_{1-6})$alkyl, —NHSO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)$(C_{1-6})$alkyl, SO$_2$NH$_2$, —SO$_2$NH$(C_{1-6})$alkyl, —SO$_2$N$((C_{1-6})$alkyl$)_2$, —SO$_2(C_{1-6})$alkyl, Het and Het-$(C_{1-6})$alkyl-.
  $R^3$-D: In another embodiment, $R^3$ is aryl-$(C_{1-3})$alkyl- optionally substituted with 1 to 3 substituents each independently selected from halo, —N$_3$, —OH, —O$(C_{1-4})$alkyl, —NH$_2$, —NH$(C_{1-4})$alkyl, —N$((C_{1-4})$alkyl$)_2$, —NHC(=O)$(C_{1-4})$alkyl, —SO$_2$NH$_2$, —SO$_2$NH$(C_{1-4})$alkyl, —SO$_2$N$((C_{1-4})$alkyl$)_2$, —SO$_2(C_{1-4})$alkyl, Het and Het-$(C_{1-6})$alkyl-;
    wherein the Het is a 5- or 6-membered heterocycle containing 1 to 3 heteroatoms each independently selected from N, O and S.
  $R^3$-E: In another embodiment, $R^3$ is aryl-CH$_2$— optionally substituted with 1 to 3 substituents each independently selected from halo, —N$_3$, —OH, —O$(C_{1-4})$alkyl, —NH$_2$, —NH$(C_{1-4})$alkyl, —N$((C_{1-4})$alkyl$)_2$, —NHC(=O)$(C_{1-4})$alkyl, —SO$_2$NH$_2$, —SO$_2$NH$(C_{1-4})$alkyl, —SO$_2$N$((C_{1-4})$alkyl$)_2$, —SO$_2(C_{1-4})$alkyl, Het and Het-$(C_{1-6})$alkyl-;
    wherein the Het is a 5- or 6-membered heterocycle containing 1 to 3 heteroatoms each independently selected from N, O and S.
  $R^3$-F: In another embodiment, $R^3$ is Het-$(C_{1-3})$alkyl- optionally substituted with 1 to 3 substituents each independently selected from $(C_{1-6})$alkyl, $(C_{1-6})$haloalkyl, halo, oxo, —N$_3$, —CN, —OH, —O$(C_{1-6})$alkyl, —NH$_2$, —NH$(C_{1-6})$alkyl, —N$((C_{1-6})$alkyl$)_2$, —NHC(=O)$(C_{1-6})$alkyl, —NHSO$_2(C_{1-6})$alkyl, —C(=O)—NH$_2$, —C(=O)—NH$(C_{1-6})$alkyl, —C(=O)—N$((C_{1-6})$ alkyl)$_2$, —C(=O)(C$_{1-6}$)alkyl, —SO$_2$NH$_2$, —SO$_2$NH(C$_{1-6}$)alkyl, —SO$_2$N((C$_{1-6}$)alkyl)$_2$, —SO$_2$(C$_{1-6}$)alkyl, Het, Het-(C$_{1-6}$)alkyl- and C(=N(C$_{1-6}$)alkyl)—N((C$_{1-6}$)alkyl)$_2$.

R$^3$-G: In another embodiment, R$^3$ is Het-(C$_{1-3}$)alkyl-, wherein the Het is a 5- or 6-membered heterocycle containing 1 to 3 heteroatoms each independently selected from N, O and S or the Het is a 9- or 10-membered heteropolycycle containing 1 to 3 heteroatoms each independently selected from N, O and S;

wherein the Het-(C$_{1-3}$)alkyl- is optionally substituted with 1 to 3 substituents each independently selected from (C$_{1-6}$)alkyl, (C$_{1-6}$)haloalkyl, oxo, —O(C$_{1-6}$)alkyl, —C(=N(C$_{1-6}$)alkyl)—N((C$_{1-6}$)alkyl)$_2$ and Het, wherein the Het is a 4, 5- or 6-membered heterocycle containing 1 to 3 heteroatoms each independently selected from N, O and S.

R$^3$-H: In another embodiment, R$^3$ is Het-(C$_{1-2}$)alkyl-, wherein the Het is pyridyl; and wherein the Het-(C$_{1-2}$)alkyl- is optionally substituted with 1 or 2 substituents each independently selected from (C$_{1-6}$)alkyl, oxo and —O(C$_{1-6}$)alkyl.

R$^3$-I: In another embodiment, R$^3$ is selected from:

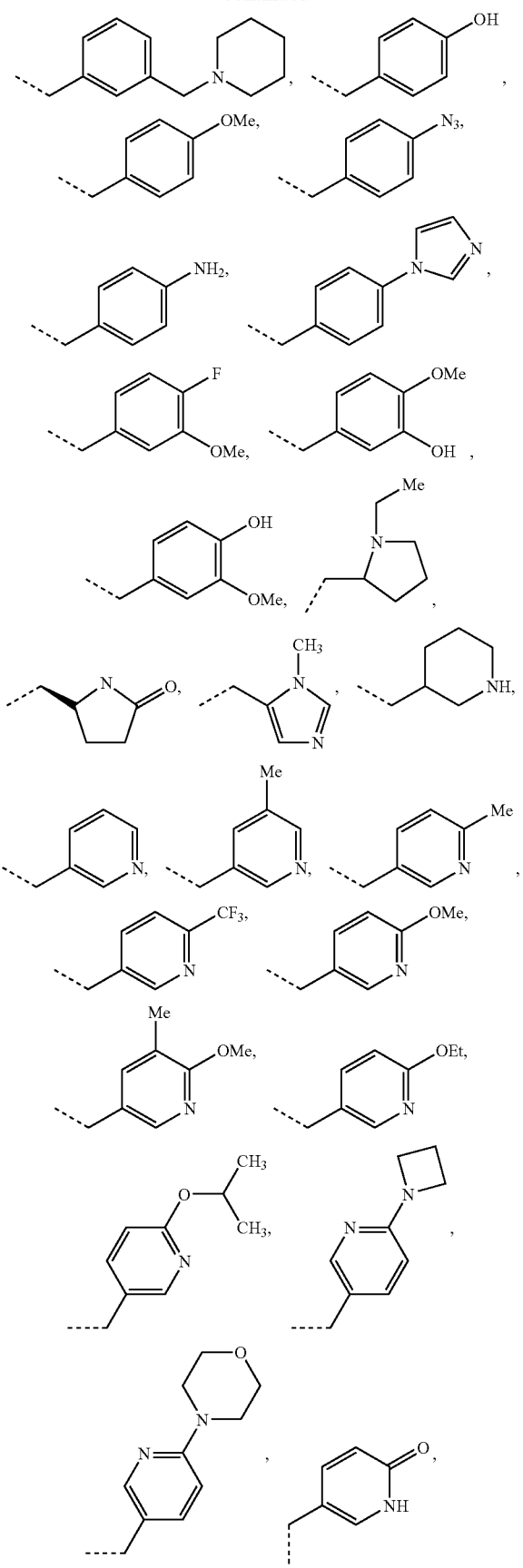

-continued

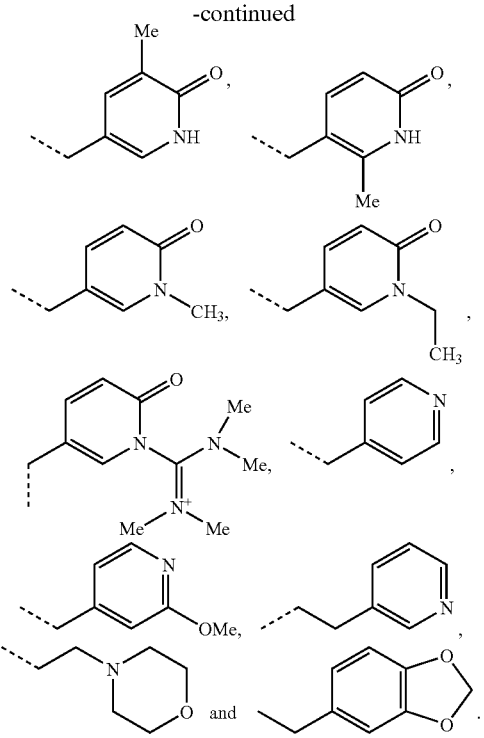

Any and each individual definition of $R^3$ as set out herein may be combined with any and each individual definition of $R^1$, $R^2$ and $R^4$ as set out herein.

$R^4$:

$R^4$-A: In one embodiment, $R^4$ is $(C_{1-6})$alkyl, $(C_{3-7})$cycloalkyl-$(C_{1-6})$alkyl-, aryl, aryl-$(C_{1-6})$alkyl- or Het;

wherein each of the $(C_{1-6})$alkyl, $(C_{3-7})$cycloalkyl-$(C_{1-6})$alkyl-, aryl, aryl-$(C_{1-6})$alkyl- and Het is optionally substituted with 1 to 4 substituents each independently selected from $(C_{1-6})$alkyl, Het, halo, —$NO_2$, —OH, —O$(C_{1-6})$alkyl, —C(=O)$(C_{1-6})$alkyl, —COOH, —N$(R^{41})R^{42}$, —C(=O)—N$(R^{41})R^{42}$ and —$SO_2$—N$(R^{41})R^{42}$;

wherein each of the $(C_{1-6})$alkyl and —O$(C_{1-6})$alkyl are optionally substituted with —N$(R^{41})R^{42}$, —C(=O)—N$(R^{41})R^{42}$ or —O-Het;

wherein $R^{41}$ is H or $(C_{1-6})$alkyl and $R^{42}$ is H, $(C_{1-6})$alkyl, $(C_{3-7})$cycloalkyl, $(C_{3-7})$cycloalkyl-$(C_{1-6})$alkyl-, aryl-$(C_{1-6})$alkyl-, Het or Het-$(C_{1-6})$alkyl-;

wherein the $(C_{1-6})$alkyl is optionally substituted with —CN, —OH, —O$(C_{1-6})$alkyl, —$NH_2$, —NH$(C_{1-6})$alkyl, —N$((C_{1-6})$alkyl$)_2$, —C(=O)—$NH_2$, —C(=O)—NH$(C_{1-6})$alkyl and —C(=O)—N$((C_{1-6})$alkyl$)_2$;

and wherein the aryl portion of the aryl-$(C_{1-6})$alkyl- and the Het are each optionally substituted with 1 to 3 substituents each independently selected from $(C_{1-6})$alkyl, —OH, —$NH_2$ and —C(=O)—O$(C_{1-6})$alkyl; or $R^{41}$ and $R^{42}$ are linked, together with the N to which they are attached, to form a 4- to 7-membered heterocycle optionally further containing 1 to 3 heteroatoms each independently selected from O, N and S, or a 9- to 14-membered heteropolycycle optionally further containing 1 to 3 heteroatoms each independently selected from O, N and S; wherein each of the heterocycle and heteropolycycle is optionally substituted with 1 to 3 substituents each independently selected from $(C_{1-6})$alkyl, Het, halo, —OH, —$NH_2$, —NH$(C_{1-6})$alkyl, —N$((C_{1-6})$alkyl$)_2$, —CN, —COOH, —C(=O)—O$(C_{1-6})$alkyl, —C(=O)—$NH_2$, —C(=O)—NH$(C_{1-6})$alkyl and —C(=O)—N$((C_{1-6})$alkyl$)_2$;

wherein the $(C_{1-6})$alkyl is optionally substituted with —OH;

$R^4$-B: In another embodiment, $R^4$ is $(C_{1-6})$alkyl, $(C_{3-7})$cycloalkyl-$(C_{1-6})$alkyl-, aryl-$(C_{1-6})$alkyl- or Het-$(C_{1-6})$alkyl-;

wherein each of the $(C_{1-6})$alkyl, $(C_{3-7})$cycloalkyl-$(C_{1-6})$alkyl-, aryl-$(C_{1-6})$alkyl- and Het-$(C_{1-6})$alkyl- is optionally substituted with —OH.

$R^4$-C: In another embodiment, $R^4$ is $(C_{1-6})$alkyl, $(C_{3-7})$cycloalkyl-$(C_{1-6})$alkyl- or aryl-$(C_{1-6})$alkyl-;

wherein each of the $(C_{1-6})$alkyl, $(C_{3-7})$cycloalkyl-$(C_{1-6})$alkyl- and aryl-$(C_{1-6})$alkyl- is optionally substituted with —OH.

$R^4$-D: In another embodiment, $R^4$ is aryl;

wherein the aryl is optionally substituted with 1 to 4 substituents each independently selected from $(C_{1-6})$alkyl, Het, halo, —OH, —O$(C_{1-6})$alkyl, —C(=O)$(C_{1-6})$alkyl, —COOH, —N$(R^{41})R^{42}$, —C(=O)—N$(R^{41})R^{42}$ and —$SO_2$—N$(R^{41})R^{42}$;

wherein each of the $(C_{1-6})$alkyl and —O$(C_{1-6})$alkyl are optionally substituted with —N$(R^{41})R^{42}$, —C(=O)—N$(R^{41})R^{42}$, or —O-Het;

wherein $R^{41}$ is H or $(C_{1-6})$alkyl and $R^{42}$ is H, $(C_{1-6})$alkyl, $(C_{3-7})$cycloalkyl, $(C_{3-7})$cycloalkyl-$(C_{1-6})$alkyl-, aryl-$(C_{1-6})$alkyl-, Het or Het-$(C_{1-6})$alkyl-;

wherein the $(C_{1-6})$alkyl is optionally substituted with —CN, —OH, —O$(C_{1-6})$alkyl, —$NH_2$, —NH$(C_{1-6})$alkyl, —N$((C_{1-6})$alkyl$)_2$, —C(=O)—$NH_2$, —C(=O)—NH$(C_{1-6})$alkyl and —C(=O)—N$((C_{1-6})$alkyl$)_2$;

and wherein the aryl portion of the aryl-$(C_{1-6})$alkyl- and the Het are each optionally substituted with 1 to 3 substituents each independently selected from $(C_{1-6})$alkyl, —OH, —$NH_2$ and —C(=O)—O$(C_{1-6})$alkyl; or $R^{41}$ and $R^{42}$ are linked, together with the N to which they are attached, to form a 4- to 7-membered heterocycle optionally further containing 1 to 3 heteroatoms each independently selected from O, N and S, or a 9- to 14-membered heteropolycycle optionally further containing 1 to 3 heteroatoms each independently selected from O, N and S; wherein each of the heterocycle and heteropolycycle is optionally substituted with 1 to 3 substituents each independently selected from $(C_{1-6})$alkyl, Het, halo, —OH, —$NH_2$, —NH$(C_{1-6})$alkyl, —N$((C_{1-6})$alkyl$)_2$, —CN, —COOH, —C(=O)—O$(C_{1-6})$alkyl, —C(=O)—$NH_2$, —C(=O)—NH$(C_{1-6})$alkyl and —C(=O)—N$((C_{1-6})$alkyl$)_2$;

wherein the $(C_{1-6})$alkyl is optionally substituted with —OH.

$R^4$-E: In another embodiment, $R^4$ is aryl of the formula:

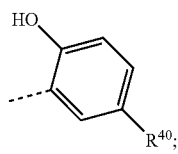

wherein $R^{40}$ is selected from $(C_{1-6})$alkyl, Het, halo, —O$(C_{1-6})$alkyl, —C(=O)$(C_{1-6})$alkyl, —COOH, —C(=O)—N$(R^{41})R^{42}$ and —SO$_2$—N$(R^{41})R^{42}$;
wherein Het is a 6-membered heterocycle containing 1 or 2 heteroatoms each independently selected from N, O and S; and
wherein the $(C_{1-6})$alkyl is optionally substituted with —N$(R^{41})R^{42}$ or —O-Het, wherein Het is a 6-membered heterocycle containing 1 or 2 heteroatoms each independently selected from N, O and S;
wherein $R^{41}$ is H or $(C_{1-6})$alkyl and
$R^{42}$ is H, $(C_{1-6})$alkyl, $(C_{3-7})$cycloalkyl, $(C_{3-7})$cycloalkyl-$(C_{1-6})$alkyl-, aryl-$(C_{1-6})$alkyl-, Het or Het-$(C_{1-6})$alkyl-;
wherein the $(C_{1-6})$alkyl is optionally substituted with —CN, —OH, —O$(C_{1-6})$alkyl, —NH$_2$, —NH$(C_{1-6})$alkyl, —N$((C_{1-6})$alkyl$)_2$, —C(=O)—NH$_2$, —C(=O)—NH$(C_{1-6})$alkyl and —C(=O)—N$((C_{1-6})$alkyl$)_2$;
and wherein the aryl portion of the aryl-$(C_{1-6})$alkyl- and the Het are each optionally substituted with 1 to 3 substituents each independently selected from $(C_{1-6})$alkyl, —OH, —NH$_2$ and —C(=O)—O$(C_{1-6})$alkyl; or
$R^{41}$ and $R^{42}$ are linked, together with the N to which they are attached, to form a 4- to 7-membered heterocycle optionally further containing 1 to 3 heteroatoms each independently selected from O, N and S; wherein the heterocycle is optionally substituted with 1 to 3 substituents each independently selected from $(C_{1-6})$ alkyl, Het, halo, —OH, —NH$_2$, —NH$(C_{1-6})$alkyl, —N$((C_{1-6})$alkyl$)_2$, —CN, —COOH, —C(=O)—O $(C_{1-6})$alkyl, —C(=O)—NH$_2$, —C(=O)—NH$(C_{1-6})$alkyl and —C(=O)—N$((C_{1-6})$alkyl$)_2$;
wherein the $(C_{1-6})$alkyl is optionally substituted with —OH; and
wherein the Het is a 5-membered heterocycle containing 1 to 3 heteroatoms each independently selected from N, O and S.

$R^4$-F: In another embodiment, $R^4$ is aryl of the formula:

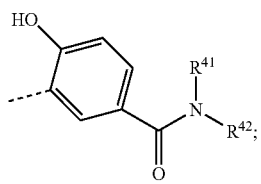

wherein $R^{41}$ is H or $(C_{1-6})$alkyl and
$R^{42}$ is H, $(C_{1-6})$alkyl or $(C_{3-7})$cycloalkyl;
wherein the $(C_{1-6})$alkyl is optionally substituted with —CN, —OH, —O$(C_{1-6})$alkyl, —NH$_2$, —NH$(C_{1-6})$alkyl, —N$((C_{1-6})$alkyl$)_2$, —C(=O)—NH$_2$, —C(=O)—NH$(C_{1-6})$alkyl and —C(=O)—N$((C_{1-6})$alkyl$)_2$; or $R^{41}$ and $R^{42}$ are linked, together with the N to which they are attached, to form a 4- to 7-membered heterocycle optionally further containing 1 to 3 heteroatoms each independently selected from O, N and S; wherein the heterocycle is optionally substituted with 1 to 3 substituents each independently selected from $(C_{1-6})$ alkyl, Het, halo, —OH, —NH$_2$, —NH$(C_{1-6})$alkyl, —N$((C_{1-6})$alkyl$)_2$, —CN, —COOH, —C(=O)—O $(C_{1-6})$alkyl, —C(=O)—NH$_2$, —C(=O)—NH$(C_{1-6})$ alkyl and —C(=O)—N$((C_{1-6})$alkyl$)_2$;
wherein the $(C_{1-6})$alkyl is optionally substituted with —OH; and
wherein the Het is a 5-membered heterocycle containing 1 to 3 heteroatoms each independently selected from N, O and S.

$R^4$-G: In another embodiment, $R^4$ is aryl of the formula:

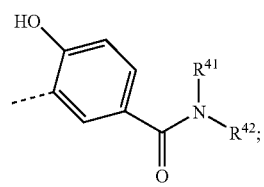

wherein $R^{41}$ is H or $(C_{1-6})$alkyl and $R^{42}$ is $(C_{1-6})$alkyl or $(C_{3-7})$cycloalkyl; or
$R^{41}$ and $R^{42}$ are linked, together with the N to which they are attached, to form a 4- to 6-membered heterocycle optionally further containing 1 to 3 heteroatoms each independently selected from O, N and S; wherein the heterocycle is optionally substituted with 1 or 2 substituents each independently selected from $(C_{1-6})$ alkyl, halo or —OH;
wherein the $(C_{1-6})$alkyl is optionally substituted with —OH.

$R^4$-H: In another embodiment, $R^4$ is Het, wherein Het is a 5- or 6-membered heterocycle containing 1 to 3 heteroatoms each independently selected from N, O and S, or Het is a 9- or 10-membered heteropolycycle containing 1 to 3 heteroatoms each independently selected from N, O and S, wherein each N heteroatom may, independently and where possible, exist in an oxidized state such that it is further bonded to an oxygen atom to form an N-oxide group;
wherein the Het is optionally substituted with 1 to 4 substituents each independently selected from $(C_{1-6})$ alkyl, —NO$_2$, —OH and —C(=O)—N$(R^{41})R^{42}$;
wherein $R^{41}$ is H or $(C_{1-6})$alkyl and $R^{42}$ is H or $(C_{1-6})$ alkyl.

$R^4$-I: In another embodiment, $R^4$ is selected from:

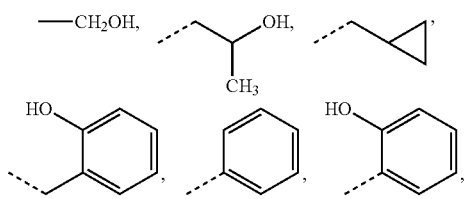

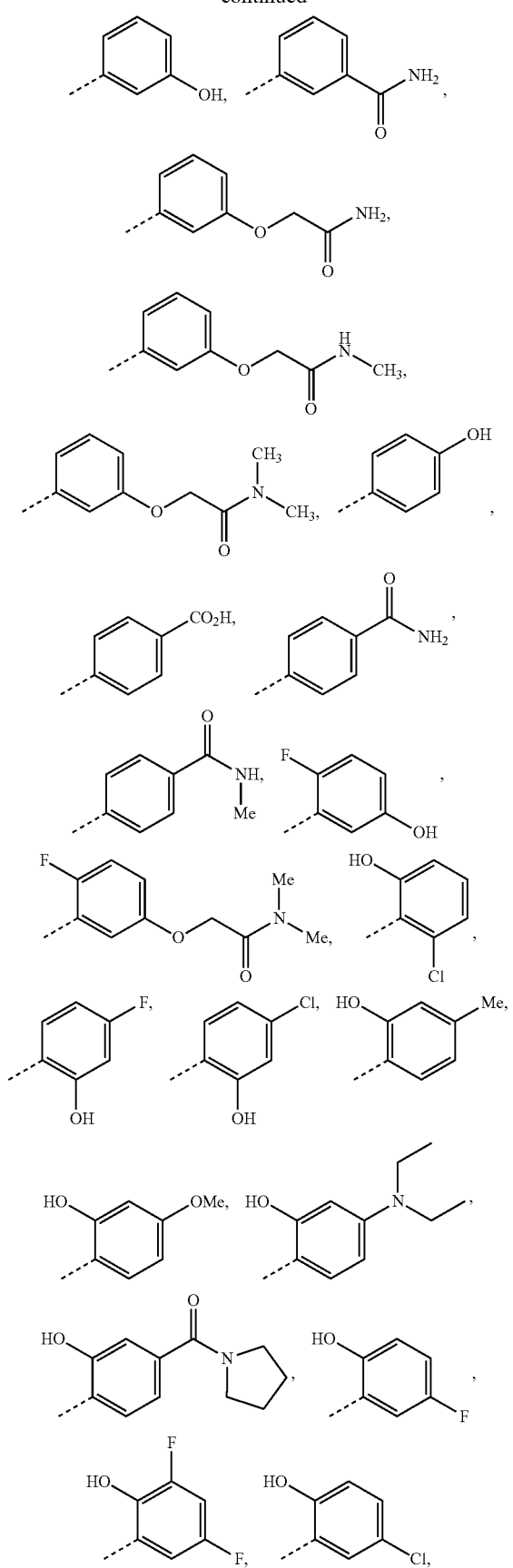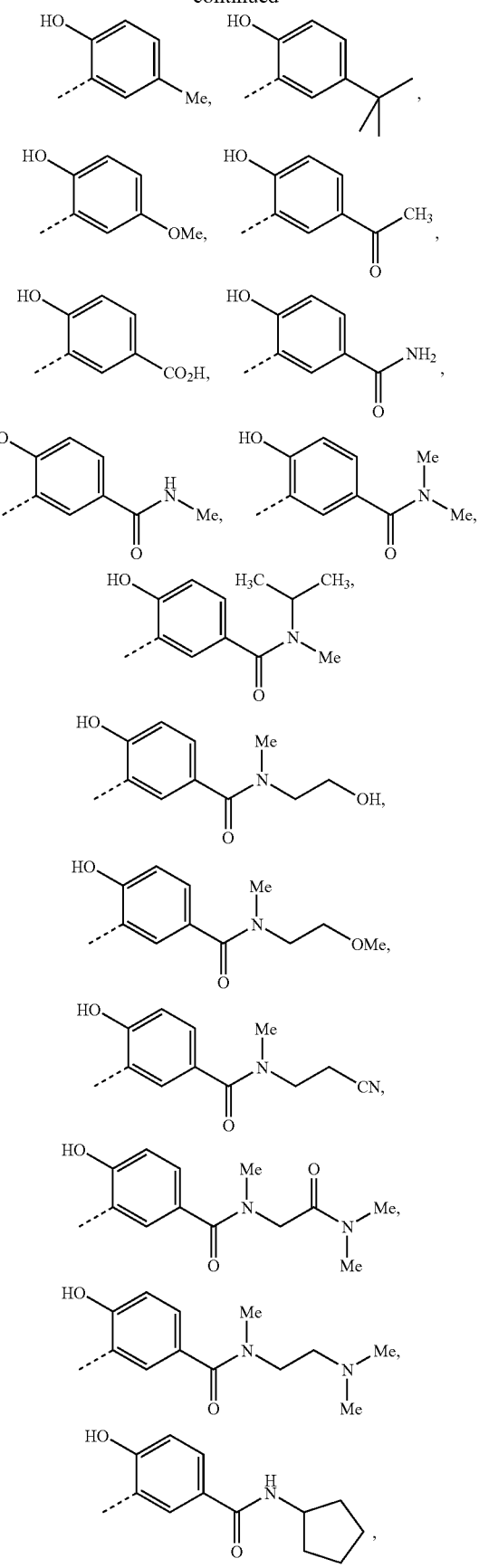

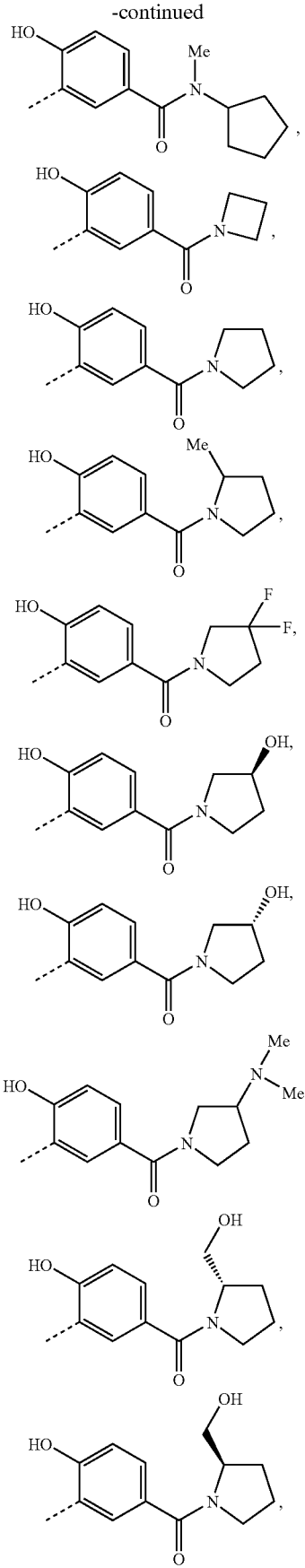
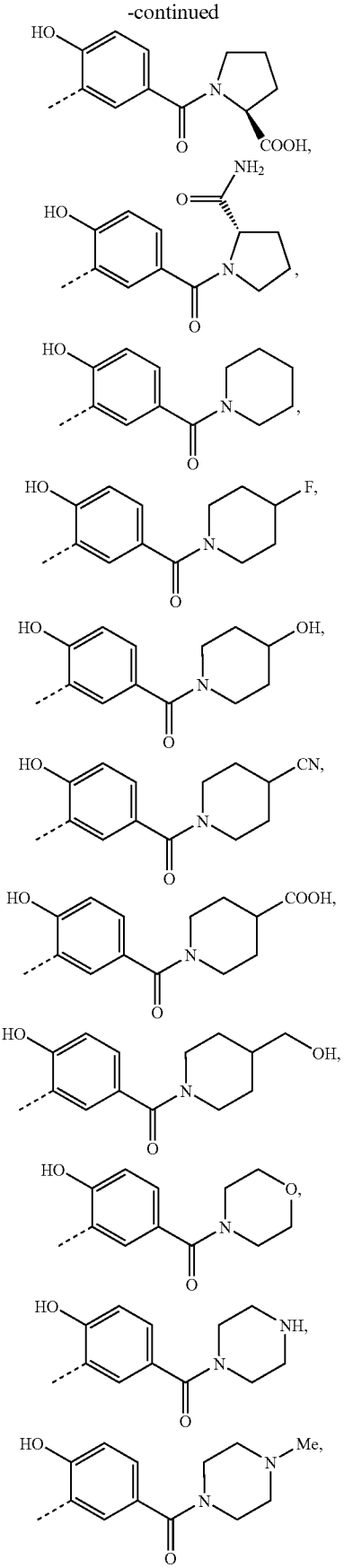

-continued
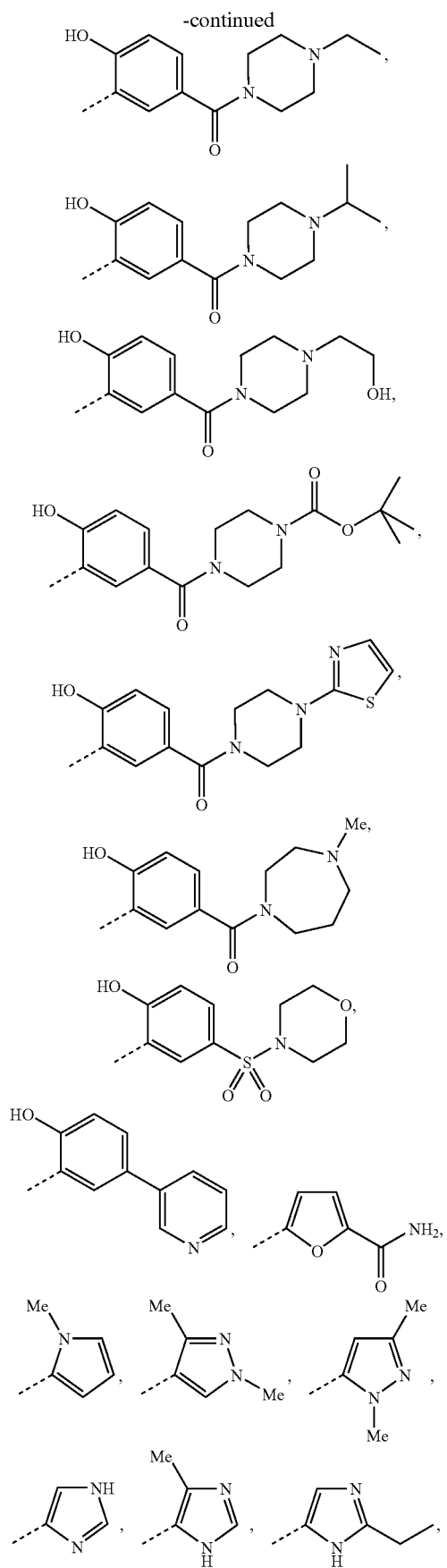
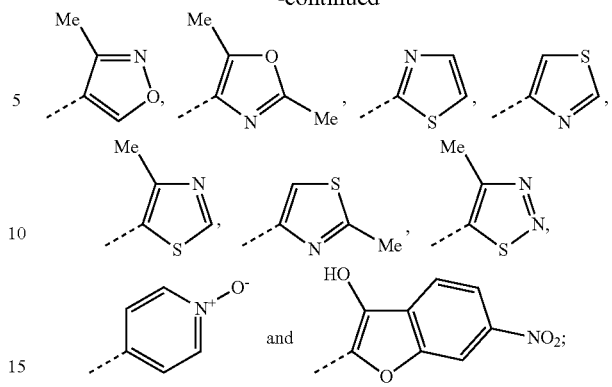
or R⁴ is a group of formula:
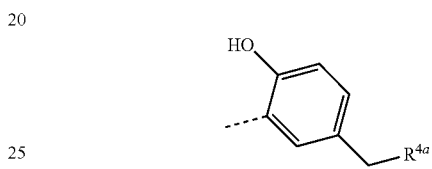
wherein $R^{4a}$ is selected from:
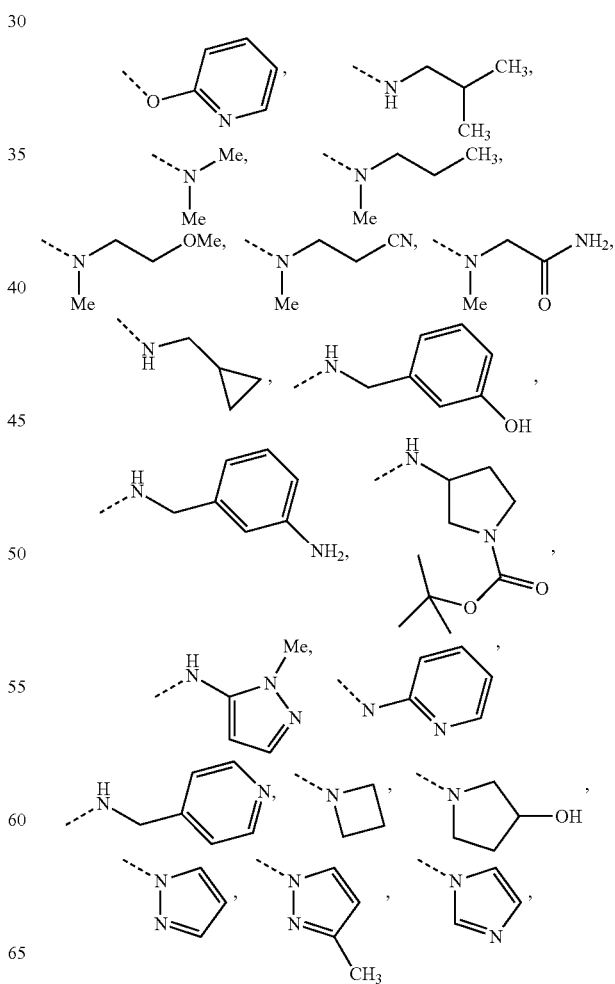

-continued

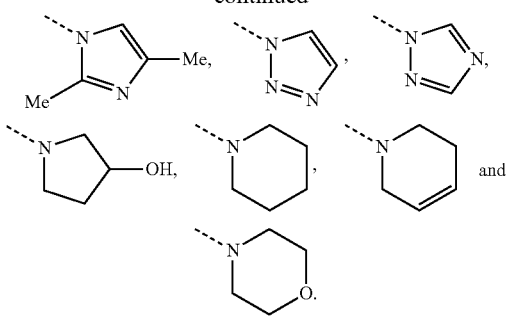

Any and each individual definition of $R^4$ as set out herein may be combined with any and each individual definition of $R^1$, $R^2$ and $R^3$ as set out herein.

Examples of preferred subgeneric embodiments of the present invention are set forth in the following table, wherein each substituent group of each embodiment is defined according to the definitions set forth above:

| Embodiment | $R^1$ | $R^2$ | $R^3$ | $R^4$ |
|---|---|---|---|---|
| E1 | $R^1$-A | $R^2$-C | $R^3$-A | $R^4$-B |
| E2 | $R^1$-E | $R^2$-C | $R^3$-A | $R^4$-B |
| E3 | $R^1$-A | $R^2$-E | $R^3$-A | $R^4$-B |
| E4 | $R^1$-E | $R^2$-E | $R^3$-A | $R^4$-B |
| E5 | $R^1$-A | $R^2$-C | $R^3$-B | $R^4$-B |
| E6 | $R^1$-E | $R^2$-C | $R^3$-B | $R^4$-B |
| E7 | $R^1$-A | $R^2$-E | $R^3$-B | $R^4$-B |
| E8 | $R^1$-E | $R^2$-E | $R^3$-B | $R^4$-B |
| E9 | $R^1$-A | $R^2$-C | $R^3$-C | $R^4$-B |
| E10 | $R^1$-E | $R^2$-C | $R^3$-C | $R^4$-B |
| E11 | $R^1$-A | $R^2$-E | $R^3$-C | $R^4$-B |
| E12 | $R^1$-E | $R^2$-E | $R^3$-C | $R^4$-B |
| E13 | $R^1$-A | $R^2$-C | $R^3$-F | $R^4$-B |
| E14 | $R^1$-E | $R^2$-C | $R^3$-F | $R^4$-B |
| E15 | $R^1$-A | $R^2$-E | $R^3$-F | $R^4$-B |
| E16 | $R^1$-E | $R^2$-E | $R^3$-F | $R^4$-B |
| E17 | $R^1$-A | $R^2$-C | $R^3$-A | $R^4$-D |
| E18 | $R^1$-E | $R^2$-C | $R^3$-A | $R^4$-D |
| E19 | $R^1$-A | $R^2$-E | $R^3$-A | $R^4$-D |
| E20 | $R^1$-E | $R^2$-E | $R^3$-A | $R^4$-D |
| E21 | $R^1$-A | $R^2$-C | $R^3$-B | $R^4$-D |
| E22 | $R^1$-E | $R^2$-C | $R^3$-B | $R^4$-D |
| E23 | $R^1$-A | $R^2$-E | $R^3$-B | $R^4$-D |
| E24 | $R^1$-E | $R^2$-E | $R^3$-B | $R^4$-D |
| E25 | $R^1$-A | $R^2$-C | $R^3$-C | $R^4$-D |
| E26 | $R^1$-E | $R^2$-C | $R^3$-C | $R^4$-D |
| E27 | $R^1$-A | $R^2$-E | $R^3$-C | $R^4$-D |
| E28 | $R^1$-E | $R^2$-E | $R^3$-C | $R^4$-D |
| E29 | $R^1$-A | $R^2$-C | $R^3$-F | $R^4$-D |
| E30 | $R^1$-E | $R^2$-C | $R^3$-F | $R^4$-D |
| E31 | $R^1$-A | $R^2$-E | $R^3$-F | $R^4$-D |
| E32 | $R^1$-E | $R^2$-E | $R^3$-F | $R^4$-D |
| E33 | $R^1$-A | $R^2$-C | $R^3$-A | $R^4$-H |
| E34 | $R^1$-E | $R^2$-C | $R^3$-A | $R^4$-H |
| E35 | $R^1$-A | $R^2$-E | $R^3$-A | $R^4$-H |
| E36 | $R^1$-E | $R^2$-E | $R^3$-A | $R^4$-H |
| E37 | $R^1$-A | $R^2$-C | $R^3$-B | $R^4$-H |
| E38 | $R^1$-E | $R^2$-C | $R^3$-B | $R^4$-H |
| E39 | $R^1$-A | $R^2$-E | $R^3$-B | $R^4$-H |
| E40 | $R^1$-E | $R^2$-E | $R^3$-B | $R^4$-H |
| E41 | $R^1$-A | $R^2$-C | $R^3$-C | $R^4$-H |
| E42 | $R^1$-E | $R^2$-C | $R^3$-C | $R^4$-H |
| E43 | $R^1$-A | $R^2$-E | $R^3$-C | $R^4$-H |
| E44 | $R^1$-E | $R^2$-E | $R^3$-C | $R^4$-H |
| E45 | $R^1$-A | $R^2$-C | $R^3$-F | $R^4$-H |
| E46 | $R^1$-E | $R^2$-C | $R^3$-F | $R^4$-H |
| E47 | $R^1$-A | $R^2$-E | $R^3$-F | $R^4$-H |
| E48 | $R^1$-E | $R^2$-E | $R^3$-F | $R^4$-H |

Examples of most preferred compounds according to this invention are each single compound listed in the following Tables 1 to 5.

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

For example, it is well known in the art that pyridones of formula P1 and hydroxypyridines of formula P2 are different tautomeric forms of the same species and interconvertible by proton transfer. Therefore, when a molecule, or a substituent thereof is represented by either formula P1 or P2, either and both forms are intended.

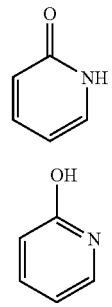

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD, ORD, X-ray crystallography, or NMR.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Pharmaceutical Composition

Compounds of the present invention may be administered to a mammal in need of treatment for HIV infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally, topically or systemically.

When one enantiomer of a chiral active ingredient has a different biological activity than the other, it is contemplated that the pharmaceutical composition according to the invention may comprise a racemic mixture of the active ingredient, a mixture enriched in one enantiomer of the active ingredient or a pure enantiomer of the active ingredient. The mixture enriched in one enantiomer of the active ingredient is contemplated to contain from about 50% to about 100% of one enantiomer of the active ingredient and from about 0% to about 50% of the other enantiomer of the active ingredient. Preferably, when the composition comprises a mixture enriched in one enantiomer of the active ingredient or a pure enantiomer of the active ingredient, the composition comprises from about 50% to about 100% of, or only, the more physiologically active enantiomer and/or the less toxic enantiomer. It is well known that one enantiomer of an active ingredient may be the more physiologically active for one therapeutic indication while the other enantiomer of the active ingredient may be the more physiologically active for a different therapeutic indication; therefore the preferred enantiomeric makeup of the pharmaceutical composition may differ for use of the composition in treating different therapeutic indications.

For oral administration, the compound, or a pharmaceutically acceptable salt or ester thereof, can be formulated in any orally acceptable dosage form including but not limited to aqueous suspensions and solutions, capsules or tablets. For topical administration, the compound, or a pharmaceutically acceptable salt or ester thereof, may be formulated in a pharmaceutically acceptable vehicle as a solution, cream or lotion. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004, herein incorporated by reference.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.001 to about 1000 milligrams per kilogram of body weight, with the preferred dose being about 0.01 to about 100 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from:

NRTIs (nucleoside or nucleotide reverse transcriptase inhibitors; including but not limited to zidovudine, didanosine, zalcitabine, stavudine, lamivudine, emtricitabine, abacavir, and tenofovir);
NNRTIs (non-nucleoside reverse transcriptase inhibitors; including but not limited to nevirapine, delavirdine, efavirenz, etravirine, rilpivirine and BILR 355);
protease inhibitors (including but not limited to ritonavir, tipranavir, saquinavir, nelfinavir, indinavir, amprenavir, fosamprenavir, atazanavir, lopinavir, darunavir and brecanavir);
entry inhibitors including but not limited to
CCR5 antagonists (including but not limited to maraviroc (UK-427,857), vicriviroc (SCH-D, SCH-417690) and TAK-652),
CXCR4 antagonists (including but not limited to AMD-11070),
fusion inhibitors (including but not limited to enfuvirtide (T-20)) and
others (including but not limited to BMS-488043);
integrase inhibitors (including but not limited to MK-0518, c-1605, BMS-538158 and GS 9137);
TAT inhibitors;
maturation inhibitors (including but not limited to bevirimat (PA-457)); and
immunomodulating agents (including but not limited to levamisole).

Furthermore, a compound according to the invention can be used with at least one other compound according to the invention or with one or more antifungal or antibacterial agents (including but not limited to fluconazole).

Therefore, according to one embodiment, the pharmaceutical composition of this invention additionally comprises one or more antiviral agents.

A further embodiment provides the pharmaceutical composition of this invention wherein the one or more antiviral agent comprises at least one NNRTI.

According to another embodiment of the pharmaceutical composition of this invention, the one or more antiviral agent comprises at least one NRTI.

According to yet another embodiment of the pharmaceutical composition of this invention, the one or more antiviral agent comprises at least one protease inhibitor.

According to still another embodiment of the pharmaceutical composition of this invention, the one or more antiviral agent comprises at least one entry inhibitor.

According to a further embodiment of the pharmaceutical composition of this invention, the one or more antiviral agent comprises at least one integrase inhibitor.

Methodology and Synthesis

The synthesis of compounds of formula (I) according to this invention is conveniently accomplished following the general procedures outlined in Schemes 1 and 2 below wherein $R^1$, $R^2$, $R^3$ and $R^4$ are as defined herein. Other procedures by which compounds of the invention may be prepared are well known in the art or are set forth in the examples below.

Scheme 1:

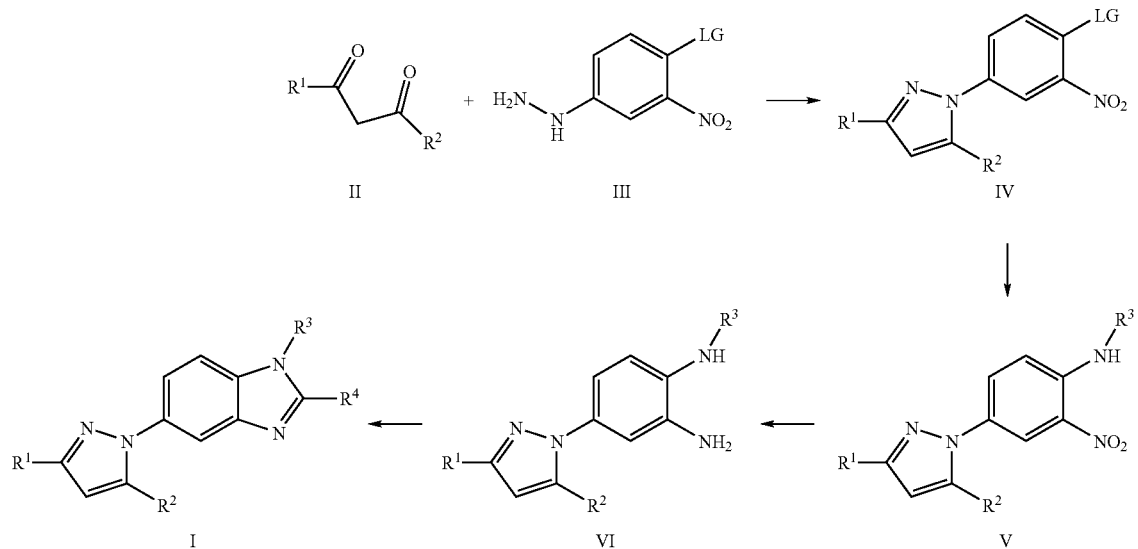

Intermediate II, wherein $R^1$ and $R^2$ are as defined herein, and intermediate III, wherein LG is a leaving group, including but not limited to a halogen atom such as F, are commercially available or are prepared by reactions well known in the art or as set forth in the examples below. Intermediates II and III are coupled under acidic conditions, including but not limited to treatment with acetic acid or trifluoroacetic acid, to give intermediates of formula IV. Reaction of intermediates IV with amines of formula $R^3$—$NH_2$, wherein $R^3$ is as defined herein, under well-known $S_NAr$ reaction conditions, provides intermediates of formula V. Reduction of intermediates V under well known conditions, including but not limited to treatment with Fe, or Sn and HCl, or hydrogenation conditions, give intermediates of formula VI. Intermediates VI are conveniently transformed to compounds of formula (I) by treatment with aldehydes of formula $R^4$—CHO, followed by oxidation with an oxidizing agent, including but not limited to Oxone™ ($2KHSO_5.KHSO_4.K_2SO_4$). Alternatively, intermediates VI may be transformed to compounds of formula (I) by condensation reactions well known in the art, including but not limited to treatment with carboxylic acids of formula $R^4$—COOH in the presence of pyridine, or treatment with carboxylic acid chlorides of formula $R^4$—COCl in the presence of pyridine.

Alternatively, compounds of formula (I) may be prepared by the general procedure outlined in Scheme 2 below.

Scheme 2:

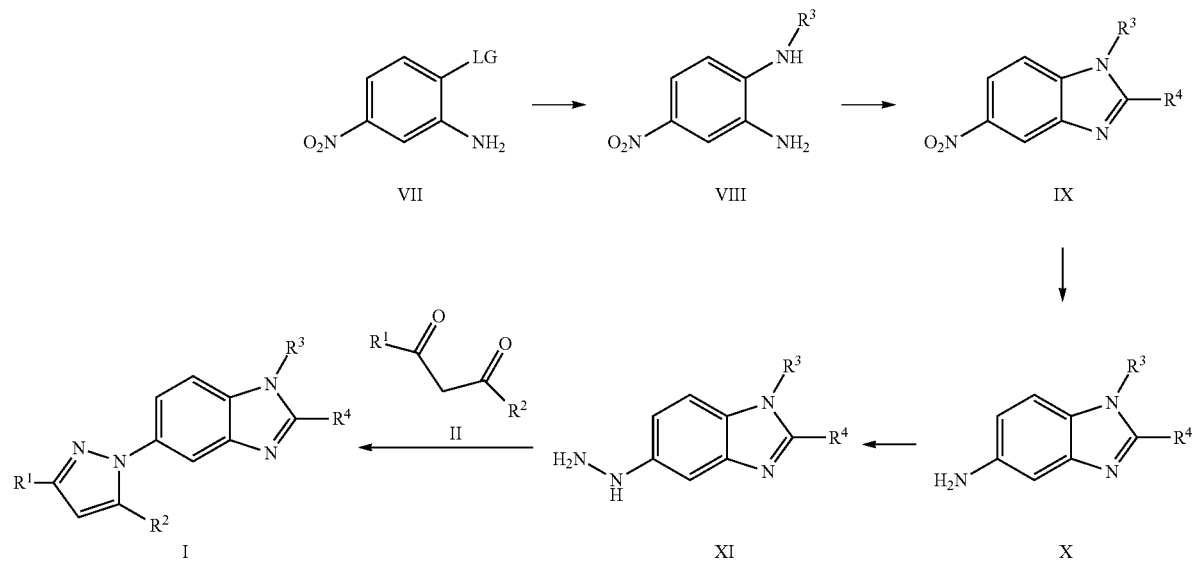

Intermediates VII, wherein LG is a leaving group, including but not limited to a halogen atom such as F, are commercially available or are prepared by reactions well known in the art or as set forth in the examples below. Reaction of intermediates VII with amines of formula $R^3$—$NH_2$, wherein $R^3$ is as defined herein, under well-known $S_NAr$ reaction conditions, provides intermediates of formula VIII. Intermediates VIII are conveniently transformed to intermediates of formula IX by treatment with aldehydes of formula $R^4$—CHO, followed by oxidation with an oxidizing agent, including but not limited to Oxone™ ($2KHSO_5.KHSO_4.K_2SO_4$). Alternatively, intermediates VIII may be transformed to intermediates of formula IX by condensation reactions well known in the art, including but not limited to treatment with carboxylic acids of formula $R^4$—COOH in the presence of pyridine, or treatment with carboxylic acid chlorides of formula $R^4$—COCl in the presence of pyridine. Reduction of intermediates IX under well known conditions, including but not limited to treatment with Fe, or Sn and HCl, or hydrogenation conditions, gives intermediates of formula X. Amine intermediates X are converted to hydrazine intermedates of formula XI by well known procedures, including but not limited to treatment with $NaNO_2$ in the presence of an acid such as HCl, followed by treatment with a suitable reducing agent such as $SnCl_2$ in the presence of an acid such as HCl. Intermediates XI are transformed to compounds of formula (I) by coupling with an intermediate of formula II under acidic conditions, including but not limited to treatment with acetic acid or trifluoroacetic acid, as described in Scheme 1 above and in the examples set forth below.

It will be apparent to one skilled in the art that a compound of formula I, or any of the intermediates II to XI involved in its preparation, wherein any of the substituents $R^1$, $R^2$, $R^3$ or $R^4$ has one meaning as defined herein, may be transformed to another compound of formula I, or to any of the intermediates II to XI involved in its preparation as appropriate, wherein any of the substituents $R^2$, $R^3$ or $R^4$ has a different meaning as defined herein, at any chemically convenient step in the preparation. In addition, the substituents $R^1$, $R^2$, $R^3$ or $R^4$ may be protected and/or deprotected at intermediate steps in the preparation of a compound of formula I, as will be recognized by the skilled person.

EXAMPLES

Other features of the present invention will become apparent from the following non-limiting examples which illustrate, by way of example, the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923. Mass spectral analyses are recorded using electrospray mass spectrometry. Preparative HPLC is carried out using a Combiprep ODS-AQ column, 50×20 mm, 5 μm, 120 Å, elution with a gradient of $CH_3CN/H_2O$ containing 0.06% TFA. Analytical HPLC is carried out under standard conditions using a Combiscreen ODS-AQ C18 reverse phase column, YMC, 50×4.6 mm i.d., 5 μm, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
AcOH: acetic acid;
Ac$_2$O: acetic anhydride;
BOC or Boc: tert-butyloxycarbonyl;
Bu: butyl;
DCM: dichloromethane;
DME: dimethoxyethane;
DMF: N,N-dimethylformamide;
DMSO: dimethylsulfoxide;
EC$_{50}$: 50% effective concentration;
Et: ethyl;
Et$_3$N: triethylamine;
Et$_2$O: diethyl ether;
EtOAc: ethyl acetate;
EtOH: ethanol;
HPLC: high performance liquid chromatography;
IC$_{50}$: 50% inhibitory concentration;
$^i$Pr or i-Pr: 1-methylethyl (iso-propyl);
Me: methyl;
MeCN: acetonitrile;
MeOH: methanol;
MS: mass spectrometry (MALDI-TOF: Matrix Assisted Laser Desorption Ionization-Time of Flight, FAB: Fast Atom Bombardment, ES: electrospray);
NaHMDS: sodium hexamethyldisilazide;
NMR: nuclear magnetic resonance spectroscopy;
Ph: phenyl;
PG: protecting group;
Pr: propyl;
RT: room temperature (approximately 18° C. to 25° C.);
TBTU: O-benzotriazol-1-yl-N,N,N',N'-tetramethyluronium tetrafluoroborate; tert-Bu or t-Bu: 1,1-dimethylethyl (tert-butyl or t-butyl)
TFA: trifluoroacetic acid;
THF: tetrahydrofuran;
TLC: thin layer chromatography.

Example 1A

Preparation of Intermediate 1a2

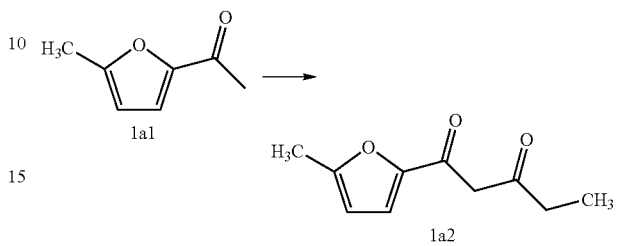

To a mixture of diisopropylamine (17 mL, 1.5 eq.) and THF (200 mL) at −50° C. is added n-BuLi (7.7 g, 1.5 eq.). The reaction mixture is allowed to stir at 0° C. for 1 hour and cooled to −78° C., and a mixture of compound 1a1 (10 g, 1.0 eq) and THF (100 mL) is added. Stirring is continued at −78° C. for 15 minutes. Propanoyl chloride (8.1 g, 1.1 eq.) is added and stirring is continued at −78° C. for 2 h and at room temperature for 1 h. Saturated NH$_4$Cl (50 mL) is added and the mixture is concentrated under reduced pressure and the residue is extracted with EtOAc (2×200 mL). The organic extract is washed with 1 N HCl (200 mL) and brine (200 mL), dried over anhydrous Na$_2$SO$_4$ and concentrated under reduced pressure. The residue is purified by column chromatography (pet. ether/EtOAc (1:8)) to provide compound 1a2.

Example 1B

Preparation of Intermediate 1b7

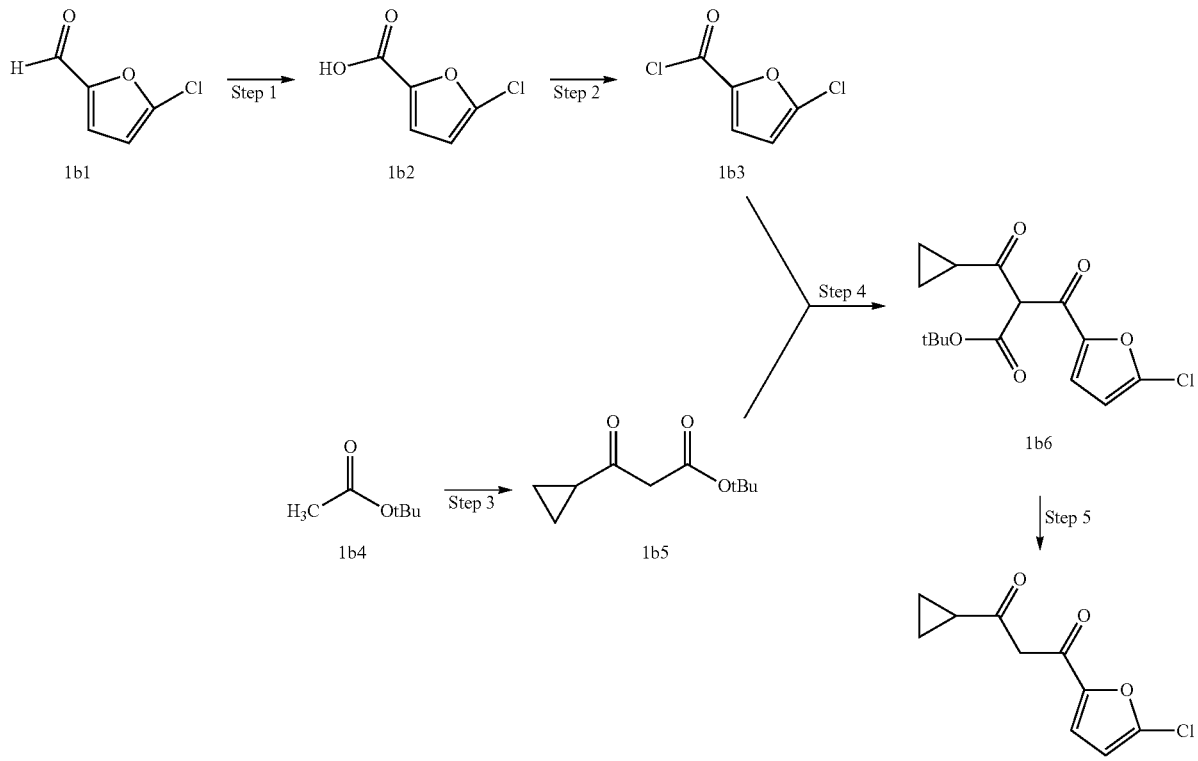

Step 1:

To a mixture of compound 1b1 (5.0 g, 1.0 eq.) and tert-butanol (30 mL) is added 2-methyl-2-butene (13.5 g, 5.0 eq.), aqueous $NaH_2PO_4$ (150 mL containing 29.8 g of $NaH_2PO_4$, 5.0 eq.) and $NaClO_3$ (13.8 g, 4.0 eq.). The mixture is allowed to stir at room temperature for 3 h, then is extracted with EtOAc (6×150 mL). The combined organic extract is dried ($Na_2SO_4$), filtered and concentrated under reduced pressure to provide compound 1b2.

Step 2:

To a mixture of compound 1b2 (3.0 g, 1.0 eq.) and $CH_2Cl_2$ (30 mL) at 0° C. is added DMF (0.1 mL) and $(COCl)_2$ (6.7 g, 2.5 eq.). The mixture is allowed to stir at room temperature for 3 h, then concentrated under reduced pressure to give compound 1b3.

Step 3:

To a mixture of diisopropylamine (10.5 g, 2.0 eq.) and THF (80 mL) at −78° C. is added n-BuLi (6.6 g, 2.0 eq.) and the mixture is stirred at 0° C. for 1 hour and cooled to −78° C. To the mixture is added a mixture of compound 1b4 (6.0 g, 1.0 eq.) and THF (50 mL) and stirring is continued at −78° C. for 30 minutes. A mixture of cyclopropanecarbonyl chloride (6.0 g, 1.1 eq) and THF (50 mL) is added and the mixture is allowed to react at −78° C. for 2 h, and allowed to warm slowly to 0° C. Saturated $NH_4Cl$ (100 mL) is added at −30° C. and the mixture is extracted with $Et_2O$ (2×200 mL). The organic extract is washed with 1N HCl (200 mL) and brine (200 mL), dried ($Na_2SO_4$) and concentrated under reduced pressure. The residue is purified by chromatography (4-5% EtOAc/pet. ether) to provide compound 1b5.

Step 4:

A mixture of compound 1b5 (2.8 g, 1.2 eq.), anhydrous $MgCl_2$ (3.3 g, 2.0 eq.), MeCN (15 mL) and $Et_3N$ (3.5 g, 2.0 eq.) is allowed to stir at room temperature for 15-30 minutes. A mixture of compound 1b3 (2.8 g, 1.0 eq.) in MeCN (15 mL) is added and the reaction mixture is allowed to stir at room temperature overnight. The mixture is cooled to 0° C. and water (200 mL) is added. The mixture is extracted with EtOAc (200 mL+150 mL) and the combined organic extract is washed with 1N HCl (200 mL) and brine (200 mL), dried ($Na_2SO_4$) and concentrated under reduced pressure to give compound 1b6.

Step 5:

To a mixture of compound 1b6 (5.4 g, 1.0 eq.) and $CH_2Cl_2$ (21.2 mL) is added TFA (10.8 mL). The mixture is stirred at room temperature for 1 h and concentrated under reduced pressure. The residue is purified by chromatography (1-2% $Et_2O$/pet. ether) to give compound 1b7.

Other intermediates of formula II are commercially available or are prepared using the procedures of Examples 1A or 1B, modified appropriately as is apparent to one skilled in the art.

Example 2A

Preparation of Intermediate 2a2

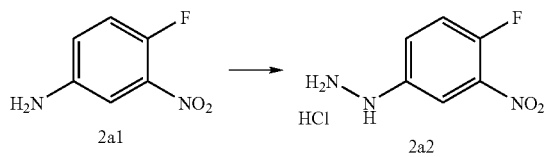

A mixture of compound 2a1 (10 g, 1 eq.) and aqueous HCl (12M, 50 mL) is stirred at room temperature for 30 minutes, then cooled to −25° C. and a mixture of $NaNO_2$ (4.8 g, 1.1 eq.) and aqueous HCl (12M, 40 mL) is added. The mixture is allowed to stir at −25° C. for 1 hour and a mixture of $SnCl_2$ (29.1 g, 2.4 eq.) and aqueous HCl (12M, 30 mL) is added. The mixture is allowed to warm to room temperature and stir for 1 hour, then is filtered. The solid is washed with $Et_2O$ and dried under reduced pressure to provide compound 2a2 as the hydrochloride salt.

Other intermediates of formula III are commercially available or are prepared using the procedure of Example 2A, modified appropriately as is apparent to one skilled in the art.

Example 3A

Preparation of Intermediate 3a1

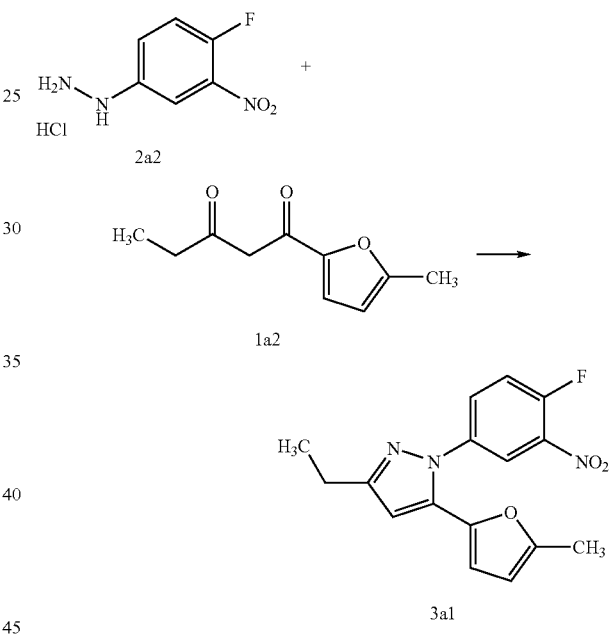

A mixture of compound 2a2 (3.94 g, 23.0 mmol) and diketone 1a2 (3.75 g, 20.8 mmol) in AcOH (40 mL) is stirred at room temperature for 1 hour. The reaction mixture is concentrated to dryness and the residue is purified by flash column chromatography using hexane/EtOAc (9.5/0.5 to 9/1) to obtain compound 3a1.

Example 3B

Preparation of Intermediate 3b2

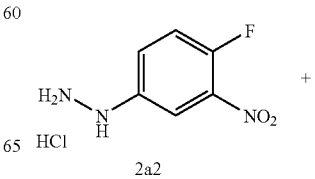

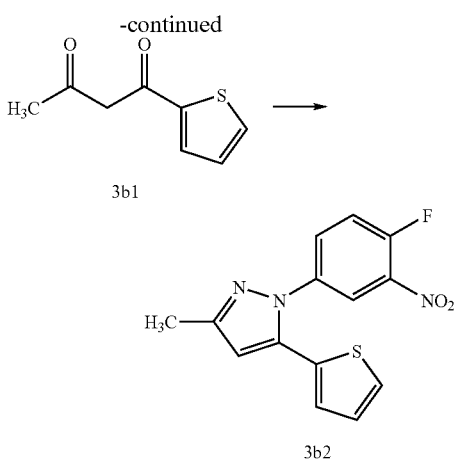

To a mixture of compound 2a2 (3.42 g, 20 mmol), compound 3b1 (prepared from thiophenecarbonyl chloride and tert-butylacetoacetate using the procedure of Steps 4 and 5 of Example 1B) (3.36 g, 20 mmol) and MeOH (200 mL) at 0° C. is added Et₃N (6.4 mL, 46 mmol) and the mixture is allowed to stir at room temperature for 1 h. The mixture is concentrated under reduced pressure and diluted with THF (60 mL) at 0° C. To this mixture is added TFA (20 mL) and the mixture is allowed to stir at room temperature for 30 minutes. The mixture is concentrated under reduced pressure and purified by flash chromatography (hexane:EtOAc, 90:10 to 85:15) to give compound 3b2.

Other intermediates of formula IV are prepared using the procedures of Examples 3A or 3B, modified appropriately as is apparent to one skilled in the art.

Example 4A

Preparation of Intermediate 4a3

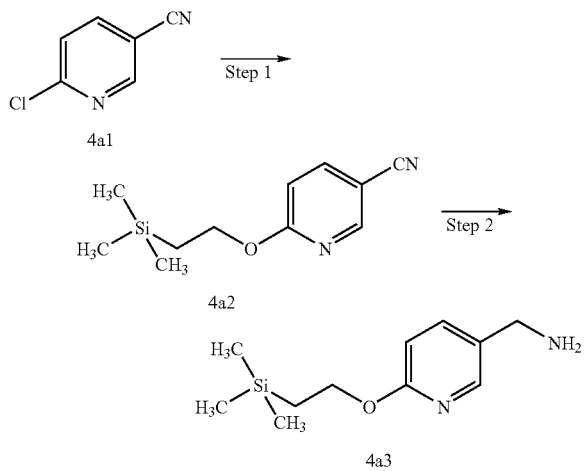

Step 1:
To a mixture of compound 4a1 (3.31 g, 23.9 mmol) and 2-(trimethylsilyl)ethanol (4.11 mL, 28.7 mmol) in THF (75 mL) at 0° C. is added NaHMDS (1M/THF, 29.0 mL, 29.0 mmol). After 1 hour the reaction mixture is diluted in Et₂O, washed with water and brine, dried over MgSO₄, filtered and concentrated under reduced pressure to provide compound 4a2.

Step 2:
A mixture of compound 4a2 (5.3 g, 24.1 mmol) and Pd/C (10%, 500 mg) in MeOH (100 mL) is stirred under H₂ (1 atm) for 16 h. The catalyst is removed by filtration through Celite™ (diatomaceous earth). The filtrate is concentrated under reduced pressure to give compound 4a3.

Example 4B

Preparation of Intermediate 4b5

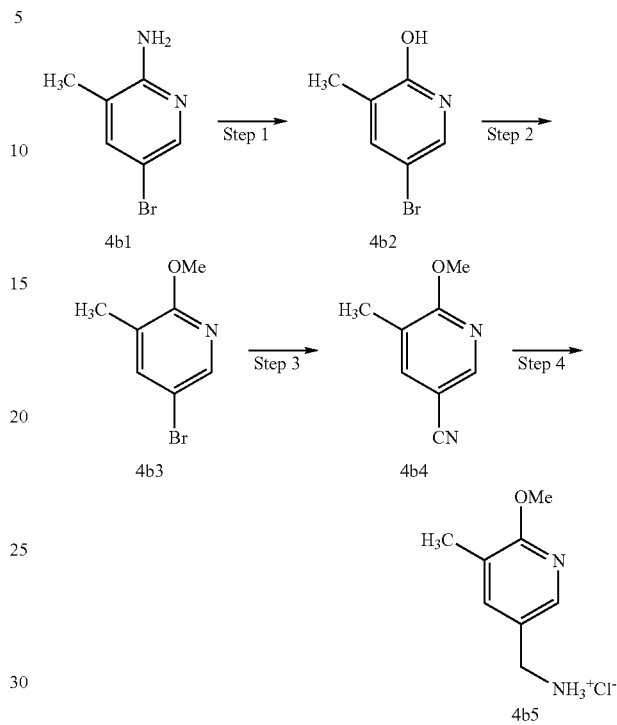

Step 1:
To a mixture of compound 4b1 (600 mg, 3.2 mmol) and concentrated H₂SO₄ (1.6 mL) and water (18.4 mL) is added drop wise a solution of NaNO₂ (243.5 mg, 3.53 mmol) in water (1.6 mL) at 0° C. After 30 min at room temperature the reaction is filtered and the resulting solid is washed with water and dried under high vacuum to give compound 4b2.

Step 2:
To a mixture of compound 4b2 (2 g, 10.6 mmol) and CH₂Cl₂ (100 mL) is added Ag₂CO₃ (8.8 g, 31.9 mmol) and CH₃I (7 mL, 112 mmol). The reaction mixture is stirred at room temperature overnight, then filtered through diatomaceous earth (Celite™). The filtrate is concentrated under reduced pressure to give compound 4b3.

Step 3:
To a mixture of compound 4.3 (2.13 g, 10.5 mmol) and DMF (10 mL) is added CuCN (1.13 g, 12.6 mmol) and the resulting mixture is heated at reflux for 28 h. After cooling to room temperature the mixture is diluted with EtOAc and a mixture of FeCl₃ (8 g) in concentrated HCl (2 mL) and water (8 mL) is added. The mixture is poured over 1N NaOH and ice. The organic layer is separated and washed with water and brine, dried over MgSO₄, filtered and evaporated. The residue is purified by flash chromatography (5% EtOAc/Hexane) to give compound 4b4.

Step 4:
A mixture of 4b4 (1.22 g, 8.23 mmol), MeOH (90 mL), HCl (1N, 9.1 mL) and Pd/C (10%, 600 mg) is stirred under hydrogen (1 atm) for 16 h. The catalyst is removed by filtration through diatomaceous earth (Celite™). The filtrate is concentrated under reduced pressure to give compound 4b5.

Other intermediates of formula R³—NH₂ are commercially available or are prepared using the procedures of Examples 4A or 4B, modified appropriately as is apparent to one skilled in the art.

Example 5A

Preparation of Intermediate 5a1

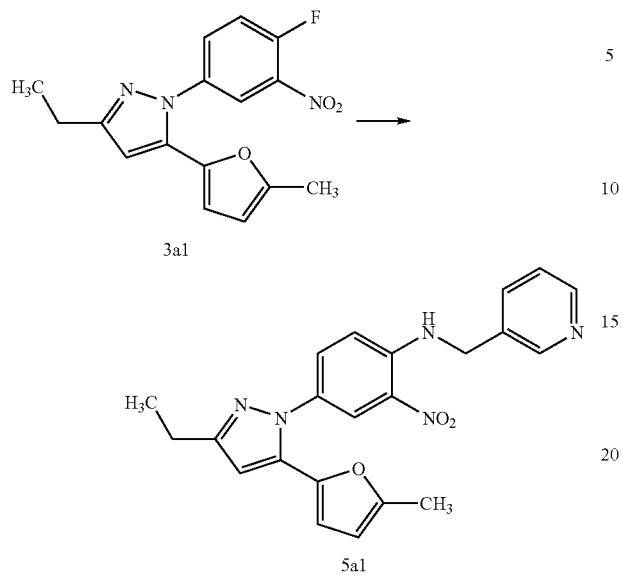

To a mixture of 3a1 (Example 3A) (534 mg, 1.69 mmol) and THF (10 mL) is added Et$_3$N (0.5 mL, 3.59 mmol) and 3-(aminomethyl)pyridine (0.5 mL, 4.9 mmol). The reaction mixture is stirred at room temperature for 16 h, diluted with EtOAc, washed with water and brine, dried over MgSO$_4$ and concentrated under reduced pressure. The residue is triturated with hexane to provide compound 5a1.

Other intermediates of formula V are prepared using the procedure of Example 5A, modified appropriately as is apparent to one skilled in the art. Suitable modifications of the procedure include but are not limited to using DMF as a solvent instead of THF and carrying out the reaction at temperatures of 50° C. to 80° C. rather than at room temperature.

Example 5B

Preparation of Intermediate 5b3

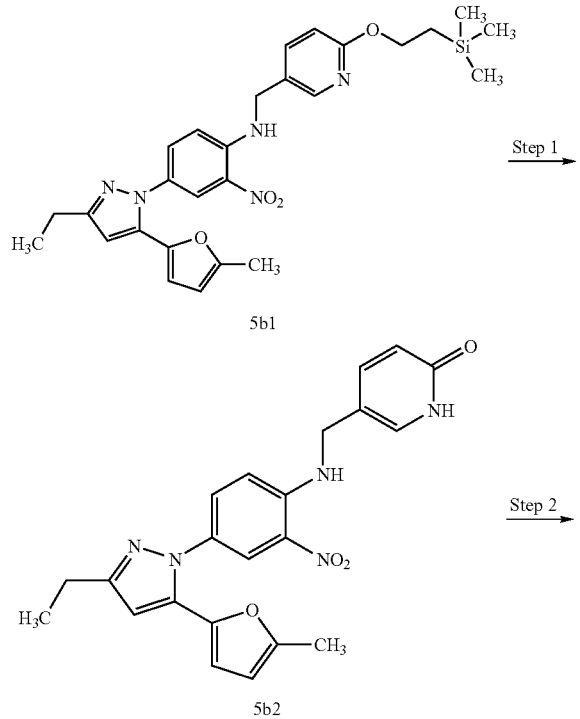

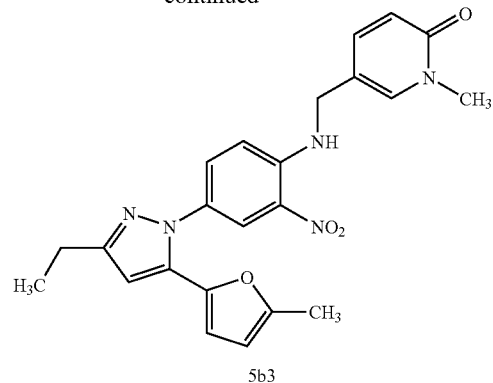

Step 1:

A mixture of compound 5b1 (prepared by a modification of the procedure of Example 5A, but replacing 3-(aminomethyl) pyridine with compound 4a3) (185 mg, 0.356 mmol) and AcOH (3 mL) is heated at 70° C. with stirring for 5 h. Concentration of the mixture under reduced pressure gives compound 5b2.

Step 2:

To a mixture of compound 5b2 (140 mg, 0.33 mmol) and DMF (3 mL) at room temperature is added K$_2$CO$_3$ (92 mg, 0.67 mmol) followed by CH$_3$I (42 µL, 0.67 mmol). The mixture is allowed to react at 40° C. overnight, then is diluted with saturated aqueous NaHCO$_3$ and extracted three times with EtOAc. The combined organic extract is washed with brine, dried (Na$_2$SO$_4$), filtered and concentrated under reduced pressure. The residue is purified by chromatography (20%-100% EtOAc/hexane) to give compound 5b3.

Example 6A

Preparation of Intermediate 6a1

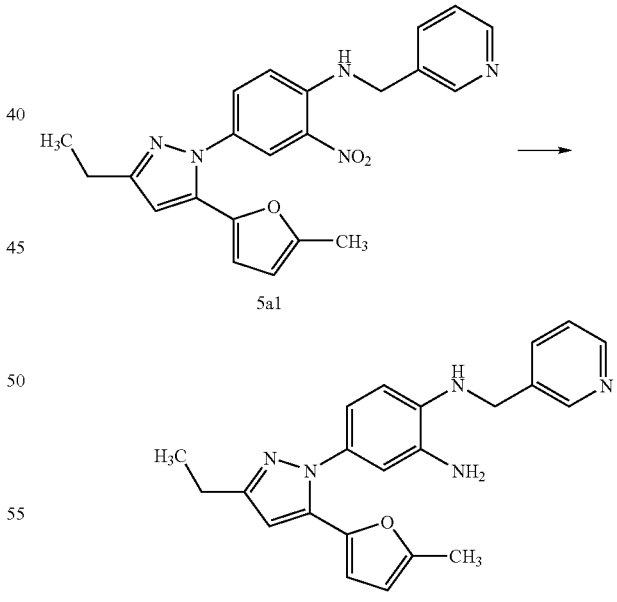

To a mixture of 5a1 (Example 5A) (678.4 mg, 1.68 mmol) and THF (10 mL) is added aqueous HCl (1 N, 10 mL) and Sn powder (797.6 mg, 6.72 mmol). The mixture is allowed to react for 1 h at room temperature, NaOH (10 mL) is added and the reaction is diluted with EtOAc, filtered through Celite™ and the layers are separated. The organic layer is washed with water and brine, dried over MgSO$_4$, filtered and concentrated under reduced pressure to provide compound 6a1.

Example 6B

Preparation of Intermediate 6b2

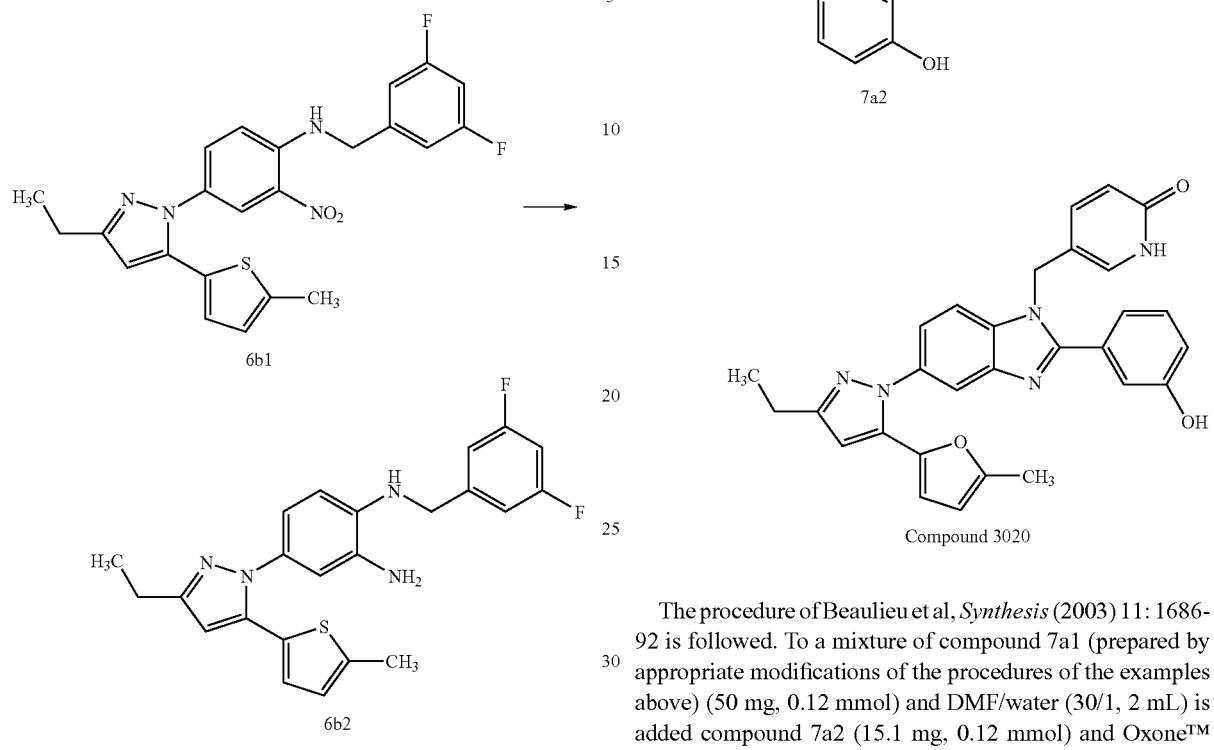

A mixture of compound 6b1 (prepared by appropriate modifications of the procedures of the examples above) (632 mg, 1.39 mmol), EtOH (20 mL), H$_2$O (2.0 mL) and Fe (311 mg, 5.56 mmol) is heated at reflux overnight with stirring. The mixture is cooled to room temperature and filtered through Celite™. The filtered solid is washed with EtOAc and the combined filtrate is contentrated under reduced pressure. The residue is diluted with saturated aqueous Na$_2$HCO$_3$ and extracted with EtOAc. The organic extract is washed with brine, dried (Na$_2$SO$_4$), filtered and concentrated under reduced pressure to provide compound 6b2.

Other intermediates of formula VI are prepared using the procedures of Examples 6A or 6B, modified appropriately as is apparent to one skilled in the art.

Example 7A

Preparation of Compound 3020, Table 3

The procedure of Beaulieu et al, *Synthesis* (2003) 11: 1686-92 is followed. To a mixture of compound 7a1 (prepared by appropriate modifications of the procedures of the examples above) (50 mg, 0.12 mmol) and DMF/water (30/1, 2 mL) is added compound 7a2 (15.1 mg, 0.12 mmol) and Oxone™ (2KHSO$_5$.KHSO$_4$.K$_2$SO$_4$) (45.7 mg, 0.07 mmol). The mixture is stirred for 2 h and diluted with saturated aqueous NaHCO$_3$. The resulting solid is collected by filtration and mixed with water (1 mL), and HBr/AcOH (48%, 1 mL) is added to the mixture. The mixture is heated at 100° C. overnight and evaporated to dryness, and the residue is purified by preparative HPLC to provide compound 3020 (Table 3).

Other compounds of formula I, or intermediates which may be further modified to prepare other compounds of formula I, are prepared using the procedure of Example 7A, modified appropriately as is apparent to one skilled in the art.

Example 8A

Preparation of Compound 3023, Table 3

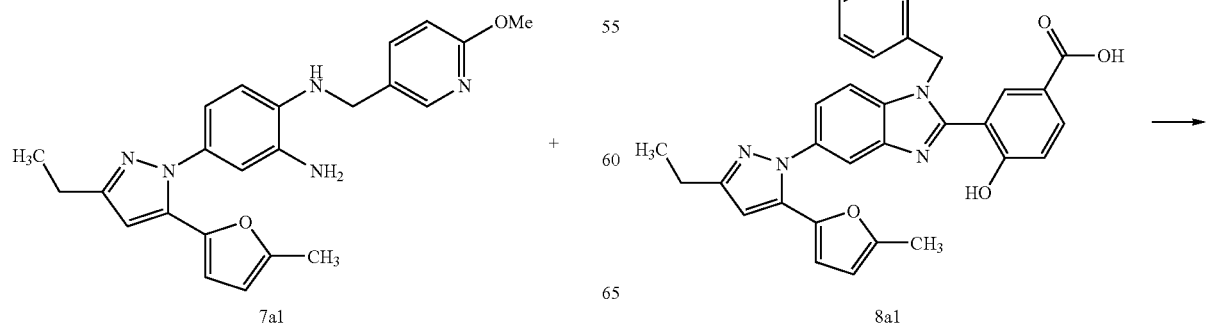

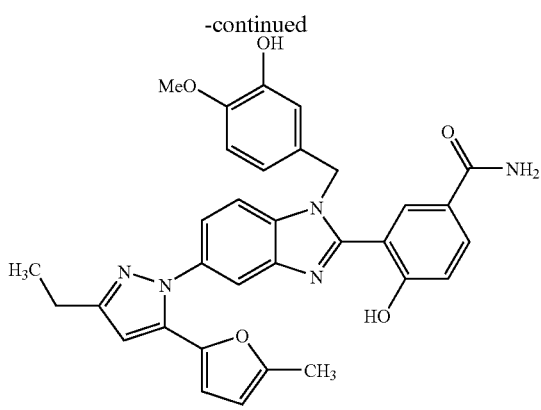

Compound 3023

To a mixture of compound 8a1 (prepared by appropriate modifications of the procedures of the examples above) (55 mg, 0.10 mmol) and DMF (2 mL) is added TBTU (38.5 mg, 0.12 mmol) and Et₃N (41.8 µL, 0.30 mmol). The mixture is allowed to react for 30 min, a solution of NH₃ in dioxane (0.5 M, 1.5 mL) is added and the reaction is stirred overnight. The mixture is purified by preparative HPLC to give compound 3023 (Table 3).

Example 8B

Preparation of Compound 5003, Table 5

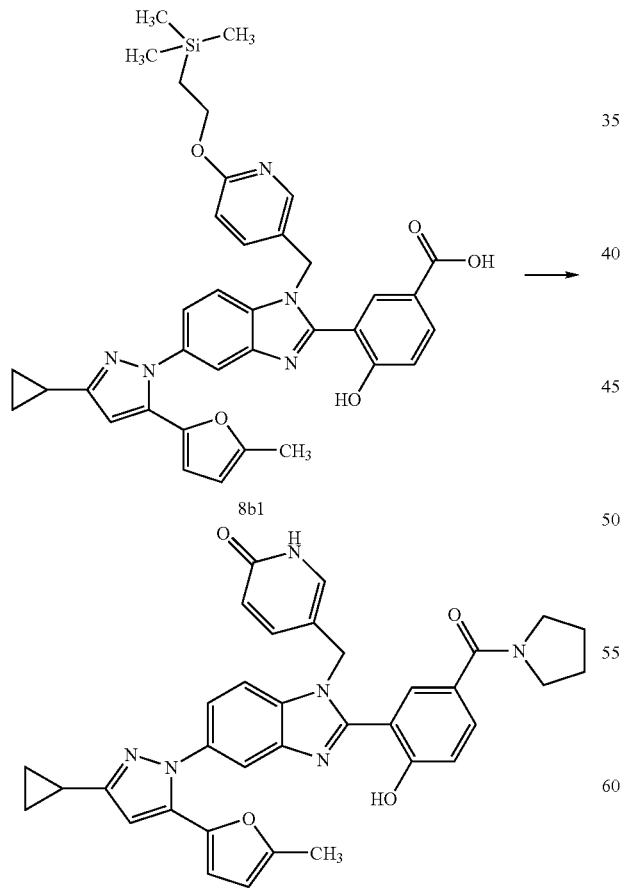

8b1

Compound 5003

To a mixture of compound 8b1 (prepared by appropriate modifications of the procedures of the examples above) (135 mg, 0.21 mmol) and DMF (2.5 mL) is added TBTU (86.8 mg, 0.27 mmol), Et₃N (60.8 µL, 0.44 mmol), and pyrrolidine (34.7 µL, 0.42 mmol). The mixture is allowed to react for 30 min, then is diluted with EtOAc, washed with water and brine, dried over MgSO₄, filtered and evaporated. The residue is diluted with AcOH (2 mL) and heated at 80° C. for 16 h. Purification by preparative HPLC gives compound 5003 (Table 5).

Example 8C

Preparation of Compound 3097, Table 3

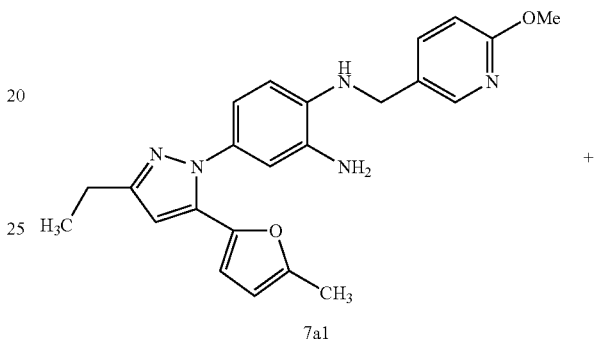

7a1

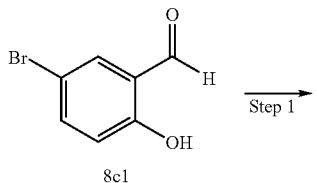

8c1

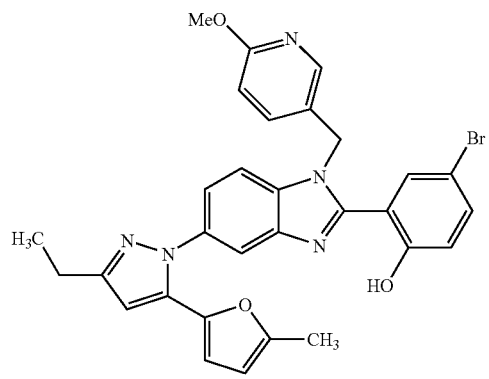

8c2

Step 2

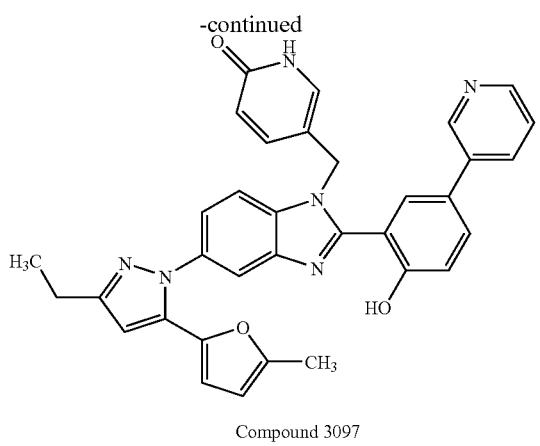

Compound 3097

Step 1:
To a mixture of compound 7a1 (Example 7A) (300 mg, 0.74 mmol) and DMF/water (30/1, 5 mL) is added aldehyde 8c1 (149.6 mg, 0.74 mmol) and Oxone™ (274.4 mg, 0.45 mmol). The reaction is stirred for 2 h then diluted with saturated aqueous $NaHCO_3$ and the resulting solid is filtered. The solid is mixed with EtOAc and the mixture is washed with saturated aqueous $NaHCO_3$ and brine, dried over $MgSO_4$, filtered and evaporated to provide compound 8c2.

Step 2:
A mixture of compound 8c2 (75 mg, 0.13 mmol), pyridine-3-boronic acid (20 mg, 0.16 mmol), Pd(tert-$Bu_3P)_2$ (6.54 mg, 0.01 mmol) and aqueous $Na_2CO_3$ (2 M, 0.5 mL) in DMF (2 mL) is heated in a microwave at 175° C. for 15 min. The mixture is cooled to room temperature and diluted with aqueous $NaHCO_3$. The resulting solid is collected by filtration and mixed with 48% HBr/AcOH (1 mL) and water (1 mL). The reaction mixture is heated overnight at 80° C. Purification by preparative HPLC gives compound 3097 (Table 3).

Example 8D

Preparation of Compound 4023, Table 4

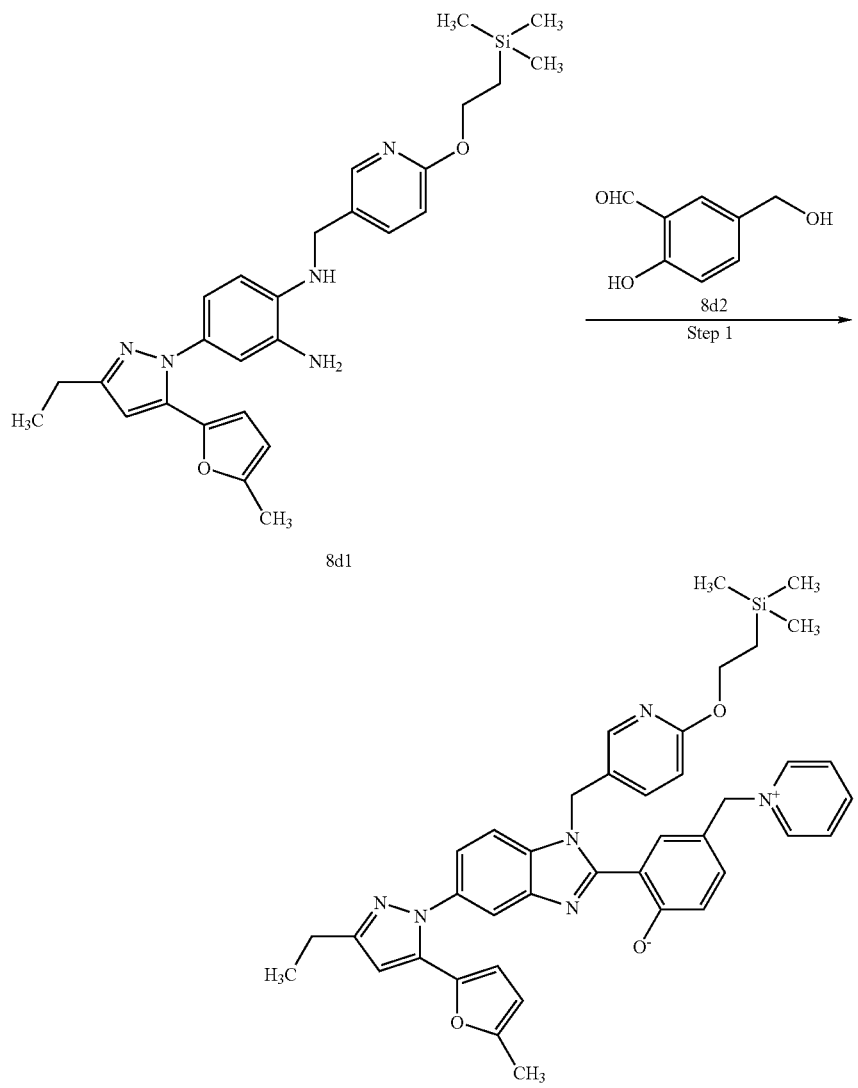

-continued

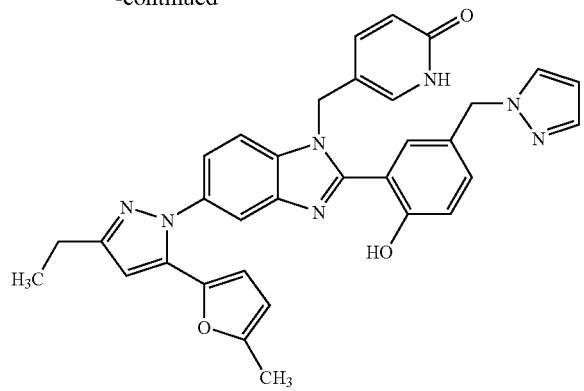

Compound 4023

Step 1:

To a mixture of compound 8d1 (1.06 g, 2.16 mmol) and pyridine (500 mL) is added aldehyde 8d2 (395 mg, 2.60 mmol). The mixture is stirred at 90° C. for 18 h, then is evaporated to dryness and diluted with EtOAc (250 mL). The mixture is extracted with water (2×100 mL) and the combined aqueous extract is lyophilized to afford compound 8d3.

Step 2:

A mixture of compound 8d3 (15 mg, 0.02 mmol), DMF (500 μL), pyrazole (1.6 mg, 0.024 mmol), and Cs$_2$CO$_3$ (10 mg, 0.3 mmole) is heated at 80° C. for 18 h on a JKEM™ reaction block (orbital shaker set at 270 rpm). The mixture is concentrated under reduced pressure, diluted with AcOH (500 μL) and heated at 80° C. for 2 h. Further AcOH is added to a total volume of 1.5 mL and the mixture is purified by semi-prep LCMS (Gemini column, 5 μm, 21.2 mm×50 mm, elution with a gradient of H$_2$O 0.06% TFA/MeCN 0.06% TFA) to afford compound 4023 (Table 4).

Example 9A

Preparation of Intermediate 9a6

Step 1:

A mixture of compound 9a1 (10 g, 64 mmol) and CH$_3$NH$_2$ in THF (1M, 80 mL, 80 mmol) is heated at 120° C. for 48 h. The reaction mixture is concentrated to dryness, and diluted with EtOAc. The resulting solid is filtered to provide compound 9a2.

Step 2:

To a mixture of compound 9a2 (1.5 g, 8.97 mmol) and DMF/water (30/1, 31 mL) is added compound 9a3 (1.18 g, 8.97 mmol) and Oxone™ (2KHSO$_5$.KHSO$_4$.K$_2$SO$_4$) (3.31 g, 5.4 mmol). The mixture is stirred for 2 h and diluted with saturated aqueous NaHCO$_3$. The resulting solid is collected by filtration to provide compound 9a4.

Step 3:

A mixture of compound 9a4 (2.3 g, 8.27 mmol), EtOH (25 mL), H$_2$O (4.0 mL) and Fe (1.89 g, 33.9 mmol) is heated at reflux overnight with stirring. The mixture is cooled to room temperature and filtered through Celite™. The filtered solid is washed with EtOAc and the combined filtrate is contentrated under reduced pressure. The residue is diluted with saturated aqueous NaHCO$_3$ and extracted with EtOAc. The organic

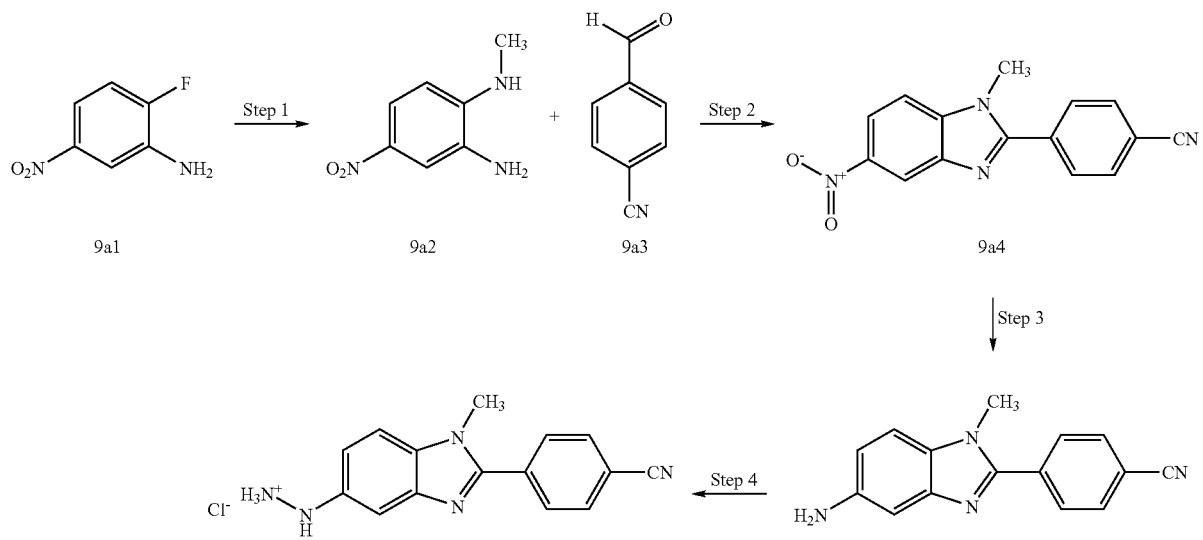

extract is washed with brine, dried (Na$_2$SO$_4$), filtered and concentrated under reduced pressure to provide compound 9a5.

Step 4:

A mixture of compound 9a5 (500 mg, 2.01 mmol) and aqueous HCl (12 M, 5 mL) is stirred at 0° C. and a mixture of NaNO$_2$ (132.9 mg, 2.01 mmol) in H$_2$O (1.5 mL) is added drop wise. The resulting solution is stirred for 10 min and a mixture of SnCl$_2$ (1.0 g, 4.43 mmol) and HCl (12M, 1.5 mL) is added dropwise. After 30 min the resulting solid is filtered and dried under reduced pressure to provide compound 9a6.

Intermediate 9a6 may be transformed to intermediates of formula XI by reactions well known in the art, and other intermediates of formula XI may be prepared using the procedure of Example 9a, appropriately modified as is apparent to one skilled in the art. Intermediates of formula XI may be transformed to compounds of formula (I) using the procedures of Examples 3A or 3B, modified appropriately as is known in the art.

Example 10

C8166 HIV-1 Luciferase Assay (EC$_{50}$)

The assay used to measure inhibition of HIV replication is as described in WO 2004/050643, pages 73-75, with the following modifications:

Preparation of Compounds

Serial dilutions of HIV-1 inhibitors are prepared in complete media from DMSO stock solutions. Eleven serial dilutions of desired concentration are prepared in a 1 mL deep well titer plate (96 wells). The 12$^{th}$ well contains complete media with no inhibitor and serves as the positive control. All samples contain the same concentration of DMSO ($\leq$0.1% DMSO). Inhibitor is added, to triplicate wells, of a 96 well tissue culture treated clear view black microtiter plate (Corning Costar catalogue #3904). The total volume per well is 200 μL of media containing the cells and inhibitor. The last row is reserved for uninfected C8166 LTRIuc cells to serve as the background blank control and the first row is media alone.

Infection of Cells

Count C8166 LTRIuc cells and place in a minimal volume of complete RPMI 1640 in a tissue culture flask (ex. 30×10$^6$ cells in 10 mL media/25 cm$^2$ flask). Infect cells with HIV-1 at a moi of 0.005. Incubate cells for 1.5 hours at 37° C. on a rotating rack in a 5% CO$_2$ incubator. Resuspend cells in complete RPMI to give a final concentration of 25,000-cells/well. Add cells to wells of 96 well microtiter plate containing inhibitors. Add 25,000 uninfected C8166-LTRIuc cells/well in 200 μL complete RPMI to last row for background control. Incubate cells at 37° C. in 5% CO$_2$ incubator for 3 days.

Tables of Compounds

The following tables list compounds representative of the invention. Representative compounds listed in Tables 1 to 5 below show EC$_{50}$ values below 10 μM when tested in the assay of Example 10.

Retention times ($t_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

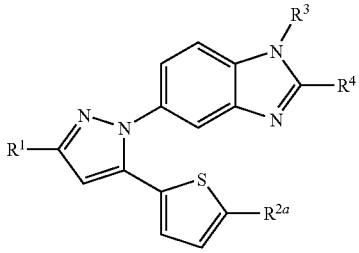

| Cpd | R$^1$ | R$^{2a}$ | R$^3$ | R$^4$ | $t_R$ (min) | MS (M + H)$^+$ |
|---|---|---|---|---|---|---|
| 1001 | Et | Br | 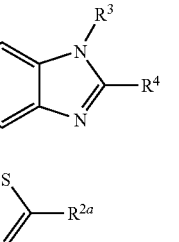 | 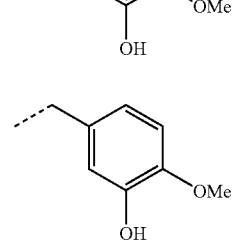 | 5.7 | 602.0 604.0 |
| 1002 | Et | H | 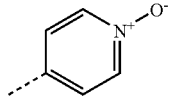 | 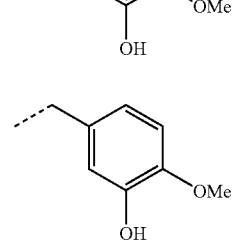 | 5.0 | 524.1 |

TABLE 1-continued

| Cpd | R¹ | R²ᵃ | R³ | R⁴ | $t_R$ (min) | MS (M + H)⁺ |
|---|---|---|---|---|---|---|
| 1003 | Et | Br | 3-hydroxy-4-methoxybenzyl | 4-carbamoylphenyl | 5.3 | 628, 630 |
| 1004 | Et | H | 4-methoxybenzyl | 4-carboxyphenyl | 5.5 | 535.1 |
| 1005 | Et | H | 2-chlorobenzyl | 4-carboxyphenyl | 5.9 | 537.0, 539.0 |
| 1006 | Et | H | (6-oxo-1,6-dihydropyridin-3-yl)methyl | 2-hydroxyphenyl | 3.9 | 494.1 |
| 1007 | Et | Me | 3-hydroxy-4-methoxybenzyl | 4-hydroxy-3-(N,N-dimethylcarbamoyl)phenyl | 5.4 | 608.4 |
| 1008 | Et | Me | (6-oxo-1,6-dihydropyridin-3-yl)methyl | 2-hydroxyphenyl | 4.8 | 508.1 |
| 1009 | Et | H | 3-hydroxy-4-methoxybenzyl | 4-hydroxy-3-{[4-(2-hydroxyethyl)piperazin-1-yl]carbonyl}phenyl | 4.5 | 679.2 |
| 1010 | Et | Me | 3-hydroxy-4-methoxybenzyl | 4-hydroxy-3-{[4-(2-hydroxyethyl)piperazin-1-yl]carbonyl}phenyl | 4.9 | 693.2 |

TABLE 1-continued
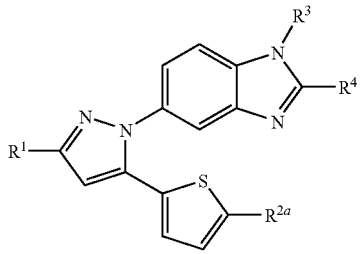
| Cpd | R¹ | R²ᵃ | R³ | R⁴ | $t_R$ (min) | MS $(M + H)^+$ |
|---|---|---|---|---|---|---|
| 1011 | Et | H | 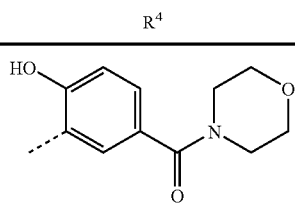 | 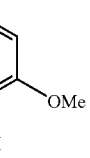 | 5.1 | 636.1 |
| 1012 | Et | H | 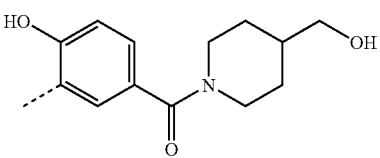 | 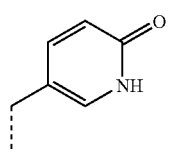 | 5.0 | 664.2 |
| 1013 | Me | H | 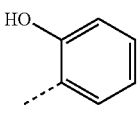 | 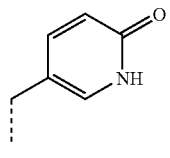 | 4.1 | 480.0 |
| 1014 | Me | H | 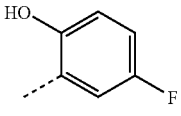 | 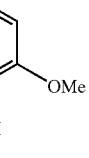 | 4.3 | 498.0 |
| 1015 | Me | H | 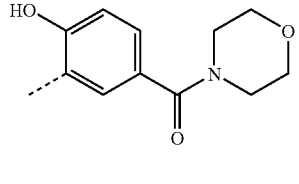 | 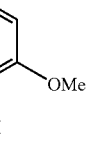 | 4.7 | 622.2 |
| 1016 | Me | H | 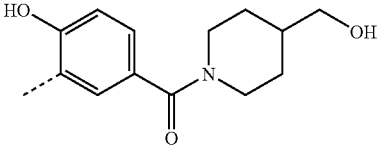 | 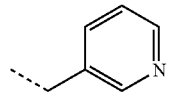 | 4.7 | 650.2 |
| 1017 | Et | Br | 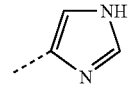 | 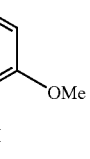 | 4.7 | 531.0 / 533.0 |
| 1018 | Et | H | 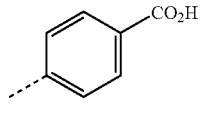 | | 5.6 | 551.1 |

TABLE 1-continued

| Cpd | R¹ | R²ᵃ | R³ | R⁴ | $t_R$ (min) | MS (M + H)⁺ |
|---|---|---|---|---|---|---|
| 1019 | Et | Br | 3-OH-4-OMe-benzyl | 4-CO₂H-phenyl | 6.3 | 631.0 633.0 |

TABLE 2

| Cpd | R¹ | R²ᵃ | R³ | R⁴ | $t_R$ (min) | MS (M + H)⁺ |
|---|---|---|---|---|---|---|
| 2001 | Et | Br | pyridin-3-ylmethyl | pyridine N-oxide-4-yl | 3.4 | 541.0 543.0 |
| 2002 | Et | Br | 4-OMe-benzyl | pyridine N-oxide-4-yl | 4.4 | 570.0 572.0 |
| 2003 | Et | Br | 2-Cl-benzyl | pyridine N-oxide-4-yl | 4.1 | 574.0 576.0 |
| 2004 | Et | Br | 3-OH-4-OMe-benzyl | pyridine N-oxide-4-yl | 4.0 | 586.0 588.0 |
| 2005 | Et | Br | pyridin-3-ylmethyl | 4-CO₂H-phenyl | 3.5 | 568.0 570.0 |

TABLE 2-continued
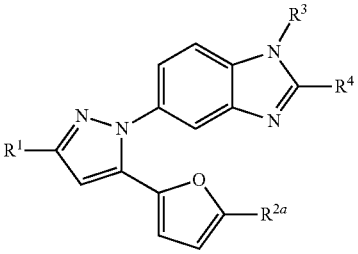
| Cpd | R¹ | R²ᵃ | R³ | R⁴ | $t_R$ (min) | MS $(M+H)^+$ |
|---|---|---|---|---|---|---|
| 2006 | Et | Br | 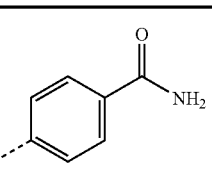 | 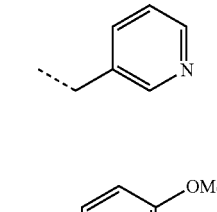 | 4.8 | 567.0 569.0 |
| 2007 | Et | CF₃ | 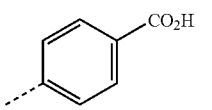 | 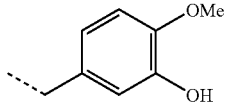 | 5.5 | 603.1 |
| 2008 | Et | CF₃ | 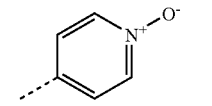 | 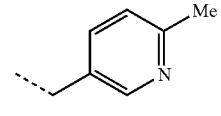 | 5.6 | 576.1 |
| 2009 | Et | CF₃ | 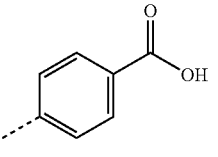 | 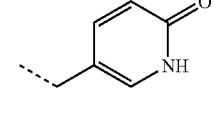 | 4.7 | 572.1 |
| 2010 | Et | CF₃ | 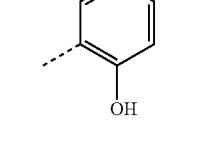 | 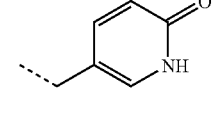 | 4.5 | 546.2 |
| 2011 | Et | Br | 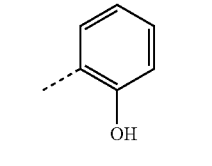 | 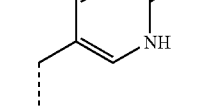 | 4.9 | 557.1 559.1 |
| 2012 | Et | H | 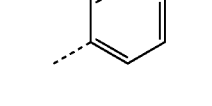 | 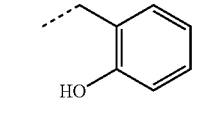 | 4.3 | 478.1 |
| 2013 | Me | Me | 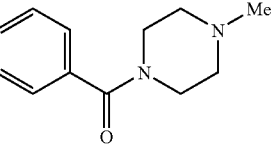 | | 4.4 | 603.2 |

TABLE 2-continued

[Structure: pyrazole-benzimidazole-furan core with R¹ on pyrazole, R²ᵃ on furan, R³ on benzimidazole N, R⁴ on benzimidazole C2]

| Cpd | R¹ | R²ᵃ | R³ | R⁴ | $t_R$ (min) | MS $(M+H)^+$ |
|---|---|---|---|---|---|---|
| 2014 | Me | Me | 3-hydroxybenzyl | 4-hydroxy-3-methyl-(4-methylpiperazin-1-yl)carbonyl phenyl | 4.3 | 603.2 |
| 2015 | Et | CF₃ | (6-oxo-1,6-dihydropyridin-3-yl)methyl | 5-fluoro-2-hydroxyphenyl | 5.4 | 564.1 |
| 2016 | Et | CF₃ | (6-oxo-1,6-dihydropyridin-3-yl)methyl | 2-hydroxy-4-methylphenyl | 5.3 | 560.2 |
| 2017 | Me | Me | (6-oxo-1,6-dihydropyridin-3-yl)methyl | 2-hydroxyphenyl | 4.2 | 478.1 |
| 2018 | Me | Me | (6-oxo-1,6-dihydropyridin-3-yl)methyl | 4-fluoro-2-hydroxyphenyl | 4.5 | 496.1 |
| 2019 | Et | Br | (6-oxo-1,6-dihydropyridin-3-yl)methyl | 4-fluoro-2-hydroxyphenyl | 5.1 | 575.1, 577.1 |
| 2020 | Et | Cl | 3-hydroxy-4-methoxybenzyl | 4-hydroxy-3-methyl-[4-(2-hydroxyethyl)piperazin-1-yl]carbonyl phenyl | 4.8 | 697.1, 699.1 |
| 2021 | Et | CF₃ | 3-hydroxy-4-methoxybenzyl | 4-hydroxy-3-(morpholin-4-ylcarbonyl)phenyl | 5.6 | 688.1 |

TABLE 2-continued
| Cpd | R¹ | R²ᵃ | R³ | R⁴ | t_R (min) | MS (M + H)⁺ |
|---|---|---|---|---|---|---|
| 2022 | Et | Cl | 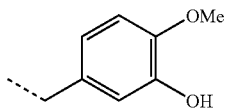 | 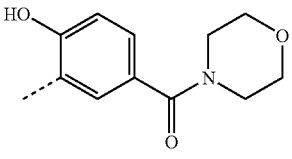 | 5.4 | 655.1 657.1 |
| 2023 | Et | Cl | 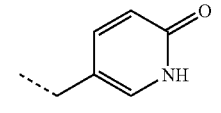 | 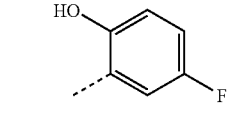 | 4.9 | 530.0 532.0 |
| 2024 | Me | Me | 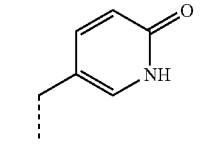 | 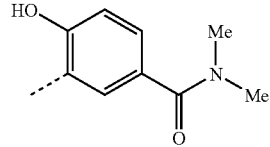 | 4.2 | 549.1 |
| 2025 | Et | CF₃ | 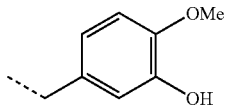 | 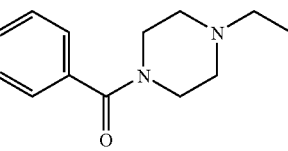 | 5.0 | 731.1 |
| 2026 | Et | Cl | 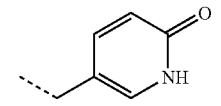 | 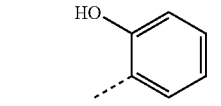 | 4.8 | 512.1 514.1 |
| 2027 | Et | CF₃ | 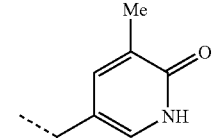 | 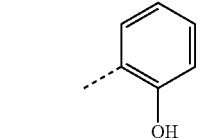 | 5.2 | 560.1 |
| 2028 | Et | CF₃ | 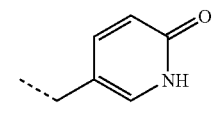 | 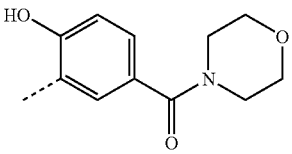 | 5.0 | 659.1 |
| 2029 | Et | CF₃ | 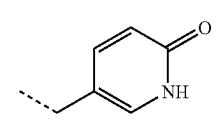 | 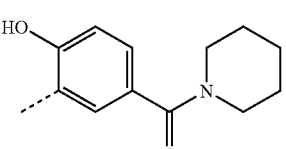 | 5.4 | 657.2 |

TABLE 2-continued

| Cpd | R¹ | R²ᵃ | R³ | R⁴ | $t_R$ (min) | MS $(M + H)^+$ |
|---|---|---|---|---|---|---|
| 2030 | Et | CF₃ | 5-(2-oxo-1,2-dihydropyridin-5-yl)methyl | 4-hydroxy-3-(pyrrolidin-1-ylcarbonyl)phenyl | 5.2 | 643.2 |
| 2031 | Et | CF₃ | 3-methyl-2-oxo-1,2-dihydropyridin-5-yl-methyl | 2-hydroxy-5-fluorophenyl | 5.5 | 578.1 |
| 2032 | Et | CF₃ | 1-(tetramethylguanidinium)-2-oxo-1,2-dihydropyridin-5-ylmethyl | 4-hydroxy-3-(morpholin-4-ylcarbonyl)phenyl | 5.0 | 757.3 |
| 2033 | Et | Cl | 2-oxo-1,2-dihydropyridin-5-ylmethyl | 4-hydroxy-3-(morpholin-4-ylcarbonyl)phenyl | 4.8 | 626.2, 628.2 |
| 2034 | Et | CF₃ | 3-methyl-2-oxo-1,2-dihydropyridin-5-ylmethyl | 4-hydroxy-3-(N,N-dimethylcarbamoyl)phenyl | 5.1 | 631.2 |
| 2035 | Et | Cl | pyridin-3-ylmethyl | 4-hydroxy-3-(morpholin-4-ylcarbonyl)phenyl | 4.6 | 609.3, 611.3 |
| 2036 | Et | Cl | pyridin-3-ylmethyl | 4-hydroxy-3-(piperidin-1-ylcarbonyl)phenyl | 5.0 | 607.3, 609.3 |

TABLE 2-continued

| Cpd | R¹ | R²ᵃ | R³ | R⁴ | t_R (min) | MS (M + H)⁺ |
|-----|----|----|----|----|-----------|-------------|
| 2037 | Et | CF₃ | 3-pyridyl | 4-hydroxy-3-(morpholine-4-carbonyl)phenyl | 4.9 | 643.2 |
| 2038 | Et | CF₃ | 3-pyridyl | 4-hydroxy-3-(piperidine-1-carbonyl)phenyl | 5.3 | 641.3 |
| 2039 | Et | Cl | 2-oxo-1,2-dihydropyridin-5-yl | 4-hydroxy-3-[N-isopropyl-N-methylcarbamoyl]phenyl | 5.0 | 611.3, 613.3 |
| 2040 | Et | CF₃ | 3-methyl-2-oxo-1,2-dihydropyridin-5-yl | 4-hydroxy-3-(pyrrolidine-1-carbonyl)phenyl | 5.3 | 657.3 |
| 2041 | Et | Cl | 2-oxo-1,2-dihydropyridin-5-yl | 4-hydroxy-3-(pyrrolidine-1-carbonyl)phenyl | 4.9 | 609.2, 611.2 |
| 2042 | Et | CF₃ | 3-methyl-2-oxo-1,2-dihydropyridin-5-yl | 4-hydroxy-3-(piperidine-1-carbonyl)phenyl | 5.5 | 671.3 |
| 2043 | Et | Cl | 2-oxo-1,2-dihydropyridin-5-yl | 4-hydroxy-3-(piperidine-1-carbonyl)phenyl | 5.2 | 623.2, 625.2 |
| 2044 | Et | Cl | 2-oxo-1,2-dihydropyridin-5-yl | 4-hydroxy-3-(N,N-dimethylcarbamoyl)phenyl | 4.8 | 583.2, 585.2 |

TABLE 2-continued

| Cpd | R¹ | R²ᵃ | R³ | R⁴ | t_R (min) | MS (M + H)⁺ |
|---|---|---|---|---|---|---|
| 2045 | Et | Cl | 4-pyridyl | 4-hydroxy-3-(piperidin-1-ylcarbonyl)phenyl | 5.0 | 607.3, 609.3 |
| 2046 | Et | CF₃ | 2-oxo-1,2-dihydropyridin-5-yl | 4-hydroxy-3-(azetidin-1-ylcarbonyl)phenyl | 5.1 | 629.2 |
| 2047 | Et | CF₃ | 2-oxo-1,2-dihydropyridin-5-yl | 4-hydroxy-3-(N,N-dimethylcarbamoyl)phenyl | 5.0 | 617.2 |
| 2048 | Et | CF₃ | 2-oxo-1,2-dihydropyridin-5-yl | 4-hydroxy-3-(N-cyclopentyl-N-methylcarbamoyl)phenyl | 5.6 | 671.3 |
| 2049 | Et | CF₃ | 6-methoxypyridin-3-yl | 4-hydroxy-3-(pyrrolidin-1-ylcarbonyl)phenyl | 6.1 | 657.2 |
| 2050 | Et | CF₃ | 6-methoxypyridin-3-yl | 4-hydroxy-3-(morpholin-4-ylcarbonyl)phenyl | 5.9 | 673.3 |
| 2051 | Et | Cl | 3-pyridyl | 4-hydroxy-3-(pyrrolidin-1-ylcarbonyl)phenyl | 4.9 | 593.2, 595.2 |

TABLE 2-continued

| Cpd | R¹ | R²ᵃ | R³ | R⁴ | t_R (min) | MS (M + H)⁺ |
|---|---|---|---|---|---|---|
| 2052 | Et | Cl | 3-pyridylmethyl | 4-hydroxy-3-[(3-hydroxypyrrolidin-1-yl)carbonyl]phenyl | 4.4 | 609.2 611.2 |
| 2053 | Et | Cl | cyclopropylmethyl | 4-hydroxy-3-(pyrrolidin-1-ylcarbonyl)phenyl | 5.6 | 556.2 558.2 |
| 2054 | Et | Cl | cyclopropylmethyl | 4-hydroxy-3-(morpholin-4-ylcarbonyl)phenyl | 5.4 | 572.2 574.2 |
| 2055 | Et | Cl | 3-hydroxy-4-methoxybenzyl | 4-hydroxy-3-(pyrrolidin-1-ylcarbonyl)phenyl | 5.6 | 638.3 640.3 |
| 2056 | Et | Cl | (6-oxo-1,6-dihydropyridin-3-yl)methyl | 4-hydroxy-3-{[4-(hydroxymethyl)piperidin-1-yl]carbonyl}phenyl | 4.7 | 653.2 655.2 |
| 2057 | Et | Cl | (6-oxo-1,6-dihydropyridin-3-yl)methyl | 4-hydroxy-3-[(4-fluoropiperidin-1-yl)carbonyl]phenyl | 5.0 | 641.2 643.2 |
| 2058 | Et | Cl | (6-oxo-1,6-dihydropyridin-3-yl)methyl | 4-hydroxy-3-[(4-hydroxypiperidin-1-yl)carbonyl]phenyl | 4.5 | 639.2 641.1 |

TABLE 2-continued
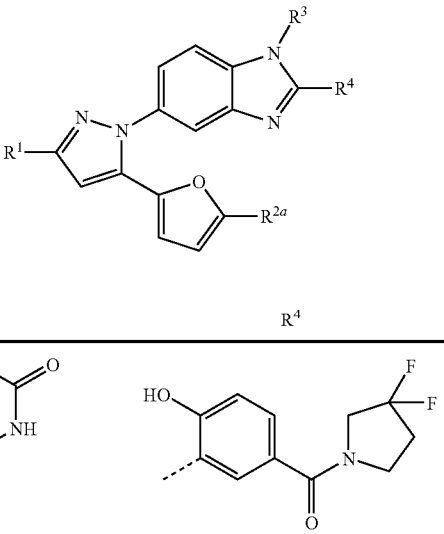
| Cpd | R¹ | R²ᵃ | R³ | R⁴ | $t_R$ (min) | MS $(M + H)^+$ |
|---|---|---|---|---|---|---|
| 2059 | Et | Cl | 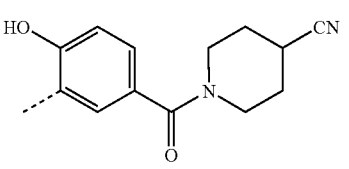 | 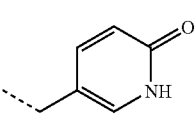 | 5.2 | 645.2 647.2 |
| 2060 | Et | Cl | 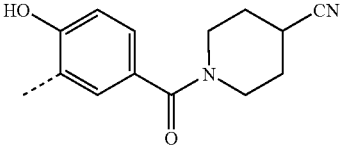 | 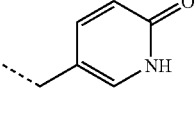 | 4.9 | 646.2 648.2 (M − H)⁻ |
| 2061 | Et | Cl | 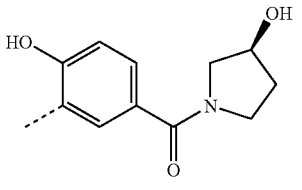 | 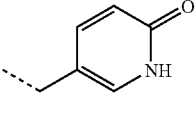 | 4.5 | 623.2 625.2 (M − H)⁻ |
| 2062 | Et | Cl | 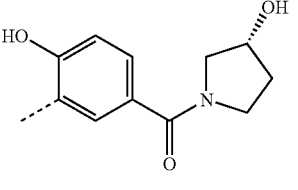 | 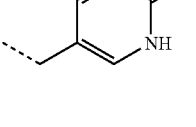 | 4.5 | 623.1 624.2 (M − H)⁻ |
| 2063 | Et | Cl | 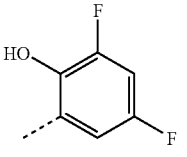 | 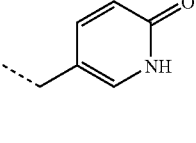 | 5.2 | 548.1 550.1 |
| 2064 | Et | Cl | 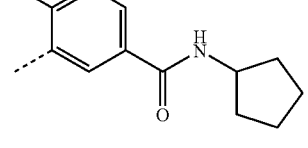 | 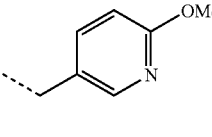 | 5.3 | 623.2 625.2 |
| 2065 | Et | CF₃ | 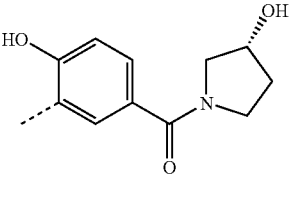 | 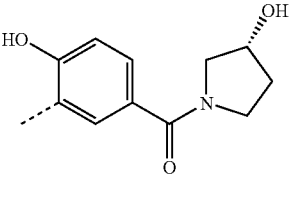 | 5.6 | 673.2 |

TABLE 2-continued

| Cpd | R[1] | R[2a] | R[3] | R[4] | $t_R$ (min) | MS (M + H)[+] |
|---|---|---|---|---|---|---|
| 2066 | Et | Cl | 5-(pyridin-2(1H)-one-yl) | 3-hydroxy-4-(pyrrolidin-1-ylcarbonyl)phenyl | 4.9 | 609.2 611.2 |
| 2067 | Et | Cl | pyridin-3-yl | 4-hydroxy-3-(pyrrolidin-1-ylcarbonyl)phenyl | 4.7 | 608.2 610.2 |
| 2068 | Et | CF$_3$ | pyridin-3-yl | 4-hydroxy-3-((3-hydroxypyrrolidin-1-yl)carbonyl)phenyl | 4.7 | 643.2 |
| 2069 | Et | CF$_3$ | pyridin-3-yl | 4-hydroxy-3-(N-methyl-N-(2-methoxyethyl)carbamoyl)phenyl | 5.0 | 645.2 |
| 2070 | Et | Cl | 5-(pyridin-2(1H)-one-yl) | 3-acetyl-4-hydroxyphenyl | 4.9 | 554.1 556.1 |
| 2071 | Et | Cl | 3-methyl-2-methoxypyridin-5-yl | 4-hydroxy-3-(pyrrolidin-1-ylcarbonyl)phenyl | 6.3 | 637.1 639.1 |
| 2072 | Et | Cl | cyclopropylmethyl | 4-hydroxy-3-((3-hydroxypyrrolidin-1-yl)carbonyl)phenyl | 5.3 | 572.1 574.1 |

TABLE 2-continued

| Cpd | R¹ | R²ᵃ | R³ | R⁴ | t_R (min) | MS (M + H)⁺ |
|---|---|---|---|---|---|---|
| 2073 | Et | Cl | cyclopropylmethyl | 4-hydroxy-3-methyl-benzoyl-(3-hydroxy)pyrrolidine | 5.3 | 572.2, 574.2 |
| 2074 | Et | Cl | cyclopropylmethyl | 4-hydroxy-3-methyl-benzoyl-(2-methyl)pyrrolidine | 6.1 | 570.2, 572.2 |
| 2075 | Et | Cl | cyclopropylmethyl | 4-hydroxy-3-methyl-benzoyl-(3-dimethylamino)pyrrolidine | 4.9 | 599.2, 601.2 |
| 2076 | Et | Cl | cyclopropylmethyl | 4-hydroxy-3-methyl-benzoyl-(4-isopropyl)piperazine | 5.1 | 613.2, 615.2 |
| 2077 | Et | Cl | (1-methyl-1H-imidazol-5-yl)methyl | 4-hydroxy-3-methyl-benzoyl-pyrrolidine | 4.9 | 596.2, 598.2 |
| 2078 | Et | CF₃ | (6-methoxypyridin-3-yl)methyl | 4-hydroxy-3-methyl-benzoyl-(piperidine-4-carboxylic acid) | 5.6 | 715.1 |

TABLE 3
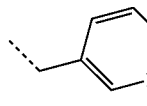
| Cpd | R³ | R⁴ | $t_R$ (min) | MS (M + H)⁺ |
|---|---|---|---|---|
| 3001 | 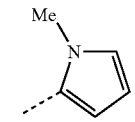 | 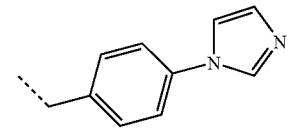 | 4.3 | 463.2 |
| 3002 | 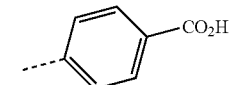 | 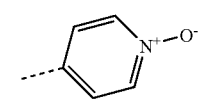 | 4.5 | 569.2 |
| 3003 | Et | 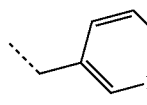 | 4.8 | 414.1 |
| 3004 | 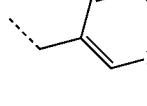 | —CH₂OH | 4.0 | 414.2 |
| 3005 | 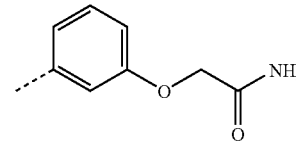 | 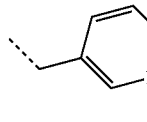 | 4.5 | 533.2 |
| 3006 | 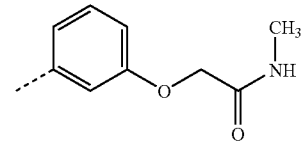 | 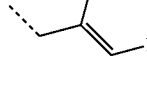 | 4.6 | 547.2 |
| 3007 | 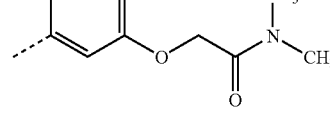 | 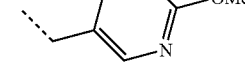 | 4.7 | 561.2 |
| 3008 | 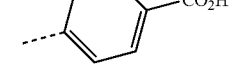 | 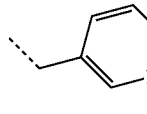 | 5.2 | 534.2 |
| 3009 | 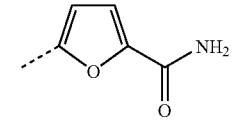 | | 4.6 | 493.2 |

TABLE 3-continued

[Core structure: 1-ethyl-pyrazole substituted with 5-methylfuran and linked to a benzimidazole bearing R³ and R⁴ substituents]

| Cpd | R³ | R⁴ | $t_R$ (min) | MS $(M+H)^+$ |
|---|---|---|---|---|
| 3010 | 3-pyridylmethyl | 4-(C(O)NH₂)-phenyl | 4.4 | 503.1 |
| 3011 | cyclopropyl | 4-CO₂H-phenyl | 5.0 | 467.1 |
| 3012 | 4-OMe-3-OH-benzyl | 4-(C(O)NHMe)-phenyl | 5.3 | 562.1 |
| 3013 | 4-OMe-3-OH-benzyl | 3-(C(O)NH₂)-phenyl | 5.2 | 548.2 |
| 3014 | 4-NH₂-benzyl | 4-CO₂H-phenyl | 4.6 | 518.1 |
| 3015 | 4-N₃-benzyl | 4-CO₂H-phenyl | 6.5 | 544.0 |
| 3016 | 3-(NHAc)-benzyl | 4-pyridyl N-oxide | 5.0 | 533.1 |
| 3017 | (2-oxo-1,2-dihydropyridin-5-yl)methyl | phenyl | 4.2 | 476.1 |
| 3018 | (2-methoxypyridin-4-yl)methyl | 4-CO₂H-phenyl | 5.2 | 534.1 |
| 3019 | (2-oxo-1,2-dihydropyridin-5-yl)methyl | 4-OH-phenyl | 4.0 | 492.1 |

TABLE 3-continued

[Structure: ethyl-pyrazole linked to benzimidazole bearing R³ on N and R⁴ at 2-position, with 5-methylfuran substituent]

| Cpd | R³ | R⁴ | t_R (min) | MS (M + H)⁺ |
|---|---|---|---|---|
| 3020 | 5-(2-oxo-1H-pyridinyl)methyl | 3-hydroxyphenyl | 4.1 | 492.1 |
| 3021 | (6-methoxypyridin-3-yl)methyl | 4-hydroxy-3-carboxyphenyl | 4.8 | 550.1 |
| 3022 | (4-methoxy-3-hydroxyphenyl)methyl | 4-hydroxy-3-(N-methylcarbamoyl)phenyl | 5.1 | 578.1 |
| 3023 | (4-methoxy-3-hydroxyphenyl)methyl | 4-hydroxy-3-carbamoylphenyl | 5.0 | 564.1 |
| 3024 | (4-methoxy-3-hydroxyphenyl)methyl | 4-hydroxy-3-(N,N-dimethylcarbamoyl)phenyl | 5.2 | 592.1 |
| 3025 | 5-(2-oxo-1H-pyridinyl)methyl | 2-hydroxyphenyl | 4.1 | 492.1 |
| 3026 | (6-methylpyridin-3-yl)methyl | 4-carboxyphenyl | 4.2 | 518.1 |

TABLE 3-continued
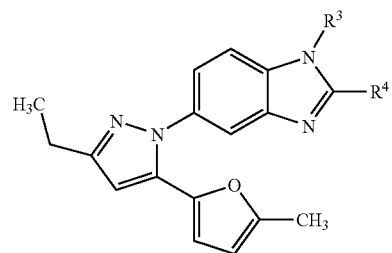
| Cpd | R³ | R⁴ | $t_R$ (min) | MS (M + H)⁺ |
|---|---|---|---|---|
| 3027 | 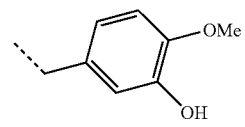 | 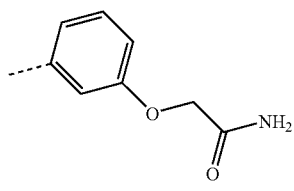 | 5.2 | 578.2 |
| 3028 | 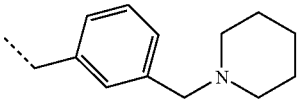 | 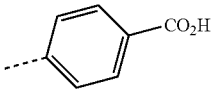 | 4.6 | 600.2 |
| 3029 | 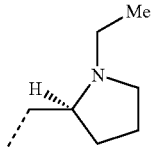 | 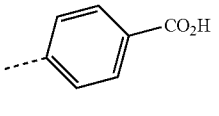 | 4.3 | 524.2 |
| 3030 | 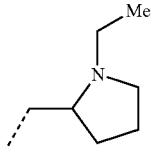 | 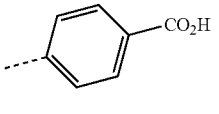 | 4.4 | 524.2 |
| 3031 | Et | 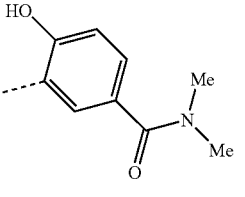 | 5.0 | 484.2 |
| 3032 | 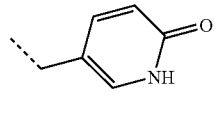 | 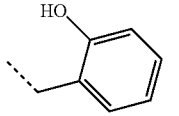 | 4.1 | 506.2 |
| 3033 | 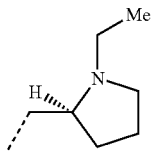 | 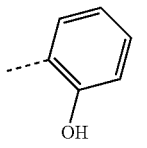 | 4.4 | 496.3 |
| 3034 | 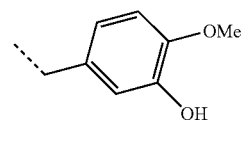 | 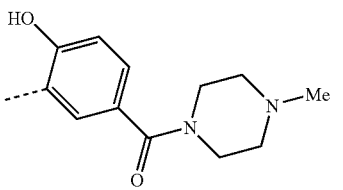 | 4.7 | 647.3 |

TABLE 3-continued

| Cpd | R³ | R⁴ | t_R (min) | MS (M + H)⁺ |
|---|---|---|---|---|
| 3035 | Et | 4-hydroxy-3-yl benzamide | 4.7 | 456.2 |
| 3036 | 5-yl-pyridin-2(1H)-one | cyclopropyl | 4.0 | 454.2 |
| 3037 | 4-methoxy-3-hydroxyphenyl | 4-hydroxy-3-yl (morpholin-4-yl)carbonyl phenyl | 5.2 | 634.3 |
| 3038 | 5-yl-pyridin-2(1H)-one | 4-hydroxy-3-yl N-methylbenzamide | 4.4 | 549.2 |
| 3039 | 6-methyl-5-yl-pyridin-2(1H)-one | 2-hydroxyphenyl | 4.1 | 506.2 |
| 3040 | 5-yl-pyridin-2(1H)-one | 2-hydroxy-5-methylphenyl | 4.2 | 506.2 |
| 3041 | 5-yl-pyridin-2(1H)-one | 2-hydroxy-5-fluorophenyl | 4.2 | 510.2 |
| 3042 | 5-yl-pyridin-2(1H)-one | 3-hydroxy-4-methylphenyl | 4.2 | 506.2 |

TABLE 3-continued

| Cpd | R³ | R⁴ | t_R (min) | MS (M + H)⁺ |
|---|---|---|---|---|
| 3043 | 5-ethyl-6-methyl-pyridin-2(1H)-one | 4-hydroxy-3-(N,N-dimethylcarbamoyl)phenyl | 4.2 | 577.2 |
| 3044 | Et | 4-hydroxy-3-(4-methylpiperazine-1-carbonyl)phenyl | 4.2 | 539.2 |
| 3045 | 4-methoxybenzyl | 4-hydroxy-3-(4-methylpiperazine-1-carbonyl)phenyl | 4.8 | 631.2 |
| 3046 | 2-chlorobenzyl | 4-hydroxy-3-(4-methylpiperazine-1-carbonyl)phenyl | 5.0 | 636.2, 638.2 |
| 3047 | cyclopropylmethyl | 4-hydroxy-3-carbamoylphenyl | 5.0 | 482.2 |
| 3048 | cyclopropylmethyl | 4-hydroxy-3-(N-methylcarbamoyl)phenyl | 5.1 | 496.2 |

TABLE 3-continued

| Cpd | R³ | R⁴ | $t_R$ (min) | MS $(M+H)^+$ |
|---|---|---|---|---|
| 3049 | cyclopropylmethyl | 4-hydroxy-3-(N,N-dimethylcarbamoyl)phenyl | 5.3 | 510.2 |
| 3050 | cyclopropylmethyl | 4-hydroxy-3-(4-methylpiperazine-1-carbonyl)phenyl | 4.6 | 565.3 |
| 3051 | 4-methoxy-3-hydroxybenzyl | 4-hydroxy-3-(4-ethylpiperazine-1-carbonyl)phenyl | 4.7 | 661.3 |
| 3052 | 4-methoxy-3-hydroxybenzyl | 4-hydroxy-3-(4-isopropylpiperazine-1-carbonyl)phenyl | 4.7 | 675.3 |
| 3053 | 4-methoxy-3-hydroxybenzyl | 4-hydroxy-3-(4-(hydroxymethyl)piperidine-1-carbonyl)phenyl | 5.1 | 662.3 |
| 3054 | 4-methoxy-3-hydroxybenzyl | 4-hydroxy-3-(piperazine-1-carbonyl)phenyl | 4.6 | 633.2 |

TABLE 3-continued

| Cpd | R³ | R⁴ | t_R (min) | MS (M + H)⁺ |
|---|---|---|---|---|
| 3055 | (pyrrolidine with N-ethyl) | 4-hydroxy-benzoic acid (CO₂H) | 4.6 | 540.2 |
| 3056 | 4-methoxy-3-hydroxyphenyl | 4-hydroxy-3-[4-(2-hydroxyethyl)piperazin-1-yl-carbonyl]phenyl | 4.6 | 677.3 |
| 3057 | 3-methyl-2-oxo-1,2-dihydropyridin-5-yl | 2-hydroxyphenyl | 4.8 | 506.2 |
| 3058 | 2-oxo-1,2-dihydropyridin-5-yl | 4-hydroxy-3-(N,N-dimethylcarbamoyl)phenyl | 4.5 | 563.2 |
| 3059 | 2-hydroxyphenyl | 4-hydroxy-3-(4-methylpiperazin-1-yl-carbonyl)phenyl | 4.8 | 617.2 |
| 3060 | 3-hydroxyphenyl | 4-hydroxy-3-(4-methylpiperazin-1-yl-carbonyl)phenyl | 4.8 | 617.2 |
| 3061 | benzo[1,3]dioxol-5-yl | 4-hydroxy-3-(4-methylpiperazin-1-yl-carbonyl)phenyl | 5.0 | 645.2 |

TABLE 3-continued
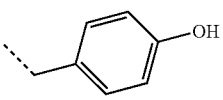
| Cpd | R³ | R⁴ | t_R (min) | MS (M + H)⁺ |
|---|---|---|---|---|
| 3062 | 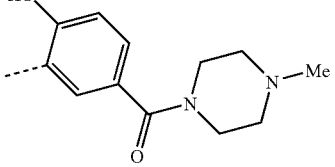 | 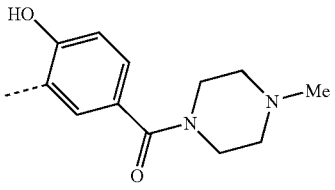 | 4.6 | 617.3 |
| 3063 | —CH₂CH₂OMe | 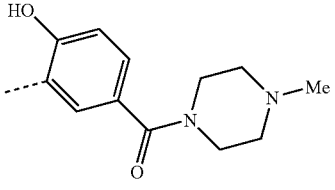 | 4.3 | 569.3 |
| 3064 | (Me)₂CH— | 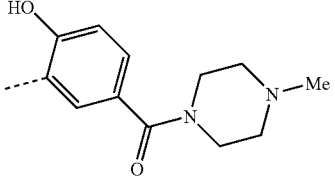 | 4.5 | 553.3 |
| 3065 | —CH₂CH(Me)₂ | 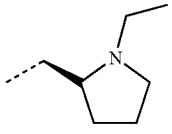 | 4.6 | 567.3 |
| 3066 | 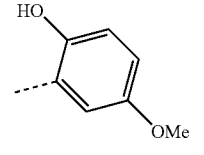 | 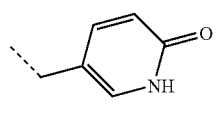 | 4.2 | 526.2 |
| 3067 | 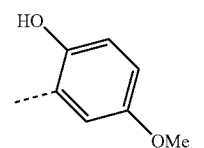 | 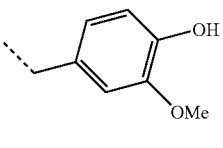 | 4.2 | 522.2 |
| 3068 | 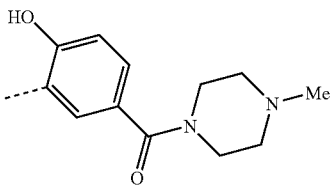 |  | 4.6 | 647.3 |

TABLE 3-continued

| Cpd | R³ | R⁴ | t_R (min) | MS (M + H)⁺ |
|---|---|---|---|---|
| 3069 | 3-Me-5-yl-pyridin-2(1H)-one | 2-hydroxy-5-fluorophenyl | 5.0 | 524.1 |
| 3070 | 5-yl-pyridin-2(1H)-one | 2-hydroxy-5-chlorophenyl | 5.1 | 526.1, 528.1 |
| 3071 | 4-OMe-3-OH-phenyl | 4-hydroxy-3-(4-hydroxypiperidine-1-carbonyl)phenyl | 5.0 | 648.2 |
| 3072 | 5-yl-pyridin-2(1H)-one | 2-hydroxy-4-methoxyphenyl | 4.2 | 522.1 |
| 3073 | 5-yl-pyridin-2(1H)-one | 4-methyl-1H-imidazol-5-yl | 3.8 | 480.1 |
| 3074 | 5-yl-pyridin-2(1H)-one | thiazol-2-yl | 5.5 | 483.1 |
| 3075 | 5-yl-pyridin-2(1H)-one | 2-ethyl-1H-imidazol-5-yl | 4.0 | 494.1 |
| 3076 | (S)-1-ethylpyrrolidin-2-yl | 2-hydroxy-4-methoxyphenyl | 4.0 | 526.2 |
| 3077 | 5-yl-pyridin-2(1H)-one | 2-hydroxypropyl | 3.7 | 458.1 |

TABLE 3-continued

| Cpd | R³ | R⁴ | $t_R$ (min) | MS (M + H)⁺ |
|---|---|---|---|---|
| 3078 | 5-(2-oxo-1H-pyridinyl) | 3-methylisoxazol-4-yl | 4.8 | 481.1 |
| 3079 | 5-(2-oxo-1H-pyridinyl) | thiazol-4-yl | 4.5 | 483.1 |
| 3080 | 5-(2-oxo-1H-pyridinyl) | 3-methyl-1-methyl-pyrazol-4-yl | 3.9 | 494.1 |
| 3081 | 5-(2-oxo-1H-pyridinyl) | 3-methyl-1-methyl-pyrazol-5-yl | 4.8 | 494.1 |
| 3082 | 5-(2-oxo-1H-pyridinyl) | 4-methylthiazol-5-yl | 4.5 | 497.1 |
| 3083 | 5-(2-oxo-1H-pyridinyl) | 2-methylthiazol-4-yl | 4.6 | 497.1 |
| 3084 | 5-(2-oxo-1H-pyridinyl) | 4-methyl-1,2,3-thiadiazol-5-yl | 5.1 | 498.1 |
| 3085 | (S)-1-ethylpyrrolidin-2-yl | 3-methyl-1-methyl-pyrazol-4-yl | 3.9 | 498.2 |
| 3086 | (S)-1-ethylpyrrolidin-2-yl | 2,5-dimethyloxazol-4-yl | 4.8 | 499.2 |

TABLE 3-continued
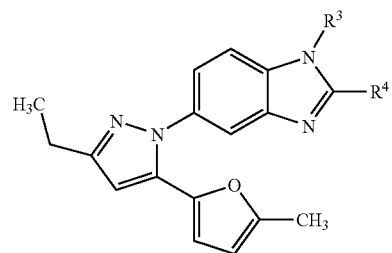
| Cpd | R³ | R⁴ | $t_R$ (min) | MS (M + H)⁺ |
|---|---|---|---|---|
| 3087 | 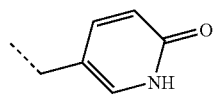 | 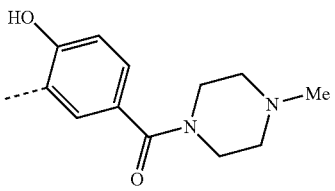 | 4.2 | 618.2 |
| 3088 | 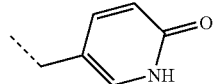 | 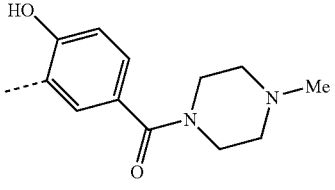 | 4.3 | 632.3 |
| 3089 | 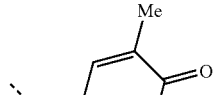 | 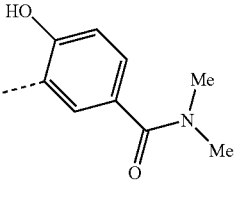 | 4.7 | 577.2 |
| 3090 | 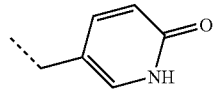 | 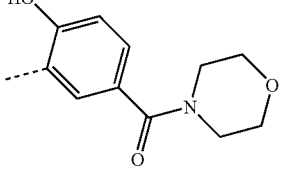 | 4.6 | 605.2 |
| 3091 | 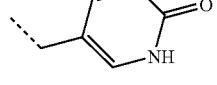 | 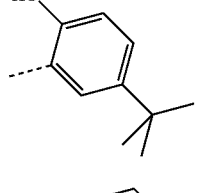 | 5.4 | 548.2 |
| 3092 | 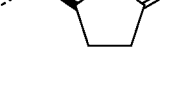 | 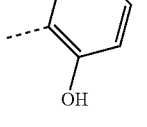 | 4.6 | 482.1 |
| 3093 | 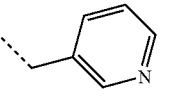 | 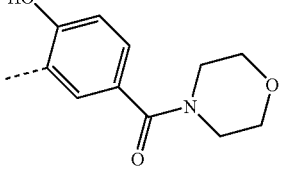 | 4.4 | 589.2 |

TABLE 3-continued
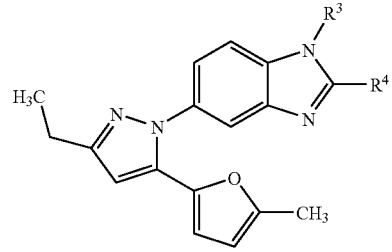
| Cpd | R³ | R⁴ | $t_R$ (min) | MS $(M + H)^+$ |
|---|---|---|---|---|
| 3094 | 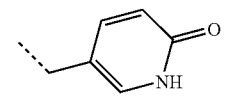 | 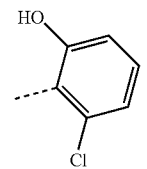 | 5.0 | 526.0 528.0 |
| 3095 | 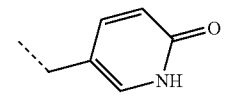 | 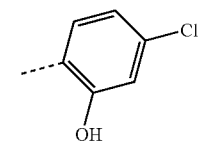 | 5.1 | 526.0 528.0 |
| 3096 | 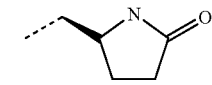 | 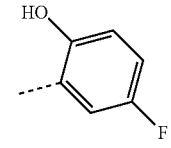 | 4.9 | 500.1 |
| 3097 | 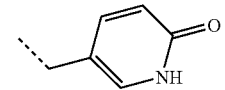 | 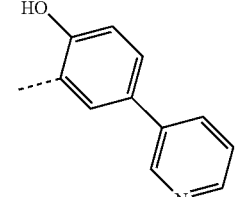 | 4.3 | 569.1 |
| 3098 | 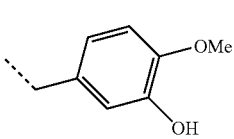 | 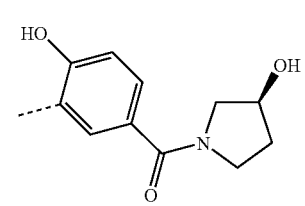 | 5.0 | 634.1 |
| 3099 | 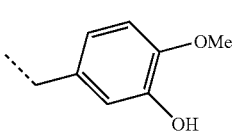 | 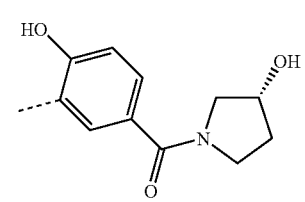 | 5.0 | 634.1 |
| 3100 | 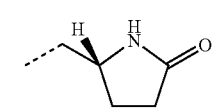 | 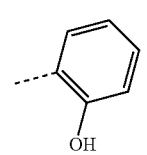 | 4.6 | 482.1 |

TABLE 3-continued
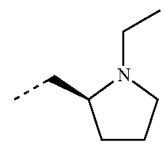
| Cpd | R³ | R⁴ | $t_R$ (min) | MS $(M + H)^+$ |
|---|---|---|---|---|
| 3101 | 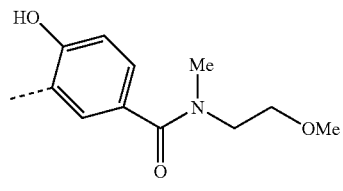 | 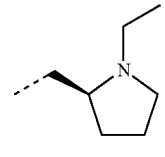 | 4.2 | 611.2 |
| 3102 | 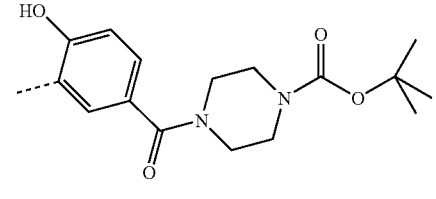 | 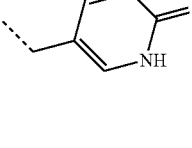 | 5.0 | 708.2 |
| 3103 | 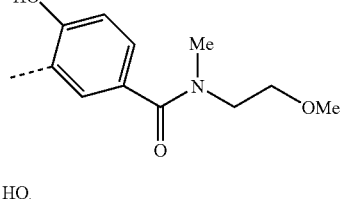 | 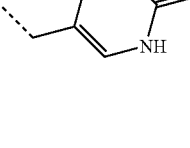 | 4.2 | 607.1 |
| 3104 | 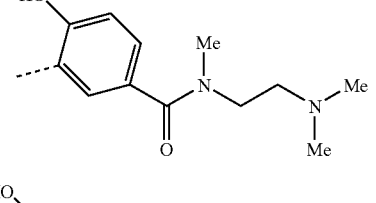 | 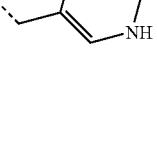 | 3.7 | 620.1 |
| 3105 | 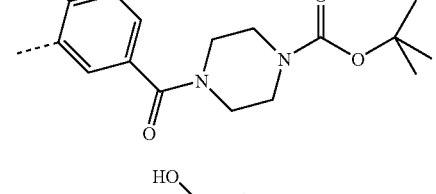 | 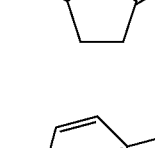 | 5.0 | 704.1 |
| 3106 | 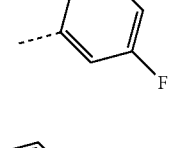 | 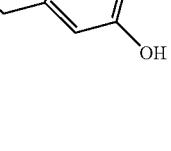 | 4.8 | 500.1 |
| 3107 | 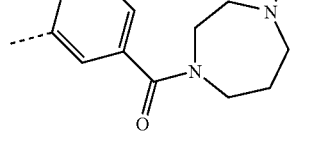 |  | 4.7 | 661.3 |

TABLE 3-continued
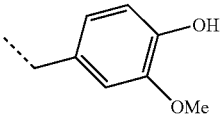
| Cpd | R³ | R⁴ | $t_R$ (min) | MS $(M + H)^+$ |
|---|---|---|---|---|
| 3108 | 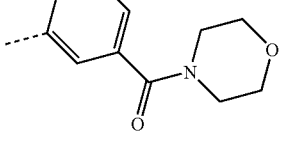 | 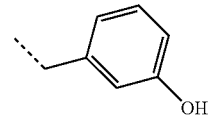 | 5.1 | 634.2 |
| 3109 | 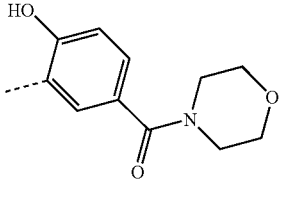 | 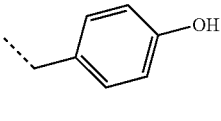 | 5.2 | 604.2 |
| 3110 | 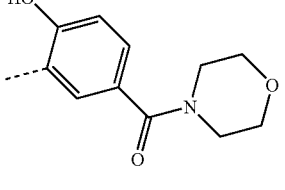 | 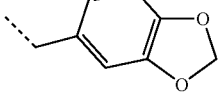 | 5.1 | 604.2 |
| 3111 | 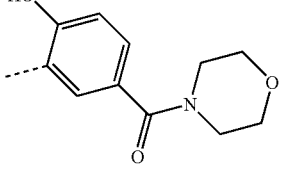 | 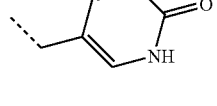 | 5.6 | 632.2 |
| 3112 | 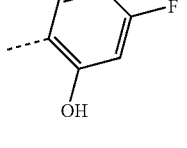 | 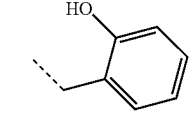 | 4.7 | 510.1 |
| 3113 | 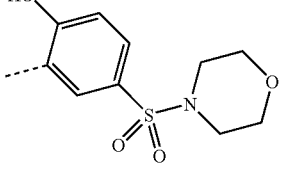 | 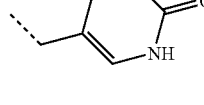 | 6.0 | 640.1 |
| 3114 | 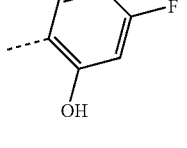 | 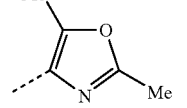 | 5.2 | 495.2 |

TABLE 3-continued

| Cpd | R³ | R⁴ | t_R (min) | MS (M + H)⁺ |
|---|---|---|---|---|
| 3115 | 3-methoxybenzyl | 4-hydroxy-3-(morpholine-4-carbonyl)phenyl | 5.7 | 618.2 |
| 3116 | (6-oxo-1,6-dihydropyridin-3-yl)methyl | 4-(diethylamino)-2-hydroxyphenyl | 5.0 | 563.2 |
| 3117 | —CH₂CH₂OMe | 4-hydroxy-3-(morpholine-4-carbonyl)phenyl | 4.9 | 556.2 |
| 3118 | —CH₂CH₂OMe | 4-hydroxy-3-(4-(2-hydroxyethyl)piperazine-1-carbonyl)phenyl | 4.3 | 599.3 |
| 3119 | 3-hydroxy-4-methoxybenzyl | 4-hydroxy-3-(2-(hydroxymethyl)pyrrolidine-1-carbonyl)phenyl | 5.2 | 648.2 |
| 3120 | 3-hydroxy-4-methoxybenzyl | 4-hydroxy-3-(2-(hydroxymethyl)pyrrolidine-1-carbonyl)phenyl | 5.2 | 648.2 |
| 3121 | 3-methoxybenzyl | 4-hydroxy-3-(4-(2-hydroxyethyl)piperazine-1-carbonyl)phenyl | 4.9 | 661.3 |

TABLE 3-continued
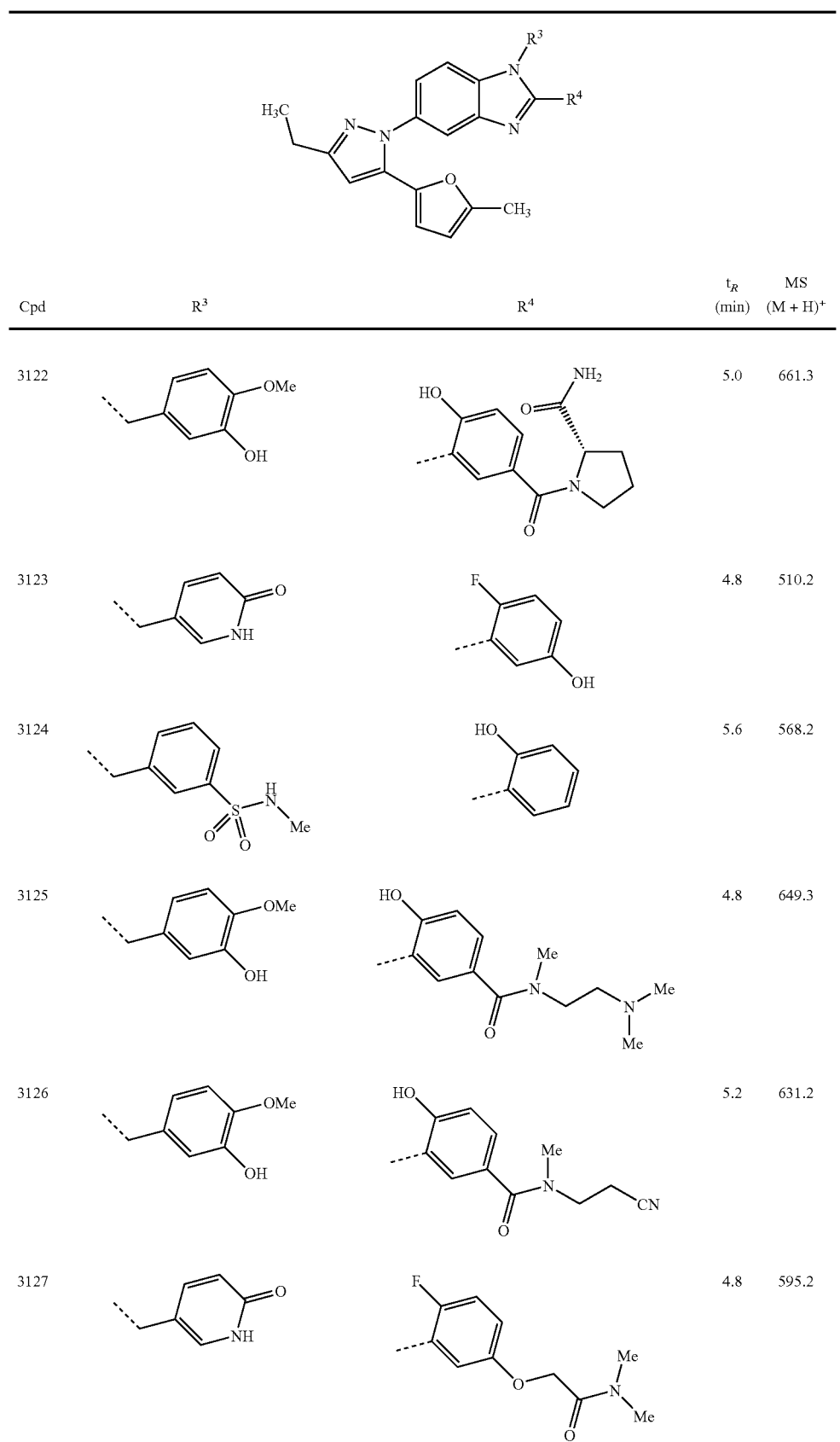
| Cpd | R³ | R⁴ | $t_R$ (min) | MS $(M + H)^+$ |
|---|---|---|---|---|
| 3122 | 3-OH, 4-OMe benzyl | 4-OH, 3-(prolinamide carbonyl) phenyl | 5.0 | 661.3 |
| 3123 | 5-(2-oxo-1H-pyridyl) | 4-F, 3-OH phenyl | 4.8 | 510.2 |
| 3124 | 3-(N-methylsulfamoyl) phenyl | 2-OH phenyl | 5.6 | 568.2 |
| 3125 | 3-OH, 4-OMe benzyl | 4-OH, 3-(N-methyl-N-(2-dimethylaminoethyl)carbamoyl) phenyl | 4.8 | 649.3 |
| 3126 | 3-OH, 4-OMe benzyl | 4-OH, 3-(N-methyl-N-(2-cyanoethyl)carbamoyl) phenyl | 5.2 | 631.2 |
| 3127 | 5-(2-oxo-1H-pyridyl) | 4-F, 3-(N,N-dimethylcarbamoylmethoxy) phenyl | 4.8 | 595.2 |

TABLE 3-continued

| Cpd | R³ | R⁴ | t_R (min) | MS (M + H)⁺ |
|---|---|---|---|---|
| 3128 | 4-OMe, 3-OH phenyl | 4-OH, 3-[C(O)N(Me)CH₂CH₂OH] phenyl | 5.0 | 622.2 |
| 3129 | 3-(methylsulfonyl)phenyl | 2-hydroxyphenyl | 5.4 | 553.2 |
| 3130 | 4-OMe, 3-OH phenyl | 4-OH, 3-[C(O)N(Me)CH₂CH₂OMe] phenyl | 5.3 | 636.3 |
| 3131 | 4-OMe, 3-OH phenyl | 4-OH, 3-[C(O)N(Me)CH₂C(O)NMe₂] phenyl | 5.1 | 663.3 |
| 3132 | 4-F, 3-OMe phenyl | 4-OH, 3-(morpholin-4-ylcarbonyl)phenyl | 5.8 | 636.3 |
| 3133 | 3-(morpholin-4-yl)phenyl | 4-OH, 3-(pyrrolidin-1-ylcarbonyl)phenyl | 5.9 | 657.3 |

TABLE 3-continued
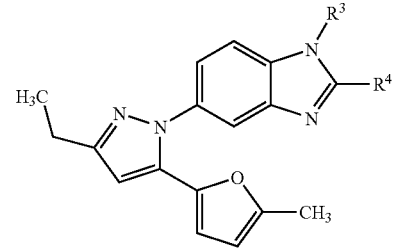
| Cpd | R³ | R⁴ | $t_R$ (min) | MS $(M + H)^+$ |
|---|---|---|---|---|
| 3134 | 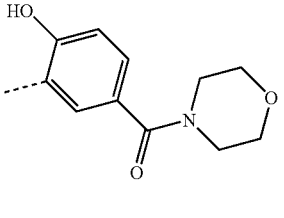 | 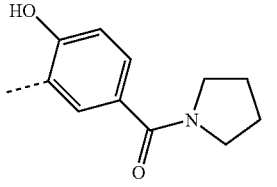 | 5.6 | 673.3 |
| 3135 | —CH₂CH₂CN | 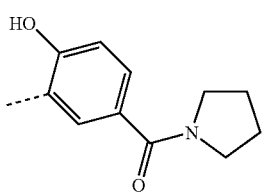 | 5.2 | 535.2 |
| 3136 | —CH₂CH₂OMe | | 5.3 | 540.3 |
| 3137 | —CH₂CH₂OMe | 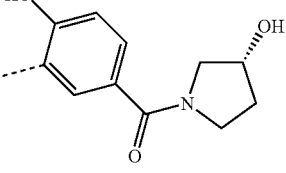 | 4.8 | 556.3 |
| 3138 | —CH₂CH₂OEt | 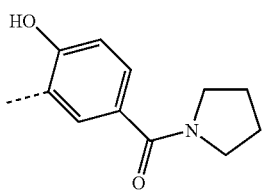 | 5.6 | 554.3 |
| 3139 | —CH₂CH₂OCH(CH₃)₂ | 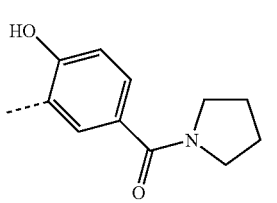 | 5.8 | 568.3 |

TABLE 3-continued

| Cpd | R³ | R⁴ | $t_R$ (min) | MS $(M+H)^+$ |
|---|---|---|---|---|
| 3140 | —CH₂CH₂CH₂OMe | 4-HO, 3-(pyrrolidin-1-ylcarbonyl)phenyl | 5.4 | 554.3 |
| 3141 | —C(CH₃)₂NH₂ | 4-HO, 3-(pyrrolidin-1-ylcarbonyl)phenyl | 4.5 | 553.3 |
| 3142 | —CH(CH₃)CH₂OMe | 4-HO, 3-(pyrrolidin-1-ylcarbonyl)phenyl | 5.4 | 554.3 |
| 3143 | piperidin-3-ylmethyl | 4-HO, 3-(pyrrolidin-1-ylcarbonyl)phenyl | 4.5 | 579.4 |
| 3144 | (6-methylpyridin-3-yl)methyl | 4-HO, 3-(pyrrolidin-1-ylcarbonyl)phenyl | 4.6 | 587.3 |
| 3145 | (6-methylpyridin-3-yl)methyl | 4-HO, 3-((3R)-3-hydroxypyrrolidin-1-ylcarbonyl)phenyl | 4.2 | 603.3 |

TABLE 3-continued
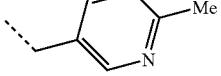
| Cpd | R³ | R⁴ | t_R (min) | MS (M + H)⁺ |
|---|---|---|---|---|
| 3146 | 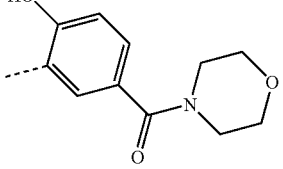 | 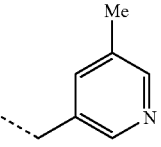 | 4.4 | 603.3 |
| 3147 | 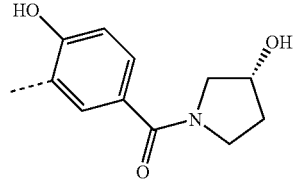 | 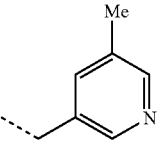 | 4.3 | 603.2 |
| 3148 | 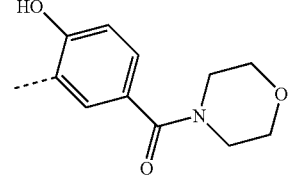 | 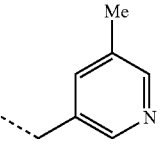 | 4.4 | 603.2 |
| 3149 | 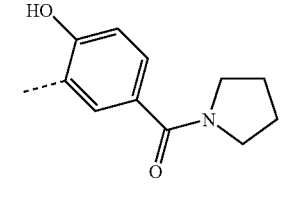 | 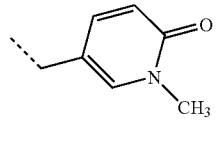 | 4.6 | 587.2 |
| 3150 | 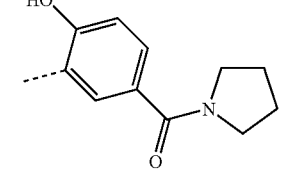 | 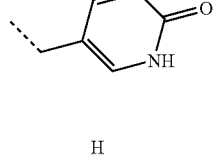 | 4.8 | 603.2 |
| 3151 | 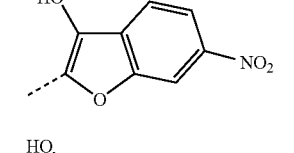 | 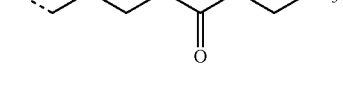 | 5.3 | 537.1 |
| 3152 | 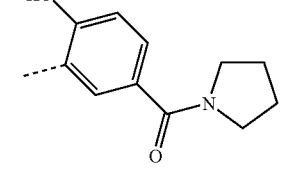 |  | 5.1 | 609.2 |

TABLE 3-continued
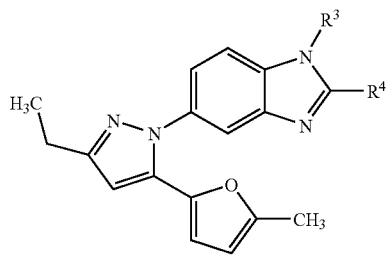
| Cpd | R³ | R⁴ | t_R (min) | MS (M + H)⁺ |
|---|---|---|---|---|
| 3153 | ⋯CH₂CH₂CH₂NHS(O)₂CH₃ | 4-HO-3-(pyrrolidine-1-carbonyl)phenyl | 4.9 | 617.1 |
| 3154 | pyridin-3-ylmethyl | 4-COOH-phenyl | 3.3 | 504.1 |
| 3155 | 3-hydroxy-4-methoxybenzyl | pyridine N-oxide (4-yl) | 3.8 | 522.1 |
| 3156 | 3-hydroxy-4-methoxybenzyl | 4-COOH-phenyl | 3.4 | 549.1 |
| 3157 | 2-chlorobenzyl | 4-COOH-phenyl | 4.4 | 537.1, 539.1 |
TABLE 4
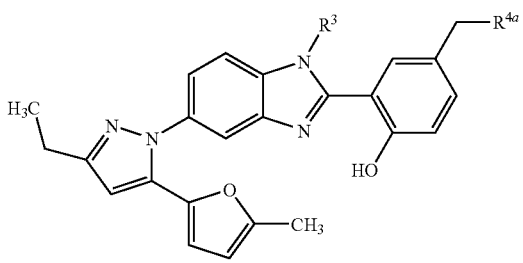
| Cpd | R³ | R⁴ᵃ | t_R (min) | MS (M + H)⁺ |
|---|---|---|---|---|
| 4001 | —CH₂CH₂OMe | morpholin-4-yl | 4.0 | 542.2 |

TABLE 4-continued
| Cpd | R³ | R⁴ᵃ | t_R (min) | MS (M + H)⁺ |
|---|---|---|---|---|
| 4002 | —CH₂CH₂OMe | 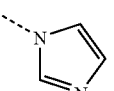 | 4.9 | 523.3 |
| 4003 | —CH₂CH₂OMe | 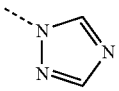 | 3.9 | 523.3 |
| 4004 | —CH₂CH₂OMe | 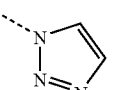 | 4.5 | 524.3 |
| 4005 | —CH₂CH₂OMe | 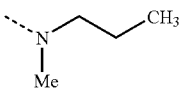 | 4.6 | 524.3 |
| 4006 | —CH₂CH₂OMe | 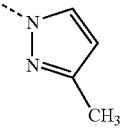 | 4.1 | 528.3 |
| 4007 | —CH₂CH₂OMe | 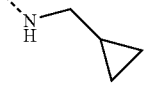 | 5.1 | 537.3 |
| 4008 | —CH₂CH₂OMe | 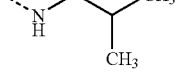 | 4.2 | 526.3 |
| 4009 | —CH₂CH₂OMe | 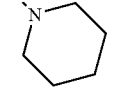 | 4.3 | 528.3 |
| 4010 | —CH₂CH₂OMe | 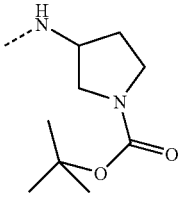 | 4.1 | 540.3 |
| 4011 | —CH₂CH₂OMe |  | 4.7 | 641.4 |

TABLE 4-continued
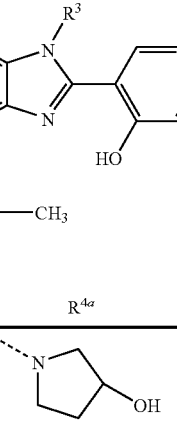
| Cpd | R³ | R⁴ᵃ | t_R (min) | MS (M + H)⁺ |
|---|---|---|---|---|
| 4012 | —CH₂CH₂OMe | 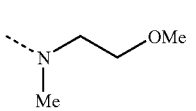 | 3.9 | 542.3 |
| 4013 | —CH₂CH₂OMe | 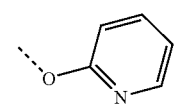 | 4.0 | 544.3 |
| 4014 | —CH₂CH₂OMe | 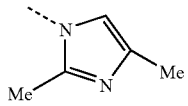 | 4.7 | 550.3 |
| 4015 | —CH₂CH₂OMe | 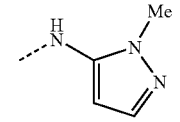 | 4.1 | 551.3 |
| 4016 | —CH₂CH₂OMe | 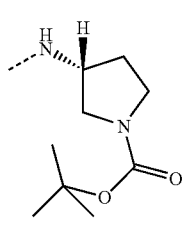 | 4.1 | 552.3 |
| 4017 | —CH₂CH₂OMe | 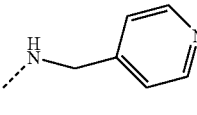 | 4.7 | 641.4 |
| 4018 | —CH₂CH₂OMe | 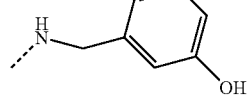 | 3.6 | 563.3 |
| 4019 | —CH₂CH₂OMe | 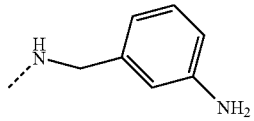 | 4.3 | 578.3 |
| 4020 | —CH₂CH₂OMe | 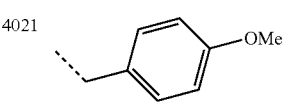 | 4.2 | 577.3 |
| 4021 | 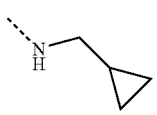 | | 4.9 | 588.3 |

TABLE 4-continued

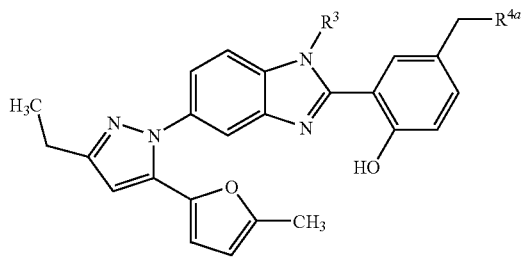

| Cpd | R³ | R⁴ᵃ | $t_R$ (min) | MS $(M + H)^+$ |
|---|---|---|---|---|
| 4022 | pyridin-2(1H)-one-5-ylmethyl | azetidin-1-yl | 3.7 | 561.3 |
| 4023 | pyridin-2(1H)-one-5-ylmethyl | pyrazol-1-yl | 4.4 | 572.3 |
| 4024 | pyridin-2(1H)-one-5-ylmethyl | imidazol-1-yl | 3.7 | 572.3 |
| 4025 | pyridin-2(1H)-one-5-ylmethyl | 1,2,4-triazol-1-yl | 4.0 | 573.3 |
| 4026 | pyridin-2(1H)-one-5-ylmethyl | 1,2,3-triazol-1-yl | 4.1 | 573.3 |
| 4027 | pyridin-2(1H)-one-5-ylmethyl | N(Me)(n-Pr) | 3.9 | 577.3 |
| 4028 | pyridin-2(1H)-one-5-ylmethyl | NMe₂ | 3.7 | 549.3 |
| 4029 | pyridin-2(1H)-one-5-ylmethyl | 3-methylpyrazol-1-yl | 4.4 | 586.3 |
| 4030 | pyridin-2(1H)-one-5-ylmethyl | 3,6-dihydro-2H-pyridin-1-yl | 3.8 | 587.3 |
| 4031 | pyridin-2(1H)-one-5-ylmethyl | N(Me)CH₂CH₂CN | 3.8 | 588.3 |
| 4032 | pyridin-2(1H)-one-5-ylmethyl | NH-iBu | 3.9 | 577.3 |

TABLE 4-continued

| Cpd | R³ | R⁴ᵃ | $t_R$ (min) | MS (M + H)⁺ |
|---|---|---|---|---|
| 4033 | 5-(2-oxo-1H-pyridinyl)methyl | piperidin-1-yl | 3.8 | 589.3 |
| 4034 | 5-(2-oxo-1H-pyridinyl)methyl | 3-hydroxypyrrolidin-1-yl | 3.7 | 591.3 |
| 4035 | 5-(2-oxo-1H-pyridinyl)methyl | morpholin-4-yl | 3.8 | 591.3 |
| 4036 | 5-(2-oxo-1H-pyridinyl)methyl | N-Me-N-(2-methoxyethyl)amino | 3.8 | 593.3 |
| 4037 | 5-(2-oxo-1H-pyridinyl)methyl | pyridin-2-ylamino | 3.8 | 598.3 |
| 4038 | 5-(2-oxo-1H-pyridinyl)methyl | pyridin-2-yloxy | 4.2 | 599.3 |
| 4039 | 5-(2-oxo-1H-pyridinyl)methyl | 2,4-dimethylimidazol-1-yl | 3.8 | 600.3 |
| 4040 | 5-(2-oxo-1H-pyridinyl)methyl | N-Me-N-(carbamoylmethyl)amino | 3.6 | 592.3 |

TABLE 5
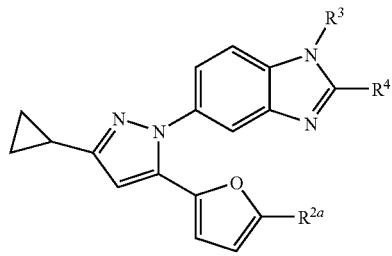
| Cpd | R²ᵃ | R³ | R⁴ | t_R (min) | MS (M + H)⁺ |
|---|---|---|---|---|---|
| 5001 | Me | 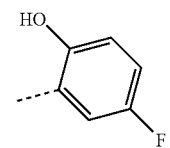 |  | 4.9 | 522.1 |
| 5002 | Me | 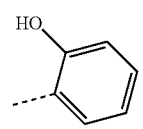 | 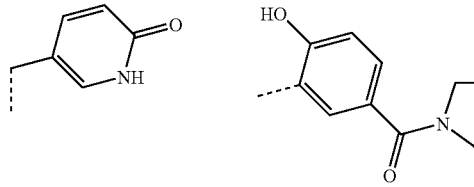 | 4.7 | 504.1 |
| 5003 | Me | 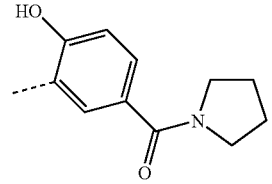 | 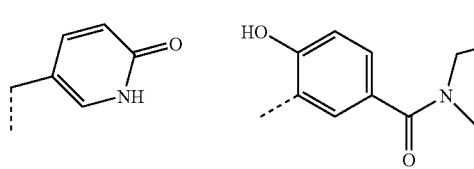 | 4.8 | 601.3 |
| 5004 | Me | 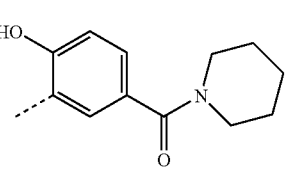 | 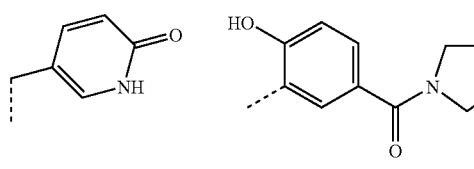 | 5.0 | 615.3 |
| 5005 | Cl | 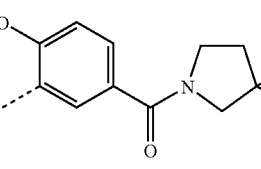 | 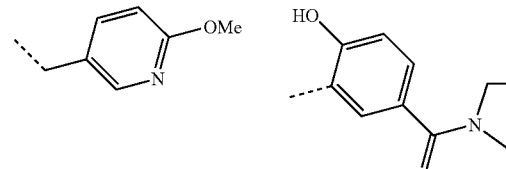 | 5.3 | 658.2 660.1 |
| 5006 | Cl | 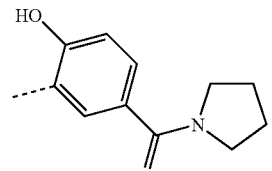 | 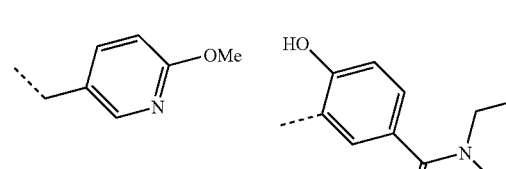 | 6.0 | 635.2 637.2 |
| 5007 | Cl | 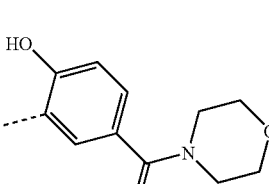 | | 5.8 | 651.2 653.2 |

TABLE 5-continued
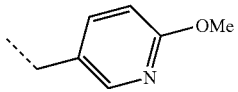
| Cpd | R²ᵃ | R³ | R⁴ | t_R (min) | MS (M + H)⁺ |
|---|---|---|---|---|---|
| 5008 | Cl | 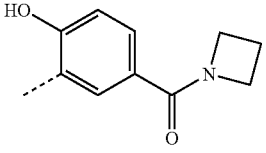 | 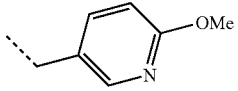 | 5.9 | 621.2 623.2 |
| 5009 | Cl | 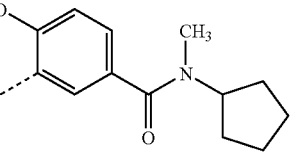 | 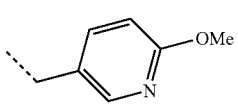 | 6.4 | 663.2 665.2 |
| 5010 | Cl | 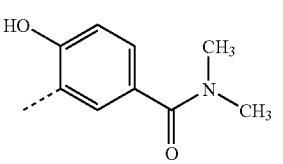 | 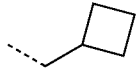 | 5.8 | 609.2 611.2 |
| 5011 | Cl | 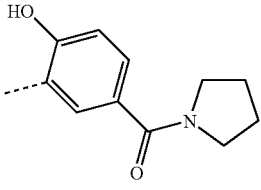 | 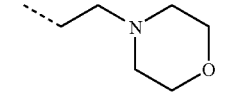 | 6.2 | 582.2 584.2 |
| 5012 | Cl | 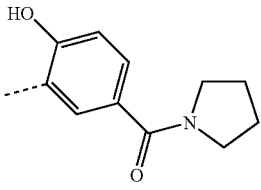 | 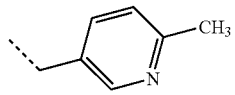 | 4.9 | 627.1 629.1 |
| 5013 | Cl | 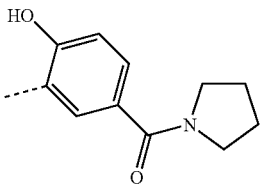 | 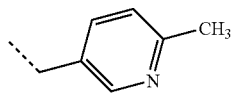 | 4.9 | 619.2 621.2 |
| 5014 | Cl | 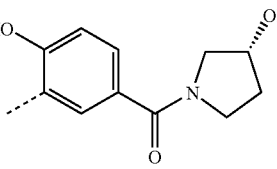 | | 4.5 | 635.1 637.1 |

TABLE 5-continued

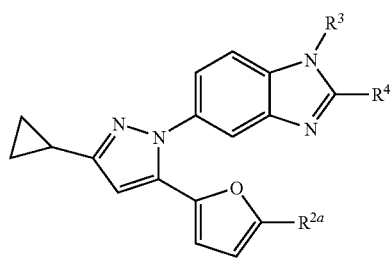

| Cpd | R[2a] | R[3] | R[4] | $t_R$ (min) | MS (M + H)+ |
|---|---|---|---|---|---|
| 5015 | Cl | 5-(2-methylpyridyl) | 4-hydroxy-3-(morpholinocarbonyl)phenyl | 4.7 | 635.1 637.1 |
| 5016 | Cl | 5-(2-ethoxypyridyl) | 4-hydroxy-3-(morpholinocarbonyl)phenyl | 5.8 | 665.3 667.3 |
| 5017 | Cl | 5-(2-isopropoxypyridyl) | 4-hydroxy-3-(pyrrolidinocarbonyl)phenyl | 6.3 | 663.3 665.3 |
| 5018 | Cl | 5-(2-isopropoxypyridyl) | 4-hydroxy-3-(morpholinocarbonyl)phenyl | 6.1 | 679.3 681.3 |
| 5019 | Cl | 5-(2-ethoxypyridyl) | 4-hydroxy-3-((2S)-2-carboxypyrrolidinocarbonyl)phenyl | 5.8 | 693.2 695.2 |
| 5020 | Cl | 5-(2-ethoxypyridyl) | 4-hydroxy-3-(pyrrolidinocarbonyl)phenyl | 6.1 | 649.2 651.2 |

TABLE 5-continued
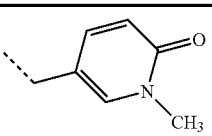
| Cpd | R[2a] | R[3] | R[4] | t_R (min) | MS (M + H)+ |
|---|---|---|---|---|---|
| 5021 | Cl | 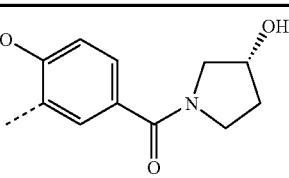 | 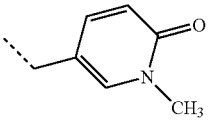 | 4.8 | 652.2 654.2 |
| 5022 | Cl | 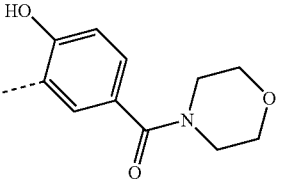 | 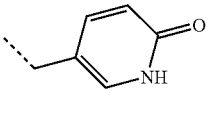 | 5.0 | 652.2 654.3 |
| 5023 | Cl | 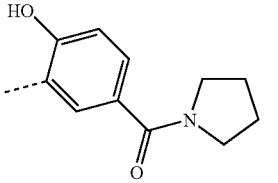 | 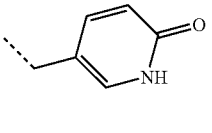 | 5.0 | 621.2 623.2 |
| 5024 | Cl | 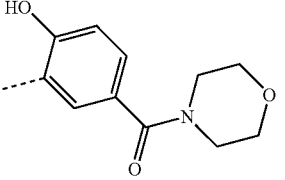 | 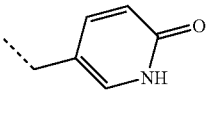 | 4.8 | 637.2 639.2 |
| 5025 | Cl | 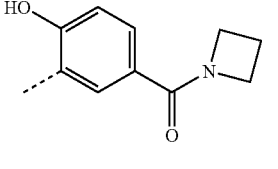 | 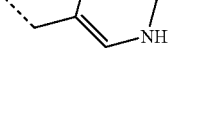 | 4.9 | 607.2 609.2 |
| 5026 | Cl | 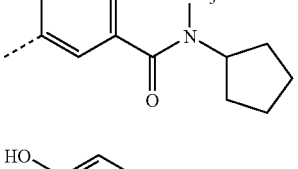 | 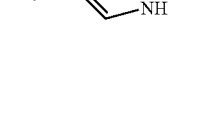 | 5.4 | 649.2 651.2 |
| 5027 | Cl | 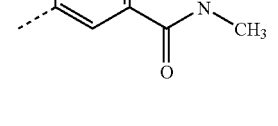 | | 4.8 | 595.2 597.2 |

TABLE 5-continued

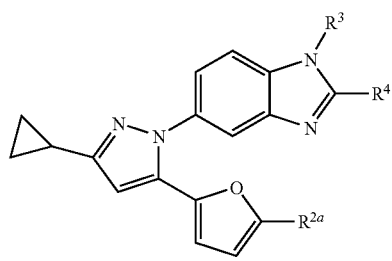

| Cpd | R$^{2a}$ | R$^3$ | R$^4$ | t$_R$ (min) | MS (M + H)$^+$ |
|---|---|---|---|---|---|
| 5028 | Cl | 5-(2-ethoxypyridyl) | 4-hydroxy-3-{N-methyl-N-[2-(dimethylamino)ethyl]carbamoyl}phenyl | 5.2 | 678.1 680.2 (M − H)$^-$ |
| 5029 | Cl | 1-ethyl-2-oxo-1,2-dihydropyridin-5-yl | 4-hydroxy-3-[(3-hydroxypyrrolidin-1-yl)carbonyl]phenyl | 5.0 | 665.2 667.2 |
| 5030 | Cl | 1-ethyl-2-oxo-1,2-dihydropyridin-5-yl | 4-hydroxy-3-(morpholin-4-ylcarbonyl)phenyl | 5.2 | 665.2 667.2 |
| 5031 | Cl | 3-(morpholin-4-yl)phenyl | 4-hydroxy-3-(pyrrolidin-1-ylcarbonyl)phenyl | 6.1 | 689.3 691.3 |
| 5032 | Cl | 3-(morpholin-4-yl)phenyl | 4-hydroxy-3-(morpholin-4-ylcarbonyl)phenyl | 5.8 | 705.3 707.2 |
| 5033 | Cl | 5-(2-trifluoromethylpyridyl) | 4-hydroxy-3-(morpholin-4-ylcarbonyl)phenyl | 6.0 | 689.2 691.2 |

TABLE 5-continued

| Cpd | R²ᵃ | R³ | R⁴ | t_R (min) | MS (M + H)⁺ |
|---|---|---|---|---|---|
| 5034 | Cl | 5-(2-trifluoromethyl)pyridyl | 4-hydroxy-3-(pyrrolidin-1-ylcarbonyl)phenyl | 6.2 | 673.1, 675.1 |
| 5035 | Cl | 4-hydroxyphenyl | 4-hydroxy-3-(pyrrolidin-1-ylcarbonyl)phenyl | 5.5 | 620.1, 622.1 |
| 5036 | Cl | 4-hydroxyphenyl | 4-hydroxy-3-(morpholin-4-ylcarbonyl)phenyl | 5.3 | 636.1, 638.1 |
| 5037 | CF₃ | 5-(2-methoxy)pyridyl | 4-hydroxy-3-(pyrrolidin-1-ylcarbonyl)phenyl | 6.0 | 669.2 |
| 5038 | CF₃ | 5-(2-methoxy)pyridyl | 4-hydroxy-3-(morpholin-4-ylcarbonyl)phenyl | 5.7 | 685.1 |
| 5039 | CF₃ | 5-(2-oxo-1H-pyridyl) | 4-hydroxy-3-(morpholin-4-ylcarbonyl)phenyl | 5.0 | 671.1 |

TABLE 5-continued
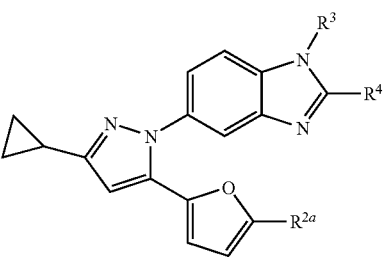
| Cpd | R²ᵃ | R³ | R⁴ | t_R (min) | MS (M + H)⁺ |
|---|---|---|---|---|---|
| 5040 | CF₃ | 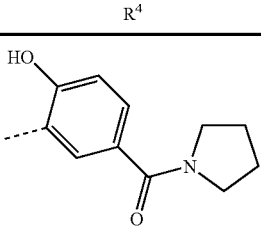 | 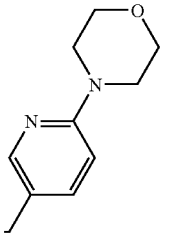 | 5.2 | 655.1 |
| 5041 | Cl | 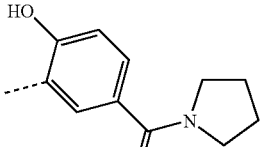 | 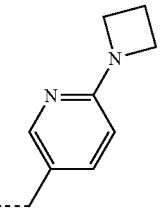 | 5.0 | 690.1 692.1 |
| 5042 | Cl | 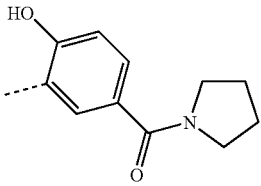 | 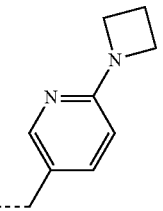 | 5.0 | 660.1 662.1 |
| 5043 | Cl | 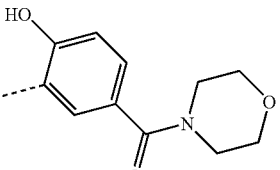 | 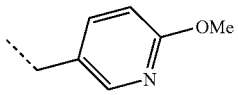 | 4.8 | 676.1 678.1 |
| 5044 | Cl | 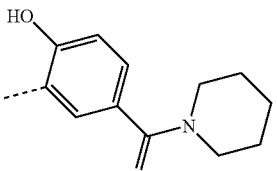 | 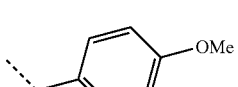 | 6.0 | 649.2 651.2 |
| 5045 | Cl | 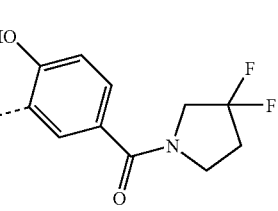 | | 6.0 | 671.2 673.2 |

TABLE 5-continued

| Cpd | R²ᵃ | R³ | R⁴ | t_R (min) | MS (M + H)⁺ |
|---|---|---|---|---|---|
| 5046 | Cl | 5-(2-oxo-1H-pyridin-5-yl) | 4-hydroxy-3-(piperidine-1-carbonyl)phenyl | 5.1 | 635.1, 637.1 |
| 5047 | CF₃ | 5-(2-oxo-1H-pyridin-5-yl) | 4-hydroxy-3-(N,N-dimethylcarbamoyl)phenyl | 5.0 | 629.1 |
| 5048 | CF₃ | 5-(2-oxo-1H-pyridin-5-yl) | 4-hydroxy-3-[N-methyl-N-(2-dimethylaminoethyl)carbamoyl]phenyl | 4.7 | 686.1 |
| 5049 | CF₃ | 5-(2-oxo-1H-pyridin-5-yl) | 4-hydroxy-3-[4-(thiazol-2-yl)piperazine-1-carbonyl]phenyl | 4.8 | 753.0 |
| 5050 | CF₃ | 5-(3-methyl-2-oxo-1H-pyridin-5-yl) | 4-hydroxy-3-(pyrrolidine-1-carbonyl)phenyl | 5.3 | 669.2 |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of formula (I):

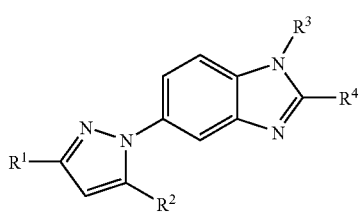

wherein $R^1$ is $(C_{1-4})$alkyl or $(C_{3-4})$cycloalkyl;

$R^2$ is a 5- or 6-membered heterocycle containing 1 to 4 heteroatoms each independently selected from N, O and S, wherein the heterocycle is optionally substituted with 1 to 3 substituents each independently selected from halo, $(C_{1-6})$alkyl and $(C_{1-6})$haloalkyl;

$R^3$ is $(C_{1-6})$alkyl, $(C_{3-7})$cycloalkyl-$(C_{1-6})$alkyl-, aryl-$(C_{1-6})$alkyl- or Het-$(C_{1-6})$alkyl-;

wherein each of the $(C_{1-6})$alkyl, $(C_{3-7})$cycloalkyl-$(C_{1-6})$alkyl-, aryl-$(C_{1-6})$alkyl- and Het-$(C_{1-6})$alkyl- is optionally substituted with 1 to 3 substituents each independently selected from $(C_{1-6})$alkyl, $(C_{1-6})$haloalkyl, halo, oxo, —$N_3$, —CN, —OH, —O$(C_{1-6})$alkyl, —$NH_2$, —NH$(C_{1-6})$alkyl, —N$((C_{1-6})$alkyl$)_2$, —NHC(=O)$(C_{1-6})$alkyl, —NHSO$_2$$(C_{1-6})$alkyl, —C(=O)—$NH_2$, —C(=O)—NH$(C_{1-6})$alkyl, —C(=O)—N$((C_{1-6})$alkyl$)_2$, —C(=O)$(C_{1-6})$alkyl, —SO$_2$$NH_2$, —SO$_2$NH$(C_{1-6})$alkyl, —SO$_2$N$((C_{1-6})$alkyl$)_2$, —SO$_2$$(C_{1-6})$alkyl, Het, Het-$(C_{1-6})$alkyl- and —C(=N$((C_{1-6})$alkyl$)_2$)—N$((C_{1-6})$alkyl$)_2$; and $R^4$ is $(C_{1-6})$alkyl, $(C_{3-7})$cycloalkyl, $(C_{3-7})$cycloalkyl-$(C_{1-6})$alkyl-, aryl, aryl-$(C_{1-6})$alkyl-, Het or Het-$(C_{1-6})$alkyl-;

wherein each of the $(C_{1-6})$alkyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is optionally substituted with 1 to 4 substituents each independently selected from $(C_{1-6})$alkyl, Het, halo, —$NO_2$, —OH, —O$(C_{1-6})$alkyl, —C(=O)$(C_{1-6})$alkyl, —COOH, —N$(R^{41})R^{42}$, —C(=O)—N$(R^{41})R^{42}$ and —SO$_2$—N$(R^{41})R^{42}$;

wherein each of the $(C_{1-6})$alkyl and —O$(C_{1-6})$alkyl are optionally substituted with —N$(R^{41})R^{42}$, —C(=O)—N$(R^{41})R^{42}$ or —O-Het;

wherein $R^{41}$ is H or $(C_{1-6})$alkyl and $R^{42}$ is H, $(C_{1-6})$alkyl, $(C_{3-7})$cycloalkyl, $(C_{3-7})$cycloalkyl-$(C_{1-6})$alkyl-, aryl-$(C_{1-6})$alkyl-, Het or Het-$(C_{1-6})$alkyl-;

wherein the $(C_{1-6})$alkyl is optionally substituted with —CN, —OH, —O$(C_{1-6})$alkyl, —$NH_2$, —NH$(C_{1-6})$alkyl, —N$((C_{1-6})$alkyl$)_2$, —C(=O)—$NH_2$, —C(=O)—NH$(C_{1-6})$alkyl and —C(=O))—N$((C_{1-6})$alkyl$)_2$;

and wherein the aryl portion of the aryl-$(C_{1-6})$alkyl- and the Het are each optionally substituted with 1 to 3 substituents each independently selected from $(C_{1-6})$alkyl, —OH, —$NH_2$ and —C(=O)—O$(C_{1-6})$alkyl; or $R^{41}$ and $R^{42}$ are linked, together with the N to which they are attached, to form a 4- to 7-membered heterocycle optionally further containing 1 to 3 heteroatoms each independently selected from O, N and S, or a 9- to 14-membered heteropolycycle optionally further containing 1 to 3 heteroatoms each independently selected from O, N and S; wherein each of the heterocycle and heteropolycycle is optionally substituted with 1 to 3 substituents each independently selected from $(C_{1-6})$alkyl, Het, halo, —OH, —$NH_2$, —NH$(C_{1-6})$alkyl, —N$((C_{1-6})$alkyl$)_2$, —CN, —COOH, —C(=O)—O$(C_{1-6})$alkyl, —C(=O)—$NH_2$, —C(=O)—NH$(C_{1-6})$alkyl and —C(=O)—N$((C_{1-6})$alkyl$)_2$;

wherein the $(C_{1-6})$alkyl is optionally substituted with —OH;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;

or a salt or ester thereof.

2. The compound according to claim 1, wherein $R^1$ is $(C_{1-4})$alkyl.

3. The compound according to claim 2, wherein $R^1$ is methyl or ethyl.

4. The compound according to claim 3, wherein $R^1$ is ethyl.

5. The compound according to claim 1, wherein $R^1$ is $(C_{3-4})$cycloalkyl.

6. The compound according to claim 5, wherein $R^1$ is cyclopropyl.

7. The compound according to claim 1, wherein $R^2$ is a 5-membered heterocycle containing 1 or 2 heteroatoms each independently selected from N, O and S, wherein the heterocycle is optionally substituted with 1 to 3 substituents each independently selected from halo, $(C_{1-6})$alkyl and $(C_{1-6})$haloalkyl.

8. The compound according to claim 7, wherein $R^2$ is furyl or thienyl, each of the furyl and thienyl being optionally substituted with 1 or 2 substituents each independently selected from halo, $(C_{1-6})$alkyl and $(C_{1-6})$haloalkyl.

9. The compound according to claim 1, wherein $R^3$ is aryl-$(C_{1-3})$alkyl- optionally substituted with 1 to 3 substituents each independently selected from $(C_{1-6})$alkyl, $(C_{1-6})$haloalkyl, halo, —$N_3$, —CN, —OH, —O$(C_{1-6})$alkyl, —$NH_2$, —NH$(C_{1-6})$alkyl, —N$((C_{1-6})$alkyl$)_2$, —NHC(=O)$(C_{1-6})$alkyl, —NHSO$_2$$(C_{1-6})$alkyl, —C(=O)—$NH_2$, —C(=O)—NH$(C_{1-6})$alkyl, —C(=O)—N$((C_{1-6})$alkyl$)_2$, —C(=O)$(C_{1-6})$alkyl, —SO$_2$$NH_2$, —SO$_2$NH$(C_{1-6})$alkyl, —SO$_2$N$((C_{1-6})$alkyl$)_2$, —SO$_2$$(C_{1-6})$alkyl, Het and Het-$(C_{1-6})$alkyl-.

10. The compound according to claim 9, wherein $R^3$ is aryl-$(C_{1-3})$alkyl-optionally substituted with 1 to 3 substituents each independently selected from halo, —$N_3$, —OH, —O$(C_{1-4})$alkyl, —$NH_2$, —NH$(C_{1-4})$alkyl, —N$((C_{1-4})$alkyl$)_2$, —NHC(=O)$(C_{1-4})$alkyl, —SO$_2$$NH_2$, —SO₂NH(C₁₋₄)alkyl, —SO₂N((C₁₋₄)alkyl)₂, —SO₂(C₁₋₄)alkyl, Het and Het-(C₁₋₆)alkyl-;
wherein the Het is a 5- or 6-membered heterocycle containing 1 to 3 heteroatoms each independently selected from N, O and S.

11. The compound according to claim 1, wherein $R^3$ is Het-(C₁₋₃)alkyl- optionally substituted with 1 to 3 substituents each independently selected from (C₁₋₆)alkyl, (C₁₋₆)haloalkyl, halo, oxo, —N₃, —CN, —OH, —O(C₁₋₆)alkyl, —NH₂, —NH(C₁₋₆)alkyl, —N((C₁₋₆)alkyl)₂, —NHC(=O)(C₁₋₆)alkyl, —NHSO₂(C₁₋₆)alkyl, —C(=O)—NH₂, —C(=O)—NH(C₁₋₆)alkyl, —C(=O)—N((C₁₋₆)alkyl)₂, —C(=O)(C₁₋₆)alkyl, —SO₂NH₂, —SO₂NH(C₁₋₆)alkyl, —SO₂N((C₁₋₆)alkyl)₂, —SO₂(C₁₋₆)alkyl, Het, Het-(C₁₋₆)alkyl- and C(=N((C₁₋₆)alkyl)₂)—N((C₁₋₆)alkyl)₂.

12. The compound according to claim 11, wherein $R^3$ is Het-(C₁₋₃)alkyl-, wherein the Het is a 5- or 6-membered heterocycle containing 1 to 3 heteroatoms each independently selected from N, O and S or the Het is a 9- or 10-membered heteropolycycle containing 1 to 3 heteroatoms each independently selected from N, O and S;
wherein the Het-(C₁₋₃)alkyl- is optionally substituted with 1 to 3 substituents each independently selected from (C₁₋₆)alkyl, (C₁₋₆)haloalkyl, oxo, —O(C₁₋₆)alkyl OH, —C(=N((C₁₋₆)alkyl)₂)—N((C₁₋₆)alkyl)₂ and Het, wherein the Het is a 4, 5- or 6-membered heterocycle containing 1 to 3 heteroatoms each independently selected from N, O and S.

13. The compound according to claim 12, wherein $R^3$ is Het-(C₁₋₂)alkyl-, wherein the Het is pyridyl; and wherein the Het-(C₁₋₂)alkyl- is optionally substituted with 1 or 2 substituents each independently selected from (C₁₋₆)alkyl, OH and —O(C₁₋₆)alkyl.

14. The compound according to claim 1, wherein $R^4$ is aryl;
wherein the aryl is optionally substituted with 1 to 4 substituents each independently selected from (C₁₋₆)alkyl, Het, halo, —OH, —O(C₁₋₆)alkyl, —C(=O)(C₁₋₆)alkyl, —COOH, —N(R⁴¹)R⁴², —C(=O)—N(R⁴¹)R⁴² and —SO₂—N(R⁴¹)R⁴²;
wherein each of the (C₁₋₆)alkyl and —O(C₁₋₆)alkyl are optionally substituted with —N(R⁴¹)R⁴², —C(=O)—N(R⁴¹)R⁴² or —O-Het;
wherein $R^{41}$ is H or (C₁₋₆)alkyl and
$R^{42}$ is H, (C₁₋₆)alkyl, (C₃₋₇)cycloalkyl, (C₃₋₇)cycloalkyl-(C₁₋₆)alkyl-, aryl-(C₁₋₆)alkyl-, Het or Het-(C₁₋₆)alkyl-;
wherein the (C₁₋₆)alkyl is optionally substituted with —CN, —OH, —O(C₁₋₆)alkyl, —NH₂, —NH(C₁₋₆)alkyl, —N((C₁₋₆)alkyl)₂, —C(=O)—NH₂, —C(=O)—NH(C₁₋₆)alkyl and —C(=O)—N((C₁₋₆)alkyl)₂;
and wherein the aryl portion of the aryl-(C₁₋₆)alkyl- and the Het are each optionally substituted with 1 to 3 substituents each independently selected from (C₁₋₆)alkyl, —OH, —NH₂ and —C(=O)—O(C₁₋₆)alkyl; or
$R^{41}$ and $R^{42}$ are linked, together with the N to which they are attached, to form a 4- to 7-membered heterocycle optionally further containing 1 to 3 heteroatoms each independently selected from O N and S, or a 9- to 14-membered heteropolycycle optionally further containing 1 to 3 heteroatoms each independently selected from O, N and S; wherein each of the heterocycle and heteropolycycle is optionally substituted with 1 to 3 substituents each independently selected from (C₁₋₆)alkyl, Het, halo, —OH, —NH₂, —NH(C₁₋₆)alkyl, —N((C₁₋₆)alkyl)₂, —CN, —COOH, —C(=O)—O(C₁₋₆)alkyl, —C(=O)—NH₂, —C(=O)—NH(C₁₋₆)alkyl and —C(=O)—N((C₁₋₆)alkyl)₂;
wherein the (C₁₋₆)alkyl is optionally substituted with —OH.

15. The compound according to claim 14, wherein $R^4$ is aryl of the formula:

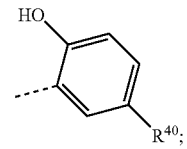

wherein $R^{40o}$ is selected from (C₁₋₆)alkyl, Het, halo, —O(C₁₋₆)alkyl, —C(=O)(C₁₋₆)alkyl, —COOH, —C(=O)—N(R⁴¹)R⁴² and —SO₂—N(R⁴¹)R⁴²;
wherein Het is a 6-membered heterocycle containing 1 or 2 heteroatoms each independently selected from N, O and S; and
wherein the (C₁₋₆)alkyl is optionally substituted with —N(R⁴¹)R⁴² or —O-Het, wherein Het is a 6-membered heterocycle containing 1 or 2 heteroatoms each independently selected from N, O and S;
wherein $R^{41}$ is H or (C₁₋₆)alkyl and
$R^{42}$ is H, (C₁₋₆)alkyl, (C₃₋₇)cycloalkyl, (C₃₋₇)cycloalkyl-(C₁₋₆)alkyl-, aryl-(C₁₋₆)alkyl-, Het or Het-(C₁₋₆)alkyl-;
wherein the (C₁₋₆)alkyl is optionally substituted with —CN, —OH, —O(C₁₋₆)alkyl, —NH₂, —NH(C₁₋₆)alkyl, —N((C₁₋₆)alkyl)₂, —C(=O)—NH₂, —C(=O)—NH(C₁₋₆)alkyl and —C(=O)—N((C₁₋₆)alkyl)₂;
and wherein the aryl portion of the aryl-(C₁₋₆)alkyl- and the Het are each optionally substituted with 1 to 3 substituents each independently selected from (C₁₋₆)alkyl, —OH, —NH₂ and —C(=O)—O(C₁₋₆)alkyl; or
$R^{41}$ and $R^{42}$ are linked, together with the N to which they are attached, to form a 4- to 7-membered heterocycle optionally further containing 1 to 3 heteroatoms each independently selected from O, N and S; wherein the heterocycle is optionally substituted with 1 to 3 substituents each independently selected from (C₁₋₆)alkyl, Het, halo, —OH, —NH₂, —NH(C₁₋₆)alkyl, —N((C₁₋₆)alkyl)₂, —CN, —COOH, —C(=O)—O(C₁₋₆)alkyl, —C(=O)—NH₂, —C(=O)—NH(C₁₋₆)alkyl and —C(=O)—N((C₁₋₆)alkyl)₂;
wherein the (C₁₋₆)alkyl is optionally substituted with —OH; and
wherein the Het is a 5-membered heterocycle containing 1 to 3 heteroatoms each independently selected from N, O and S.

16. The compound according to claim 15, wherein $R^4$ is aryl of the formula:

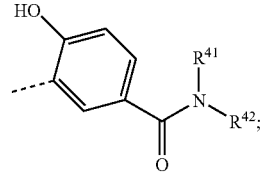

wherein $R^{41}$ is H or $(C_{1-6})$alkyl and
$R^{42}$ is H, $(C_{1-6})$alkyl or $(C_{3-7})$cycloalkyl;
  wherein the $(C_{1-6})$alkyl is optionally substituted with —CN, —OH, —O $(C_{1-6})$alkyl, —NH$_2$, —NH$(C_{1-6})$alkyl, —N$((C_{1-6})$alkyl$)_2$, —C(=O)—NH$_2$, —C(=O)—NH$(C_{1-6})$alkyl and —C(=O)—N$((C_{1-6})$alkyl$)_2$; or
$R^{41}$ and $R^{42}$ are linked, together with the N to which they are attached, to form a 4- to 7-membered heterocycle optionally further containing 1 to 3 heteroatoms each independently selected from O, N and S; wherein the heterocycle is optionally substituted with 1 to 3 substituents each independently selected from $(C_{1-6})$alkyl, Het, halo, —OH, —NH$_2$, —NH$(C_{1-6})$alkyl, —N$((C_{1-6})$alkyl$)_2$, —CN, —COOH, —C(=O)—O$(C_{1-6})$alkyl, —C(=O)—NH$_2$, —C(=O)—NH$(C_{1-6})$alkyl and —C(=O)—N$((C_{1-6})$alkyl$)_2$;
  wherein the $(C_{1-6})$alkyl is optionally substituted with —OH; and
  wherein the Het is a 5-membered heterocycle containing 1 to 3 heteroatoms each independently selected from N, O and S.

17. The compound according to claim 16, wherein $R^4$ is aryl of the formula:

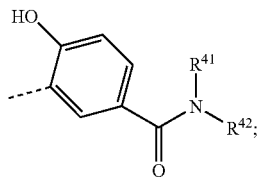

wherein $R^{41}$ is H or $(C_{1-6})$alkyl and $R^{42}$ is $(C_{1-6})$alkyl or $(C_{3-7})$cycloalkyl; or $R^{41}$ and $R^{42}$ are linked, together with the N to which they are attached, to form a 4- to 6-membered heterocycle optionally further containing 1 to 3 heteroatoms each independently selected from O, N and S; wherein the heterocycle is optionally substituted with 1 or 2 substituents each independently selected from $(C_{1-6})$alkyl, halo or —OH;
  wherein the $(C_{1-6})$alkyl is optionally substituted with —OH.

18. The compound according to claim 1, wherein $R^4$ is Het, wherein Het is a 5- or 6-membered heterocycle containing 1 to 3 heteroatoms each independently selected from N, O and S, or Het is a 9- or 10-membered heteropolycycle containing 1 to 3 heteroatoms each independently selected from N, O and S, wherein each N heteroatom may, independently and where possible, exist in an oxidized state such that it is further bonded to an oxygen atom to form an N-oxide group;
  wherein the Het is optionally substituted with 1 to 4 substituents each independently selected from $(C_{1-6})$alkyl, —NO$_2$, —OH and —C(=O)—N$(R^{41})R^{42}$;
  wherein $R^{41}$ is H or $(C_{1-6})$alkyl and $R^{42}$ is H or $(C_{1-6})$alkyl.

19. A pharmaceutically acceptable salt or ester thereof of a compound according to claim 1, 2, 3, 4, 5, 6, 7, 8, 9, 10, 11, 12, 13, 14, 15, 16, 17 or 18.

20. A pharmaceutical composition comprising a compound of formula (I) according to claim 1, 2, 3, 4, 5, 6, 7, 8, 9, 10, 11, 12, 13, 14, 15, 16, 17 or 18, or a pharmaceutically acceptable salt or ester thereof; and one or more pharmaceutically acceptable carriers.

21. A method for treating HIV infection in a host infected with HIV which method comprises administering to said host a therapeutically effective amount of a compound of the formula (I) according to claim 1, 2, 3, 4, 5, 6, 7, 8, 9, 10, 11, 12, 13, 14, 15, 16, 17 or 18 or a pharmaceutically acceptable salt or ester thereof.

* * * * *